(12) United States Patent
Heywood et al.

(10) Patent No.: US 12,417,825 B2
(45) Date of Patent: Sep. 16, 2025

(54) SYSTEMS AND METHODS FOR COLLECTING AND ANALYZING COMPREHENSIVE MEDICAL INFORMATION

(71) Applicant: Alden Scientific, Inc., Cambridge, MA (US)

(72) Inventors: James A. Heywood, Newton, MA (US); Paul J. Wicks, Alrewas (GB); Kimberley K. Goodwin, Oakland, CA (US); Renee Deehan-Kenney, Cambridge, MA (US)

(73) Assignee: ALDEN SCIENTIFIC, INC., Cambridge, MA (US)

(*) Notice: Subject to any disclaimer, the term of this patent is extended or adjusted under 35 U.S.C. 154(b) by 0 days.

(21) Appl. No.: 16/647,000

(22) PCT Filed: Sep. 14, 2018

(86) PCT No.: PCT/US2018/051249
§ 371 (c)(1),
(2) Date: Mar. 12, 2020

(87) PCT Pub. No.: WO2019/055879
PCT Pub. Date: Mar. 21, 2019

(65) Prior Publication Data
US 2020/0279622 A1    Sep. 3, 2020

Related U.S. Application Data

(60) Provisional application No. 62/559,246, filed on Sep. 15, 2017, provisional application No. 62/613,618, filed on Jan. 4, 2018.

(51) Int. Cl.
*G16H 10/60* (2018.01)
*G06N 5/02* (2023.01)
*G16H 10/20* (2018.01)

(52) U.S. Cl.
CPC ............ *G16H 10/60* (2018.01); *G06N 5/02* (2013.01); *G16H 10/20* (2018.01)

(58) Field of Classification Search
CPC .......... G16H 10/60; G16H 10/20; G06N 5/02
See application file for complete search history.

(56) References Cited

U.S. PATENT DOCUMENTS

| | | |
|---|---|---|
| 3,934,226 A | 1/1976 | Stone et al. |
| 4,712,562 A | 12/1987 | Ohayon et al. |

(Continued)

FOREIGN PATENT DOCUMENTS

| | | | |
|---|---|---|---|
| CA | 2884613 | 3/2014 | |
| CA | 2884613 A1 * | 3/2014 | ............ G06Q 50/24 |

(Continued)

OTHER PUBLICATIONS

Foraker et al., "EHR-based Visualization Tool: Adoption Rates, Satisfaction, and Patient Outcomes," eGEMs (Generating Evidence & Methods to improve patient outcomes): vol. 3: Iss. 2, Article 5, pp. 1-14 (Year: 2015).*

(Continued)

*Primary Examiner* — Jonathon A. Szumny
(74) *Attorney, Agent, or Firm* — Greenberg Traurig, LLP; David J. Dykeman; Kristopher Reichlen

(57) ABSTRACT

Systems and methods for collecting, analyzing, and reporting information relating to comprehensive medical information from one or more users are disclosed. In some aspects, a system for collecting and analyzing medical data includes a data management system for collecting and storing medical information relating to a user, and a knowledge creation engine in communication with the data management system and configured to analyze the stored medical information for creating at least one of personalized medical advice for the user and general scientific information relating to a medical (Continued)

condition. A display in communication with the data management system and the knowledge creation engine can be configured to present a digital representation of the user based on the stored medical information including electronic health record (EHR), patient reported outcomes (PROs), biological samples, wearable devices, sensors, medical devices, and dynamic questionnaires to create a digital representation of the user.

20 Claims, 48 Drawing Sheets

(56) References Cited

U.S. PATENT DOCUMENTS

| | | |
|---|---|---|
| 4,899,839 A | 2/1990 | Dessertine et al. |
| 5,014,798 A | 5/1991 | Glynn |
| 5,025,374 A | 6/1991 | Roizen et al. |
| 5,435,324 A | 7/1995 | Brill |
| 5,549,117 A | 8/1996 | Tacklind et al. |
| 5,594,637 A | 1/1997 | Eisenberg et al. |
| 5,594,638 A | 1/1997 | Iliff |
| 5,626,144 A | 5/1997 | Tacklind et al. |
| 5,653,739 A | 8/1997 | Maurer et al. |
| 5,692,215 A | 11/1997 | Kutzik et al. |
| 5,692,500 A | 12/1997 | Gaston-Johansson |
| 5,704,366 A | 1/1998 | Tacklind et al. |
| 5,713,350 A | 2/1998 | Yokota et al. |
| 5,720,502 A | 2/1998 | Cain |
| 5,732,709 A | 3/1998 | Tacklind et al. |
| 5,778,882 A | 7/1998 | Raymond et al. |
| 5,812,983 A | 9/1998 | Kumagai |
| 5,830,149 A | 11/1998 | Oka |
| 5,838,313 A | 11/1998 | Hou et al. |
| 5,937,387 A | 8/1999 | Summerell et al. |
| 5,950,168 A | 9/1999 | Simborg et al. |
| 5,984,368 A | 11/1999 | Cain |
| 5,991,729 A | 11/1999 | Barry et al. |
| 6,024,699 A | 2/2000 | Surwit et al. |
| 6,032,119 A | 2/2000 | Brown et al. |
| 6,067,523 A | 5/2000 | Bair et al. |
| 6,081,786 A | 6/2000 | Barry et al. |
| 6,102,874 A | 8/2000 | Stone et al. |
| 6,108,635 A | 8/2000 | Herren et al. |
| 6,108,685 A | 8/2000 | Kutzik et al. |
| 6,113,552 A | 9/2000 | Shimazu et al. |
| 6,168,569 B1 | 1/2001 | McEwen et al. |
| 6,186,145 B1 | 2/2001 | Brown |
| 6,231,560 B1 | 5/2001 | Bui et al. |
| 6,234,964 B1 | 5/2001 | Iliff |
| 6,235,964 B1 | 5/2001 | Kadash et al. |
| 6,236,983 B1 | 5/2001 | Hofmann et al. |
| 6,246,992 B1 | 6/2001 | Brown |
| 6,277,072 B1 | 8/2001 | Bardy |
| 6,282,441 B1 | 8/2001 | Raymond et al. |
| 6,283,923 B1 | 9/2001 | Finkelstein et al. |
| 6,294,999 B1 | 9/2001 | Yarin et al. |
| 6,314,405 B1 | 11/2001 | Richardson |
| 6,322,504 B1 | 11/2001 | Kirshner |
| 6,334,192 B1 | 12/2001 | Karpf |
| 6,335,907 B1 | 1/2002 | Momich et al. |
| 6,339,410 B1 | 1/2002 | Milner et al. |
| 6,380,858 B1 | 4/2002 | Yarin et al. |
| 6,400,996 B1 | 6/2002 | Hoffberg et al. |
| 6,405,034 B1 | 6/2002 | Tijerino |
| 6,484,144 B2 | 11/2002 | Martin et al. |
| 6,529,195 B1 | 3/2003 | Eberlein |
| 6,560,541 B1 | 5/2003 | Singh |
| 6,587,829 B1 | 7/2003 | Camarda et al. |
| 6,589,169 B1 | 7/2003 | Surwit et al. |
| 6,611,846 B1 | 8/2003 | Stoodley |
| 6,612,985 B2 | 9/2003 | Eiffert et al. |
| 6,690,397 B1 | 2/2004 | Daignault, Jr. |
| 6,723,045 B2 | 4/2004 | Cosentino et al. |
| 6,770,029 B2 | 8/2004 | Iliff |
| 6,789,091 B2 | 9/2004 | Gogolak |
| 6,802,810 B2 | 10/2004 | Ciarniello et al. |
| 6,856,315 B2 | 2/2005 | Eberlein |
| 6,915,170 B2 | 7/2005 | Engleson et al. |
| 6,929,607 B2 | 8/2005 | Lipman |
| 6,956,572 B2 | 10/2005 | Zaleski |
| 6,970,742 B2 | 11/2005 | Mann et al. |
| 6,980,958 B1 | 12/2005 | Surwit et al. |
| 6,988,075 B1 | 1/2006 | Hacker |
| 6,999,890 B2 | 2/2006 | Kai |
| 7,029,441 B2 | 4/2006 | Dodds |
| 7,039,878 B2 | 5/2006 | Auer et al. |
| 7,054,758 B2 | 5/2006 | Gill-Garrison et al. |
| 7,066,883 B2 | 6/2006 | Schmidt et al. |
| 7,107,547 B2 | 9/2006 | Cule et al. |
| 7,137,951 B2 | 11/2006 | Pilarski |
| 7,165,221 B2 | 1/2007 | Monteleone et al. |
| 7,169,085 B1 | 1/2007 | Killin et al. |
| 7,251,609 B1 | 7/2007 | McAlindon et al. |
| 7,286,997 B2 | 10/2007 | Spector et al. |
| 7,287,031 B1 | 10/2007 | Karpf et al. |
| 7,302,398 B2 | 11/2007 | Ban et al. |
| 7,330,818 B1 | 2/2008 | Ladocsi et al. |
| 7,337,121 B1 | 2/2008 | Beinat et al. |
| 7,428,494 B2 | 9/2008 | Hasan et al. |
| 7,725,328 B1 | 5/2010 | Sumner, II et al. |
| 7,761,311 B2 | 7/2010 | Clements et al. |
| 8,160,901 B2 | 4/2012 | Heywood et al. |
| 8,190,451 B2 | 5/2012 | Lloyd et al. |
| 8,214,224 B2 | 7/2012 | Rao et al. |
| 8,313,433 B2 | 11/2012 | Cohen et al. |
| 8,643,648 B2 | 2/2014 | Heywood et al. |
| 8,652,039 B2 | 2/2014 | Rosales et al. |
| 8,930,224 B2 | 1/2015 | Heywood et al. |
| 9,270,632 B2 | 2/2016 | Heywood et al. |
| 9,589,104 B2 | 3/2017 | Heywood et al. |
| 9,589,251 B2 | 3/2017 | Heywood et al. |
| 9,638,723 B2 | 5/2017 | Takagi et al. |
| 10,402,916 B2 | 9/2019 | Heywood et al. |
| 10,431,339 B1* | 10/2019 | Cornelius ............... G16H 10/60 |
| 10,664,572 B2 | 5/2020 | Bitran et al. |
| 10,665,344 B2 | 5/2020 | Heywood et al. |
| 10,832,816 B2 | 11/2020 | Heywood et al. |
| 11,010,843 B2 | 5/2021 | Heywood et al. |
| 2001/0034639 A1 | 10/2001 | Jacoby et al. |
| 2002/0010595 A1 | 1/2002 | Kapp |
| 2002/0026103 A1 | 2/2002 | Norris et al. |
| 2002/0072933 A1 | 6/2002 | Vonk et al. |
| 2002/0150872 A1 | 10/2002 | Glenn et al. |
| 2002/0177757 A1 | 11/2002 | Britton |
| 2002/0184094 A1 | 12/2002 | Calloway |
| 2003/0014006 A1 | 1/2003 | Alexandre et al. |
| 2003/0023461 A1 | 1/2003 | Quintanilla et al. |
| 2003/0065535 A1 | 4/2003 | Karlov et al. |
| 2003/0101076 A1 | 5/2003 | Zaleski |
| 2003/0125609 A1 | 7/2003 | Becker |
| 2003/0135128 A1 | 7/2003 | Suffin et al. |
| 2003/0140063 A1* | 7/2003 | Pizzorno ................ G16Z 99/00 |
| 2003/0163353 A1 | 8/2003 | Luce et al. |
| 2003/0187683 A1 | 10/2003 | Kirchhoff et al. |
| 2003/0233197 A1 | 12/2003 | Padilla et al. |
| 2004/0006444 A1 | 1/2004 | Kang et al. |
| 2004/0015337 A1 | 1/2004 | Thomas et al. |
| 2004/0030741 A1 | 2/2004 | Wolton et al. |
| 2004/0064447 A1 | 4/2004 | Simske et al. |
| 2004/0078237 A1 | 4/2004 | Kaafarani et al. |
| 2004/0103001 A1 | 5/2004 | Mazar et al. |
| 2004/0122707 A1 | 6/2004 | Sabol et al. |
| 2004/0132633 A1 | 7/2004 | Carter et al. |
| 2004/0161143 A1 | 8/2004 | Dietz et al. |
| 2004/0193448 A1 | 9/2004 | Woodbridge et al. |
| 2004/0210458 A1 | 10/2004 | Evans et al. |
| 2004/0225529 A1 | 11/2004 | Snyder et al. |
| 2004/0267570 A1 | 12/2004 | Becker |
| 2005/0080462 A1 | 4/2005 | Jenkins et al. |
| 2005/0085866 A1 | 4/2005 | Tehrani |
| 2005/0102160 A1 | 5/2005 | Brown |
| 2005/0102162 A1 | 5/2005 | Blumenfeld |

(56) References Cited

U.S. PATENT DOCUMENTS

| | | |
|---|---|---|
| 2005/0108051 A1 | 5/2005 | Weinstein |
| 2005/0119534 A1 | 6/2005 | Trost et al. |
| 2005/0144042 A1 | 6/2005 | Joffe et al. |
| 2005/0187866 A1 | 8/2005 | Lee |
| 2005/0191716 A1 | 9/2005 | Surwit et al. |
| 2005/0197545 A1 | 9/2005 | Hoggle |
| 2005/0197553 A1 | 9/2005 | Cooper |
| 2005/0216307 A1 | 9/2005 | Clements et al. |
| 2005/0272640 A1 | 12/2005 | Doyle et al. |
| 2005/0283384 A1 | 12/2005 | Hunkeler et al. |
| 2005/0283385 A1 | 12/2005 | Hunkeler et al. |
| 2005/0285746 A1 | 12/2005 | Sengupta et al. |
| 2006/0009810 A1 | 1/2006 | Mann et al. |
| 2006/0010098 A1 | 1/2006 | Goodnow et al. |
| 2006/0015369 A1 | 1/2006 | Bachus et al. |
| 2006/0020175 A1 | 1/2006 | Berry et al. |
| 2006/0030890 A1 | 2/2006 | Cosentino et al. |
| 2006/0031101 A1 | 2/2006 | Ross |
| 2006/0036134 A1 | 2/2006 | Tarassenko et al. |
| 2006/0036294 A1 | 2/2006 | Tehrani |
| 2006/0036619 A1 | 2/2006 | Fuerst et al. |
| 2006/0052945 A1 | 3/2006 | Rabinowitz et al. |
| 2006/0059160 A1 | 3/2006 | Smola et al. |
| 2006/0064030 A1 | 3/2006 | Cosentino et al. |
| 2006/0085217 A1 | 4/2006 | Grace |
| 2006/0089540 A1 | 4/2006 | Meissner |
| 2006/0122468 A1 | 6/2006 | Tavor |
| 2006/0249423 A1 | 11/2006 | Reijonen |
| 2006/0287885 A1 | 12/2006 | Frick |
| 2007/0005393 A1 | 1/2007 | Cole et al. |
| 2007/0015974 A1 | 1/2007 | Higgins et al. |
| 2007/0021979 A1 | 1/2007 | Cosentino et al. |
| 2007/0021984 A1 | 1/2007 | Brown |
| 2007/0048691 A1 | 3/2007 | Brown |
| 2007/0060803 A1 | 3/2007 | Liljeryd et al. |
| 2007/0061166 A1 | 3/2007 | Ramasubramanian et al. |
| 2007/0061487 A1 | 3/2007 | Moore et al. |
| 2007/0115282 A1 | 5/2007 | Turner et al. |
| 2007/0118348 A1 | 5/2007 | Brown |
| 2007/0168461 A1 | 7/2007 | Moore |
| 2007/0168501 A1 | 7/2007 | Cobb et al. |
| 2007/0203423 A1 | 8/2007 | Bardy |
| 2007/0214015 A1 | 9/2007 | Christian |
| 2007/0239416 A1 | 10/2007 | Saito et al. |
| 2007/0244372 A1 | 10/2007 | Merkle |
| 2007/0250134 A1 | 10/2007 | Miesel et al. |
| 2007/0288266 A1 | 12/2007 | Sysko et al. |
| 2008/0010089 A1 | 1/2008 | DiMaggio et al. |
| 2008/0015891 A1 | 1/2008 | Lee |
| 2008/0020877 A1 | 1/2008 | Bogner |
| 2008/0059232 A1 | 3/2008 | Iliff |
| 2008/0076976 A1 | 3/2008 | Sakurai et al. |
| 2008/0077489 A1 | 3/2008 | Gilley et al. |
| 2008/0091084 A1 | 4/2008 | Yudkovitch et al. |
| 2008/0109412 A1 | 5/2008 | Drayer et al. |
| 2008/0119958 A1 | 5/2008 | Bear et al. |
| 2008/0133269 A1* | 6/2008 | Ching .................. G06Q 10/10 705/2 |
| 2008/0133716 A1 | 6/2008 | Rao et al. |
| 2008/0140449 A1 | 6/2008 | Hayes |
| 2008/0147440 A1 | 6/2008 | Kil |
| 2008/0147441 A1 | 6/2008 | Kil |
| 2008/0147688 A1 | 6/2008 | Beekmann et al. |
| 2008/0200771 A1 | 8/2008 | Brown |
| 2008/0201174 A1* | 8/2008 | Ramasubramanian ..................... G16H 20/10 705/3 |
| 2008/0208777 A1 | 8/2008 | Stephens |
| 2008/0229213 A1 | 9/2008 | Hamilton et al. |
| 2008/0238666 A1 | 10/2008 | Loncar |
| 2008/0249806 A1 | 10/2008 | Dlugos et al. |
| 2008/0312510 A1 | 12/2008 | Ross |
| 2008/0313256 A1 | 12/2008 | Kanazawa et al. |
| 2009/0018862 A1 | 1/2009 | Sanger et al. |
| 2009/0037470 A1 | 2/2009 | Schmidt |
| 2009/0048865 A1 | 2/2009 | Breazeale, Jr. |
| 2009/0055150 A1 | 2/2009 | Prior et al. |
| 2009/0144089 A1 | 6/2009 | Heywood et al. |
| 2009/0150180 A1 | 6/2009 | Cohen et al. |
| 2009/0172773 A1 | 7/2009 | Moore |
| 2009/0222284 A1 | 9/2009 | McEachern |
| 2009/0234755 A1 | 9/2009 | Sidoruk |
| 2010/0070306 A1 | 3/2010 | Dvorak et al. |
| 2010/0131860 A1 | 5/2010 | DeHaan et al. |
| 2010/0286490 A1 | 11/2010 | Koverzin |
| 2011/0029895 A1 | 2/2011 | Ternouth |
| 2011/0184747 A1 | 7/2011 | Bozic et al. |
| 2012/0129139 A1* | 5/2012 | Partovi .................. G16H 40/67 434/262 |
| 2012/0265552 A1* | 10/2012 | Rabinowitz ............ G16H 10/60 705/2 |
| 2013/0024207 A1* | 1/2013 | Anderson ............... G16H 10/20 705/3 |
| 2013/0253940 A1 | 9/2013 | Zziwa |
| 2014/0100885 A1* | 4/2014 | Stern ...................... G16H 50/30 705/3 |
| 2014/0129246 A1* | 5/2014 | Vdovjak ................ G16H 10/60 705/2 |
| 2014/0257856 A1* | 9/2014 | Sasai ..................... G16H 50/30 705/3 |
| 2014/0350954 A1 | 11/2014 | Ellis et al. |
| 2015/0112710 A1 | 4/2015 | Haber et al. |
| 2015/0161331 A1* | 6/2015 | Oleynik ................ G16H 10/60 705/3 |
| 2016/0103973 A1* | 4/2016 | Singal ................... G16H 50/20 705/3 |
| 2016/0188807 A1 | 6/2016 | Heywood et al. |
| 2016/0203281 A1* | 7/2016 | Zalis .................... G16H 40/20 705/3 |
| 2016/0232312 A1 | 8/2016 | Apte et al. |
| 2016/0300015 A1* | 10/2016 | Natarajan ............. G16H 30/20 |
| 2017/0039344 A1* | 2/2017 | Bitran ................... G16H 20/10 |
| 2017/0140262 A1* | 5/2017 | Wilson .................. H04L 67/04 |
| 2017/0206327 A1 | 7/2017 | Heywood et al. |
| 2017/0220757 A1* | 8/2017 | Cox ...................... G16H 40/63 |
| 2017/0235885 A1* | 8/2017 | Cox ...................... G06Q 10/10 705/2 |
| 2017/0249434 A1 | 8/2017 | Brunner |
| 2017/0262604 A1* | 9/2017 | Francois ................ G16H 10/60 |
| 2018/0308569 A1* | 10/2018 | Luellen ................. G16H 20/10 |
| 2019/0043610 A1 | 2/2019 | Vaughan |
| 2019/0139641 A1 | 5/2019 | Itu et al. |
| 2019/0211378 A1 | 7/2019 | Apte et al. |
| 2019/0347744 A1 | 11/2019 | Heywood et al. |
| 2020/0003762 A1 | 1/2020 | Brown |
| 2020/0279622 A1 | 9/2020 | Heywood et al. |
| 2021/0057046 A1 | 2/2021 | Liu et al. |
| 2021/0247403 A1 | 8/2021 | Arvey et al. |
| 2021/0256630 A1 | 8/2021 | Heywood et al. |

FOREIGN PATENT DOCUMENTS

| | | |
|---|---|---|
| DE | 3703404 A1 | 8/1988 |
| EP | 0912957 B1 | 12/2004 |
| EP | 3287530 A1 | 2/2018 |
| JP | H07271857 A | 10/1995 |
| JP | H08140944 A | 6/1996 |
| JP | 2001175761 A | 6/2001 |
| JP | 2001331581 A | 11/2001 |
| JP | 2001331585 A | 11/2001 |
| JP | 2002011057 A | 1/2002 |
| JP | 2002041670 A | 2/2002 |
| JP | 2002056099 A | 2/2002 |
| JP | 2002095641 A | 4/2002 |
| JP | 2002512712 A | 4/2002 |
| JP | 2002245172 A | 8/2002 |
| JP | 2002245180 A | 8/2002 |
| JP | 2002539561 A | 11/2002 |
| JP | 2002366662 A | 12/2002 |
| JP | 2003010288 A | 1/2003 |
| JP | 2003 108679 A | 4/2003 |
| JP | 2003175005 A | 6/2003 |
| JP | 2003186995 A | 7/2003 |

(56) References Cited

FOREIGN PATENT DOCUMENTS

| | | | |
|---|---|---|---|
| JP | 2003256573 A | 9/2003 | |
| JP | 2003337864 A | 11/2003 | |
| JP | 2004178264 A | 6/2004 | |
| JP | 2005004398 A | 1/2005 | |
| JP | 2005506601 A | 3/2005 | |
| JP | 2005326943 A | 11/2005 | |
| JP | 2006053628 A | 2/2006 | |
| JP | 2006155071 A | 6/2006 | |
| JP | 2006155411 A | 6/2006 | |
| JP | 2006163489 A | 6/2006 | |
| JP | 2006185396 A | 7/2006 | |
| JP | 2006221471 A | 8/2006 | |
| JP | 2006350992 A | 12/2006 | |
| JP | 2007052774 A | 3/2007 | |
| JP | 2007514207 A | 5/2007 | |
| JP | 2007140905 A | 6/2007 | |
| JP | 2007200093 A | 8/2007 | |
| JP | 2007525154 A | 9/2007 | |
| JP | 2007265347 A | 10/2007 | |
| JP | 2008513884 A | 5/2008 | |
| JP | 2008177713 A | 7/2008 | |
| JP | 2010500648 A | 1/2010 | |
| JP | 2011501276 A | 1/2011 | |
| JP | 2011501845 A | 1/2011 | |
| WO | WO 2000029983 A1 | 5/2000 | |
| WO | WO 2000055751 A1 | 9/2000 | |
| WO | WO 2001050950 A2 | 7/2001 | |
| WO | WO 2004080312 A1 | 9/2004 | |
| WO | WO 2007019504 A2 | 2/2007 | |
| WO | WO 2007023818 A1 | 3/2007 | |
| WO | WO 2007111910 A2 | 10/2007 | |
| WO | WO 2009049277 A1 | 4/2009 | |
| WO | WO 2009049278 A1 | 4/2009 | |
| WO | WO 2010126577 A1 | 11/2010 | |
| WO | WO 2010148365 A2 | 12/2010 | |
| WO | WO 2012154594 | 11/2012 | |
| WO | WO 2014036312 A2 | 3/2014 | |
| WO | WO 2014039718 A1 | 3/2014 | |
| WO | WO 2014062981 A1 | 4/2014 | |
| WO | WO 2014144383 A1 | 9/2014 | |
| WO | WO 2014145123 A2 | 9/2014 | |
| WO | WO-2015095343 A1 * | 6/2015 | ........... G06F 19/322 |
| WO | 2016141127 A1 | 9/2016 | |
| WO | WO-2016170368 A1 * | 10/2016 | ......... G06F 17/2705 |
| WO | 2017181147 A1 | 10/2017 | |
| WO | WO 20170173365 A1 | 10/2017 | |
| WO | 2017201540 A1 | 11/2017 | |
| WO | 2018079840 A1 | 3/2018 | |
| WO | 2018140014 A1 | 8/2018 | |
| WO | 2019103738 A1 | 5/2019 | |

OTHER PUBLICATIONS

Eton et al., "Harmonizing and consolidating the measurement of patient-reported information at health care institutions: a position statement of the Mayo Clinic," Patient Related Outcome Measures 2014:5, pp. 7-15. (Year: 2014).*

Frost et al., "Social Uses of Personal Health Information Within PatientsLikeMe, an Online Patient Community: What Can Happen When Patients Have Access to One Another's Data," J Med Internet Res 2008 | vol. 10 | iss. 3 | e15 | pp. 1-10 (Year: 2008).*

Alves et al., "Progression of Motor Impairment and Disability in Parkinson Disease: A Population-Based Study," Neurology, vol. 65, No. 9, pp. 1436-1441, Nov. 2005.

Banerjee et al., "R-U-In ?: Doing What You Like, with People Whom You Like" In Proceedings of the 17th international conference on World Wide Web, pp. 1239-1240, Apr. 2008.

Baum et al., "A Maximization Technique Occurring in the Statistical Analysis of Probabilistic Functions of Markov Chains," Annals of Mathematical Statistics, 1970, vol. 41, No. 1, pp. 164-171.

Beenen et al., "Using Social Psychology to Motivate Contributions to Online Communities" Conference on Computer Supported Cooperative Work, Chicago, IL, Nov. 6-10, 2004.

Cedarbaum et al., "Performance of the Amyotrophic Lateral Sclerosis Functional Rating Scale (ALSFRS) in multicenter clinical trials," Journal of the Neurological Sciences, Oct. 1997, vol. 152, Supplement 1, pp. S1-S9.

Cedarbaum et al., "The ALSFRS-R: a revised ALS functional rating scale that incorporates assessments of respiratory function," Journal of the Neurological Sciences, 1999, vol. 169, pp. 13-21.

Cosley et al., "SuggestBot: Using Intelligent Task Routing to Help People Find Work in Wikipedia", IUI '07, Jan. 28-31, 2007, Honolulu, Hawaii, pp. 32-41.

Cudkowicz et al., "Measures & Markers in Amyotrophic Lateral Sclerosis," NeuroRx, Apr. 2004, vol. 1, pp. 273-283.

Dayhoff et al., "Providing a Complete Online Multimedia Patient Record," AMIA, Inc., 1999, pp. 241-245.

Deneault et al., "An Integrative Display for Patient Monitoring," IEEE International Conference on Systems, Man & Cybernetics Conference Proceedings, 1990, pp. 515-517.

Emmons et al., "Counting Blessings Versus Burdens: An Experimental Investigation of Gratitude and Subjective Well-Being in Daily Life," Journal of Personality and Social Psychology, 2003, vol. 84, No. 2, pp. 377-389.

Eton et al., "Harmonizing and Consolidating the Measurement of Patient-Reported Information at Health Care Institutions: a Position Statement of the Mayo Clinic," Patient Related Outcome Measures, pp. 7-15, 2014.

Foraker et al., "HER-based Visualization Tool: Adoption Rates, Satisfaction, and Patient Outcomes," eGEMS (Generating Evidence & Methods to Improve Patient Outcomes), vol. 3, Iss. 2, pp. 1-14, 2015.

Fornai et al., "Lithium delays progression of amyotrophic lateral sclerosis," Proceedings of the National Academy of Sciences, Feb. 12, 2008, vol. 105, No. 6, pp. 2052-2057.

Frankowski et al., "Recommenders Everywhere: The WikiLens Community-Maintained Recommender System", WikiSym '07, Oct. 21-23, 2007, Montreal, Quebec, Canada, pp. 47-59.

Frost et al., "Social Uses of Personal Health Information Within PatientsLikeMe, an Online Patient Community: What Can Happen When Patients Have Access to One Another's Data," Journal of Medical Internet Research, May 27, 2008, vol. 10, No. 3, p. e15.

Geyer et al., "Recommending Topics for Self-Descriptions in Online User Profiles", RecSys '08, Oct. 23-25, 2008, Lausanne, Switzerland, pp. 59-66.

Goetz, "Practicing Patients," The New York Times Magazine, Mar. 23, 2008.

Gordon, "Advances in Clinical Trials for Amyotrophic Lateral Sclerosis," Current Neurology & Neuroscience Reports, 2005, vol. 5, pp. 48-54.

Gordon et al., "Progression rate of ALSFRS-R at time of diagnosis predicts survival time in ALS," Neurology, Oct. 2006, vol. 67, pp. 1314-1315.

Harper et al., "Talk Amongst Yourselves: Inviting Users to Participate in Online Conversations", IUI '07, Jan. 28-31, 2007, Honolulu, Hawaii, pp. 62-71.

Ikemoto et al., "Diabetes nursing support system using mobile phones," Information Processing Society of Japan Research Report 2006-DBS-138 Database System 2006-GN-58 Groupware and Network IPSJ, Information Processing Society of Japan, Jan. 27, 2006, vol. 2006, No. 9, pp. 197-202.

Iriberri et al., "A Life-Cycle Perspective on Online Community Success", ACM Computing Surveys, vol. 41, No. 2, Article 11, Feb. 2009.

Johnson et al., "Prediction of the Rate of Decline in Cognitive Function in Alzheimer's Disease: A Model based on Simple Demographic Data and Widely Used Rating Scales" Dementia and Geriatric Disorders, vol. 15, No. 4, pp. 276-282, Sep. 2003.

Kasarskis et al., "Rating the severity of ALS by caregivers over the phone using ALSFRS-R," Amyotrophic Lateral Sclerosis & Other Motor Neuron Disorders, 2004, vol. 5, Supplement 2, p. 12.

Kasarskis et al., "Rating the severity of ALS by caregivers over the phone using ALSFRS-R," Amyotrophic Lateral Sclerosis, Mar. 2005, vol. 6, Iss. 1, pp. 50-54.

Koh et al., "Encouraging Participating in Virtual Communities", Communications of the ACM, col. 50, No. 2, Feb. 2007, pp. 69-73.

(56) References Cited

OTHER PUBLICATIONS

Litt et al., "Graphical Representation of Medical Information in the Visual Chart," Seventh Annual IEEE Symposium on Computer-Based Medical Systems, 1994, pp. 252-257.

Liu et al., "Towards a Rich-Context Participatory Cyberenvironment", International Workshops on Grid Computing Environments 2007, Nov. 11-12, 2007, Reno, Nevada.

Long et al., "Web Interface for the Heart Disease Program," Proceedings: AMIA Symposium, 1996, pp. 762-766.

Marquardt, "An Algorithm for Least-Squares Estimation of Nonlinear Parameters," Journal of the Society for Industrial and Applied Mathematics, Jun. 1963, vol. 11, Iss. 2, pp. 431-441.

Miller et al., "Is the ALSFRS-R Rate of Decline Linear Over Time?," Amyotrophic Lateral Sclerosis, Jan. 2007, vol. 8, Supplement 1, pp. 140-155.

Montes et al., "Development & Evaluation of self-administered version of the ALSFRS-R," Neurology, Oct. 2006, vol. 67, pp. 1294-1296.

Mould, "Developing Models of Disease Progression, Pharmacometrics: The Science of Quantitative Pharmacology" Wiley, Hoboken, pp. 547-581, 2007.

Nielsen, "Participation Inequality: Encouraging More Users to Contribute", Participation Inequality in Social Design, Oct. 2006.

Ogura et al., "Clinical Trial of Risedronate in Japanese Volunteers: A Study on the Effects of Timing of Dosing on Absorption," Journal of Bone and Mineral Metabolism, 2004, vol. 22, pp. 120-126.

Orimo et al., "Graphical Output of Health Testing Data," Medical Informatics, 1990, vol. 15, Iss. 2, pp. 141-149.

"Pediatric Research Program Issue APS-SPR," San Diego Convention Center, San Diego, CA, May 7-11, 1995, vol. 37, No. 4 Part 2, p. 139A (Apr. 1995).

Rashid et al., "Motivating Participating by Displaying the Value of Contribution", CHI 2006, Apr. 22-27, 2006, Montreal, Quebec, Canada, pp. 955-958.

Seligman et al., "Positive Psychology Progress," American Psychologist, Jul.-Aug. 2005, pp. 410-421.

U.S. FDA, "Guideline for Industry: Dose Response Information to Support Drug Registration," U.S. FDA; Federal Register, Nov. 9, 1994, vol. 59, No. 216.

Wicks et al., "Accelerated clinical discovery using self-reported patient data collected online and a patient-matching algorithm," Nature Biotechnology, May 2011, vol. 29, No. 5, pp. 411-414.

Aljaaf et al., "Early Prediction of Chronic Kidney Disease Using Machine Learning Supported by Predictive Analytics," IEEE Congress on Evolutionary Computation, 2018.

Bratic et al., "Machine Learning for Predicting Cognitive Diseases: Methods, Data Sources and Risk Factors," J. Med. Syst., vol. 42, No. 243, 2018.

Eom et al., "AptaCDSS-E: A Classifier Ensemble-Based Clinical Decision Support System for Cardiovascular Disease Level Prediction," Expert Systems with Applications, vol. 34, pp. 2465-2479, (2008).

Ko et al., "Machine Learning to Detect Signatures of Disease in Liquid Biopsies—A User's Guide," Lab Chip, vol. 18, pp. 395-405, 2018.

Margineanu et al., "Machine Learning Approach for Classifying Multiple Sclerosis Courses by Combining Clinical Data with Lesion Loads and Magnetic," Frontiers in Neuroscience, vol. 11, Art. 398, Jul. 1, 2017.

Piri et al., "A Data Analytics Approach to Building a Clinical Decision Support System for Diabetic Retinopathy: Developing and Deploying a Model Ensemble," Decision Support Systems, vol. 101, Dec. 27, 2017.

* cited by examiner

HOME MY HEALTH PATIENTS FORUMS CONDITIONS TREATMENTS SYMPTOMS RESEARCH ☒ ⌂

< Parkinson's disease      Save

Settings Related Variants Stages Symptoms Treatments Providers Labs Community Abilities Experiences Symptoms

| Name | Default monitored ⓘ | First symptom question ⓘ | Last modified | |
|---|---|---|---|---|
| constipation | ☑ | ☐ | | |
| excess saliva | ☑ | ☐ | Apr 06 2017 | 📄 |
| falls | ☑ | ☐ | Nov 01 2017 | 📄 |
| freezing of gait | ☑ | ☐ | Nov 1 2017 | 📄 |
| jerky movements | ☑ | ☐ | Dec 19 2016 | 📄 |
| numbness and tingling with pins and needles | ☑ | ☐ | Apr 06 2017 | 📄 |
| slow movements (bradykinesia) | ☑ | ☐ | | 📄 |
| stiffness/spasticity | ☑ | ☐ | | 📄 |
| tremor(s) | ☑ | ☐ | Apr 06 2017 | 📄 |
| visual hallucinations | ☑ | ☐ | Apr 06 2017 | 📄 |

Add a symptom:

[ Start typing to see suggestions 🔍 ]

▲ Back to top

Parkinson's disease

HOME | MY HEALTH | PATIENTS | FORUMS | CONDITIONS | TREATMENTS | SYMPTOMS | RESEARCH

Settings  Related  Variants  Stages  Symptoms  Treatments  Providers  Labs  Community  Abilities  Experiences

Experiences

The MonthlyMe interview asks patients about a default set of experiences (feel good about yourself, find meaning in your life, feel connected to others, feel able to take charge of your health, and feel able to live the life you wanted) plus any experiences associated with his or her conditions. You can set the experiences associated with Parkinson's disease here.

feel motivated to do everyday things ×

*Default experiences are associated with all conditions and will not appear as options*

Save

▲ Back to top

FIG. 6A

Activity APIs Clinical codes |Conditions| Drug safety Forums Interviews Labs Mail Medical entity tags Medical provider types News feed Omics eligibility Omics participants Polls Security Surveys
Symptoms Thrive abilities Thrive experiences Topics Treatments User voices Users Preferences | Admin | PV | FAQ | Crisis | Logout

✉ ◇

HOME   MY HEALTH   PATIENTS   FORUMS   CONDITIONS   TREATMENTS   SYMPTOMS   RESEARCH

☑ status epilepticus

Settings   Related   Variants   Stages   Symptoms   Treatments   Providers   Labs   Community   Abilities   Experiences

| Created: Aug 22, 2018 by GabbyF.Jones | Last modified: Sep 05, 2018 | Patients:1 | View patient community page |

Name
| status epilepticus |

Short name
| status epilepticus |

Short definition
Active. Displayed in hover on condition picker.
| Status epilepticus (SE) refers to a life-threat-ening condition in which the brain is in a state of persistent seizure. This condition is most common in known epileptics. |

Key
| status-epilepticus |

UMLS synonyms
| Status epilepticus grand mal, Grand mal status, epileptic, Convulsive status epilepticus, Complex partial status epilepticus, Nonconvulsive status epilepticus, Epilepsia |

Admin synonyms
Comma separated. Used to expand search matches
| |

Condition category
Warning: Changing this affects existing condition histories.
| Event ▼ |

Getting diagnosed interview
Selecting an interview replaces the condition info form with a question card interview. For a list of questions in each interview, see: NOA Interviews
| ▼ |

| diagnosis-chronic ▼ |

Hidden from search
When 'yes', condition is not searchable by users.
○ Yes
● No

Site options
☐ Allow multiple chart instances

Save

⊙ Help

FIG. 6B

Activity APIs Clinical codes Conditions Drug safety Forums |Interviews| Labs Mail Medical entity tags Medical provider types News feed Omics eligibility Omics participants Polls Security Surveys Symptoms Thrive abilities Thrive experiences Topics Treatments User voices Users Preferences | Admin | PV | FAQ | Crisis | Logout ✉ 🔔

HOME  MY HEALTH  PATIENTS  FORUMS  CONDITIONS  TREATMENTS  SYMPTOMS  RESEARCH

Interview dashboard condition_infos-condition_resolved
condition_infos-diagnosis_chanaged
day_of_draw
diagnosis-acute
diagnosis-base
diagnosis-chronic
diagnosis-chronic_no_onset
diagnosis-lifestage
lupus_standard_of_care
menstruation_and_pregnancy
monthly_check_in
omics_eligibility
symptoms
thrive
user_basic_info (?) Help

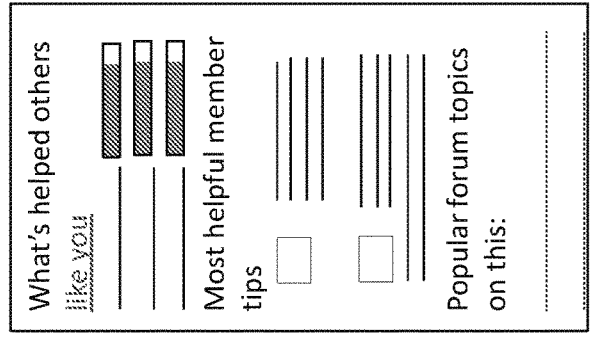
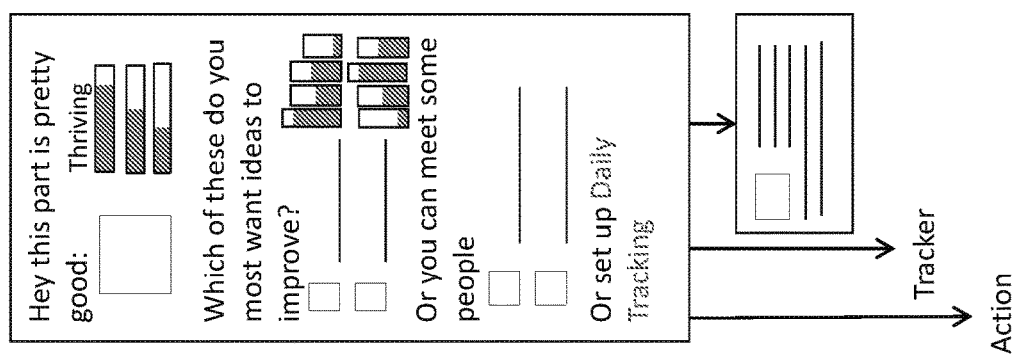
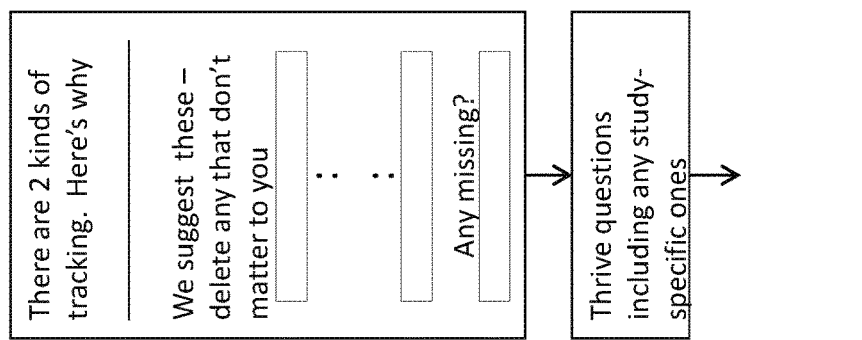
FIG. 8A
How are you #1 - Overview

FIG. 8B

How are you feeling about life?
Your health affects how your feel... and how you feel affects your health.

Over the last month, how often did you find meaning in your life?

○ All of the time

○ Most of the time

○ Some of the time

○ None of the time

○ Stop asking me this

Finish later

Finish later

Standard question stems / responses + database tables of medical objects

Symptoms
pain, fatigue, rash, anxious mood...

In the last < time >,
how severe was
any < symptom >?

- None
- Mild
- Moderate
- Severe

Abilities
walk, think, see, manage emotions...

In the last < time >,
how well could you
< ability >?

- Extremely well
- Very well
- Fairly well
- Poorly
- Not at all

Experiences
feel connected to others, able to cope...

In the last < time >,
how often could you
< experience >?

- All of the time
- Most of the time
- Some of the time
- None of the time

FIG. 12

Plus, Lupus specific items + flare reports

| | Common symptoms | How bad it is | What people are taking for it |
|---|---|---|---|
| Lupus | Muscle pain | | Tramadol, Methocarbamol, Carisoprodol |
| Core | Fatigue | | Rest, Modafinil, Amphetamine-Dextroamphetamine |
| Lupus | Headaches | | Ibuprofen, Acetaminophen-asprin-caffeine, Topiramate |
| Lupus | Joint pain | | Hydroxychloroquine, Prednisone, Meloxicam |
| Lupus | Raynaud's phenomenon | | Amlodipine, Nifedipine, Nitroglycerine topical |
| Core | Pain | | Tramadol, Hydrocodone-Acetaminophen, Gabapentin |
| Lupus | Joint swelling | | Prednisone, Celecoxib, Ibuprofen |
| Lupus | Skin sensitivity to sun (Photosensitivity) | | Avoid sunlight, Hyrdoxychloroquine, Quinacrine |
| Lupus | Chest pain | | Nitroglycerin, Electrocardiagram (EKG), Metoprolol |
| Core | Insomnia | | Amitriptyline, Zolpidem, Trazodone |
| Core | Anxious mood | | Alprazolam, Clonazepam, Lorazepam |
| Core | Depressed mood | | Duloxetine, Sertraline, Bupropion |

+ "Do you think you're having a flare or relapse (with new or worse symptoms) right now?

FIG. 14

User 1: female with Parkinson's

- Female history questions e.g. pregnancy status
- PD experiences e.g. motivation
- PD symptoms e.g. Tremors, Gait disturbances
- PD abilities e.g. Short term memory, Use of hands, Swallowing
- Core history e.g. treatment list
- Core experiences e.g. self esteem
- Core symptoms e.g. pain, depression
- Core abilities e.g. walking, cognition

User 2: male with psoriasis

- Psoriasis history questions e.g. subtype
- No additional psoriasis experiences
- Psoriasis Symptoms e.g. Skin plaques, Skin redness
- No additional psoriasis abilities
- Core history e.g. treatment list
- Core experiences e.g. self esteem
- Core symptoms e.g. pain, depression
- Core abilities e.g. walking, cognition

FIG. 15

How will it work?

Each member gets a personalized set of symptom, ability, and experience questions

Scoring v.1: static
- Traditional "PRO" scores based on core domains
- Subsets of items used for disease specific scores

Scoring v.2: dynamic
- Disease-specific scoring remains static
- "Thriving" score accounts for ALL of a member's domains With a detailed history and some biological samples, we can combine the latest medical evidence and patient experience data to help you achieve your goals.

*WHOLE HEALTH RESEARCH SERVICE:*

A comprehensive multi-omics panel and a personal research advisor will help you make the best of your health with ongoing updates based on new evidence.

☐ Tell me what can help me (Includes best plan and screening)

*FIND THE BEST PLAN FOR ME:*

Given your conditions, history, and biology, what should you consider doing?

☐ Which MS treatment?

☐ Which diabetes treatment?

☐ How should I eat?

☐ What exercise plan?

*SEE IF SOMETHING IS WORKING*

Considering a change in treatment, diet, or other behavior? Sometimes it's hard to see what helps. You can *design your own experiment.*

HOME MY HEALTH PATIENTS FORUMS CONDITIONS TREATMENTS SYMPTOMS RESEARCH

Treatments taken by people with multiple sclerosis                                    ☒  Follow Community goals
Overview
How it affects people
How people treat it
Compare treatments
MS news feed
Who's new
Join the conversation
Chronic Pain forum
Immune, Inflammatory and Infections forum
Multiple Sclerosis forum
Neurological and Brain forum Show:
all treatments ▼

| Treatment name(s): | Type: | How many have tried: | | Tried for: |
|---|---|---|---|---|
| Dimethyl fumarate (Tecfidera) | Prescription drug | 709 | | multiple sclerosis (709), fatigue (1) |
| Glatiramer acetate (Copaxone) | Prescription drug | 454 | | multiple sclerosis (454), stiffness/spasticity (4), 2 more |
| Fingolimod (Gilenya) | Prescription drug | 248 | | multiple sclerosis (248) |
| Teriflunomide (Aubagio) | Prescription drug | 242 | | multiple sclerosis (242) |
| Natalizumab (Tysabri) | Prescription drug | 235 | | multiple sclerosis (235), fatigue (1) |
| Baclofen (Mylan-Baclofen) | Prescription drug | 204 | | stiffness/spasticity (151), multiple sclerosis (119), 1 more |
| Interferon beta-1a IM injection (Avonex) | Prescription drug | 102 | | multiple sclerosis (102), fatigue (2) |

⊙ Help

FIG. 19C

HOME  MY HEALTH  PATIENTS  FORUMS  CONDITIONS  TREATMENTS  SYMPTOMS  RESEARCH

Filter by patients with: [All ▼]  [Look up a condition]

Dimethyl fumarate treatment report

Overview   Individual patient evaluations

599 patient evaluations for Dimethyl fumarate                                   Sort by: [Most recent ▼]

( J ) xxxxxx   Aug 31, 2018 (Started May 15, 2017)
  Effectiveness  ▓▓▓▓▓▓▓▓□  Moderate (for multiple sclerosis)
  Side effects   ▓▓▓□□□□□□  Mild (muscle fatigue)
  Adherence      ▓▓▓▓▓▓▓▓▓  Always
  Burden         ▓▓□□□□□□□  Not at all hard to take
  Cost: $25-49 monthly
  👍 1  |  🔖 Mark this evaluation as helpful ( E ) xxxxxx   Aug 20, 2018 (Started Feb 15, 2017)
  Effectiveness  ▓▓▓▓▓▓▓▓□  Moderate (for multiple sclerosis)
  Side effects   ▓▓▓□□□□□□  Mild (flushing)
  Adherence      ▓▓▓▓▓▓▓▓▓  Always
  Burden         ▓▓□□□□□□□  Not at all hard to take
  Dosage: 240mg Twice daily
  👍 3  |  🔖 Mark this evaluation as helpful (?) Help

FIG. 20B

Glatiramer acetate treatment report

Overview | Individual patient evaluations

2155 patient evaluations for Glatiramer acetate taken for the purpose of 'multiple sclerosis'    Sort by: [Most recent ▼]

T xxxxxx

Sep 1, 2018 (Started Jan 17, 2009)
- Effectiveness ☐☐☐☐ Can't tell (for multiple sclerosis)
- Side effects ☐☐☐ None
- Adherence ▨▨▨▨ Always
- Burden ▨☐☐ Not at all hard to take
- Dosage: 20 mg Daily
- Cost: < $25 monthly Jun 7, 2018 (Started Jan 17, 2009)
- Effectiveness ▨▨☐☐ Moderate (for multiple sclerosis)
- Side effects ▨☐☐ None
- Adherence ▨▨▨▨ Always
- Burden ▨☐☐ Not at all hard to take
- Dosage: 20mg Twice daily
- Cost: < $25 monthly Dec 17, 2015 (Started Jan 17, 2009)
- Effectiveness ▨▨☐☐ Moderate (for multiple sclerosis)
- Side effects ▨☐☐ None
- Adherence ▨▨▨▨ Always
- Burden ▨☐☐ Not at all hard to take
- Dosage: 20mg Twice daily
- Cost: < $25 monthly (?) Help

FIG. 20C

Dosages
Based on patients currently taking Glatiramer acetate

| Dosage | Patients |
|---|---|
| 20 mg daily | 194 |
| 40 mg m,w,f | 69 |
| 40 mg 3 times a week | 57 |
| 20 mg every other day | 11 |
| daily | 11 |
| 40 mg every other day | 8 |
| 40 mg three times daily | 5 |
| 20 mg 3 times a week | 4 |
| 120 mg weekly | 4 |
| 20 mg weekly | 3 |
| ▸ See all 33 dosages | |

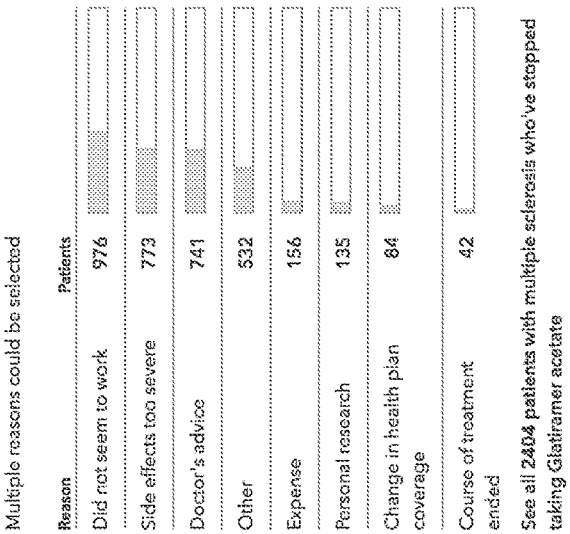

Why patients stopped taking Glatiramer acetate
Multiple reasons could be selected

| Reason | Patients |
|---|---|
| Did not seem to work | 976 |
| Side effects too severe | 773 |
| Doctor's advice | 741 |
| Other | 532 |
| Expense | 156 |
| Personal research | 135 |
| Change in health plan coverage | 84 |
| Course of treatment ended | 42 |

See all 2404 patients with multiple sclerosis who've stopped taking Glatiramer acetate

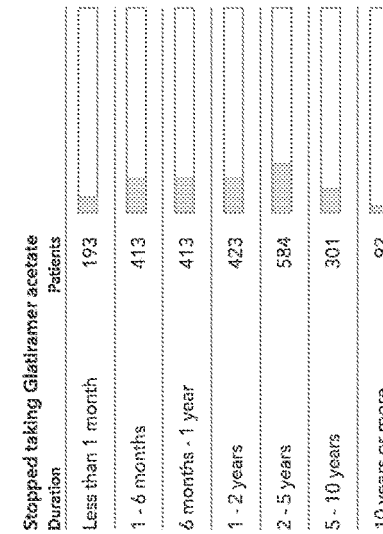

Duration
Currently taking Glatiramer acetate

| Duration | Patients |
|---|---|
| 1 - 6 months | 7 |
| 6 months - 1 year | 11 |
| 1 - 2 years | 21 |
| 2 - 5 years | 89 |
| 5 - 10 years | 130 |
| 10 years or more | 138 |

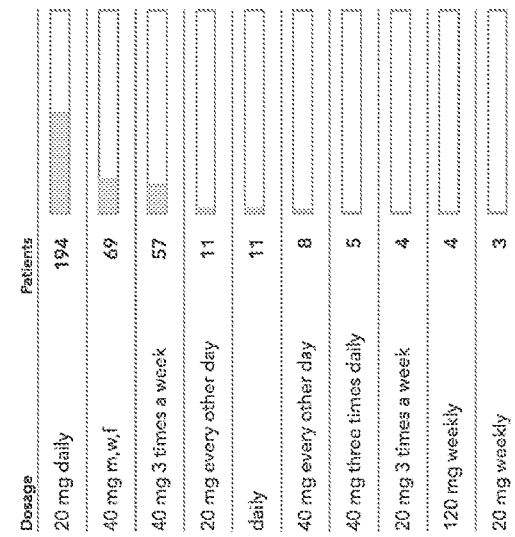

Stopped taking Glatiramer acetate

| Duration | Patients |
|---|---|
| Less than 1 month | 193 |
| 1 - 6 months | 413 |
| 6 months - 1 year | 413 |
| 1 - 2 years | 423 |
| 2 - 5 years | 584 |
| 5 - 10 years | 301 |
| 10 years or more | 92 |

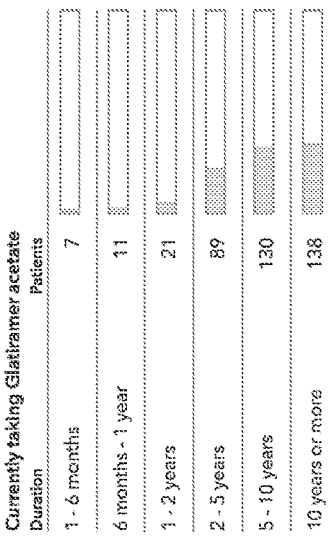

FIG. 20F

What people switch to and from
Patients started taking Glatiramer acetate after stopping:

| Treatment | Patients |
|---|---|
| Interferon beta-1a IM Injection (Avonex) | 67 |
| Interferon beta-1a SubQ injection (Rebif) | 51 |
| Dimethyl fumarate (Tecfidera) | 39 |
| Interferon beta-1b SubQ Injection (Betaseron) | 26 |
| Natalizumab (Tysabri) | 15 |

▸ Show all 13 treatments patients report switching from

Patients stopped taking Glatiramer acetate and switched to:

| Treatment | Patients |
|---|---|
| Dimethyl fumarate (Tecfidera) | 95 |
| Natalizumab (Tysabri) | 63 |
| Teriflunomide (Aubagio) | 46 |
| Fingolimod (Gilenya) | 42 |
| Interferon beta-1a SubQ injection (Rebif) | 34 |

▸ Show all 26 treatments patients report switching to

SYSTEMS AND METHODS FOR COLLECTING AND ANALYZING COMPREHENSIVE MEDICAL INFORMATION

RELATED APPLICATIONS

This application claims the benefit of and priority to U.S. Provisional Application Ser. No. 62/559,246, filed Sep. 15, 2017, and U.S. Provisional Application Ser. No. 62/613,618, filed Jan. 4, 2018, both of which are incorporated herein by reference in its entirety.

FIELD

The present disclosure relates to systems and methods for collecting, analyzing, and reporting information relating to comprehensive medical information from one or more users.

BACKGROUND

For many years, people have been contributing to digital health systems hoping for the promise of personalized medicine. Patients post comments about symptoms, medications, treatments, efficacy, and side effects to message boards and focus groups on the internet. Many healthcare providers are using electronic health records (EHR). Medical advancement is increasingly relying on real-world evidence and patient feedback to improve treatment plans.

Current digital health systems and electronic health records lack standards regarding discrete data, have no integrated communication, cannot analyze the large amount of medical data to provide a course of action or recommendation, are not user friendly, do not have simple, functional, and aesthetically pleasing interfaces, and face increasing security risks to stored patient data. There exists a need for digital health systems that collect, aggregate and analyze medical information and data from numerous sources to determine various treatment options.

SUMMARY

Systems and methods for collecting, analyzing, and reporting information relating to comprehensive medical information from one or more users are disclosed herein. In some aspects, a system for collecting and analyzing medical data is provided and can include a data management system for collecting and storing medical information relating to a user, and a knowledge creation engine in communication with the data management system and configured to analyze the stored medical information for creating at least one of personalized medical advice for the user and general scientific information relating to a medical condition.

A display can be in communication with the data management system and the knowledge creation engine. The display can e configured to present a digital representation of the user based on the stored medical information. The medical information can include data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires to create a digital representation of the user.

In some embodiments, the system can also include a healthcare provider engine in communication with the data management system and that is configured to generate a healthcare provider preparation document that captures information relating to the aggregated medical information to present a current state of the user to a healthcare provider before a scheduled appointment with the healthcare provider.

In some embodiments, the one or more dynamic questionnaires includes a plurality of questions determined by a rules engine based on the stored medical information. In some embodiments, the system can also include an insight engine that is configured to generate insight information for the user using the analyzed data. The insight information can be at least partially based on user attributes of a subset of users having stored data similar to the user. In some embodiments, the insight information can include at least one of aggregated user data, health assessments, personalized medical advice, customized reports for clinicians, research results, user givebacks and customized reports related to genome/exome sequencing, transcriptomics, metabolomics, proteomics, immunosignature, and microflora/fauna.

In some aspects, a system for aggregating and analyzing data from a community is provided and can include a data management system configured to receive and store data from a plurality of users. The data relates to medical information and health status information for each of the plurality of users. A processor can be in communication with the data management system and configured to perform the steps of analyzing the stored data for the plurality of users and generating insight information for at least one of the plurality of users using the analyzed data. The insight information can be at least partially based on user attributes of a subset of the plurality of users having stored data substantially similar to the at least one of the plurality of users. The data can include at least one of an electronic health record (EHR), patient reported outcomes (PROs), one or more biological samples, data from one or more wearable devices, data from one or more sensors configured to collect data relating to a biological condition of the user, data from one or more medical devices, and results from one or more dynamic questionnaires to create a digital representation of the at least one user.

In some embodiments, the insight information can include at least one of aggregated user data, health assessments, personalized medical advice, customized reports for clinicians, research results, user givebacks and customized reports related to genome/exome sequencing, transcriptomics, metabolomics, proteomics, immunosignature, and microflora/fauna.

In some aspects, a method for collecting and analyzing data is provided that includes aggregating medical information relating to a user to create a digital representation of the user, and analyzing the aggregated medical information using a computational knowledge engine. The medical information can include data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires. The method also includes generating insight information using the computational knowledge engine. The insight information relates to the aggregated medical information for presentation to the user on a display, and can be at least partially based on user attributes of a plurality of users having medical profiles similar to the user. Also disclosed is a non-transitory computer readable recording medium having a program for implementing the method for collecting and analyzing medical data.

In some embodiments, the one or more dynamic questionnaires can include a plurality of questions determined by a rules engine based on the aggregated medical information. In some embodiments, the rules engine can determine an order of the plurality of questions.

In some embodiment, the insight information can include unique information for a user at least partially based on information from the plurality of users with similar medical profiles. In some embodiments, the insight information can include at least one of aggregated user data, health assessments, personalized medical advice, customized reports for clinicians, research results, user givebacks and customized reports related to genome/exome sequencing, transcriptomics, metabolomics, proteomics, immunosignature, and microflora/fauna. In some embodiments, the insight information can include a visual representation of a disease, a user's life strategy, or other information collected and/or processed by the computational knowledge engine, and is presented to a user to visually convey an understanding of their condition/illness or health status.

In some embodiments, the method can also include generating a healthcare provider preparation document that captures information relating to the aggregated medical information to present a current state of the user to the healthcare provider before a scheduled appointment with the healthcare provider. In some embodiments, the method can also include determining which data to collect and at what frequency and priority using the aggregated medical information.

In some embodiments, the method can also include using a phenotype measurement system to determine which data to collect. In some embodiments, the phenotype measurement system can be configured to determine state changes in a status of the user for triggering the collection of biological samples.

In some aspects, a method for collecting and analyzing data is provided that includes aggregating medical information relating to a plurality of users, and analyzing the aggregated medical information using a computational knowledge engine. The medical information can include data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires. Research information can be generated using the analyzed aggregated medical information. The research information includes results of one or more experiments run using the aggregated medical information of a subset of the plurality of users having user attributes related to one another. In some embodiments, the one or more experiments are clinical trials. In some embodiments, the method can also include communicating with the subset of the plurality of users consent information for participation in the clinical trials for which the subset of the plurality of users are determined to be eligible based on the aggregated medical information. Also disclosed is a non-transitory computer readable recording medium having a program for implementing the method for collecting and analyzing data.

In some aspects, a computer program product for use in a system for collecting and analyzing medical data comprising: a data management system for collecting and storing medical information relating to a user, the medical information including data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires to create a digital representation of the user; a knowledge creation engine in communication with the data management system, the knowledge creation engine configured to analyze the stored medical information for creating at least one of personalized medical advice for the user and general scientific information relating to a medical condition, and a display in communication with the data management system and the knowledge creation engine, the display configured to present a digital representation of the user based on the stored medical information.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 5A, FIG. 5B, and FIG. 5C are exemplary embodiments of a user interface for assigning attributes to medical objects;

FIG. 6A, FIG. 6B, FIG. 6C, and FIG. 6D are exemplary embodiments of a user interface for relating the assignment of medical objects;

FIG. 7 is an exemplary embodiment of a user interface for relating the assignment of medical objects;

Figure 8B:
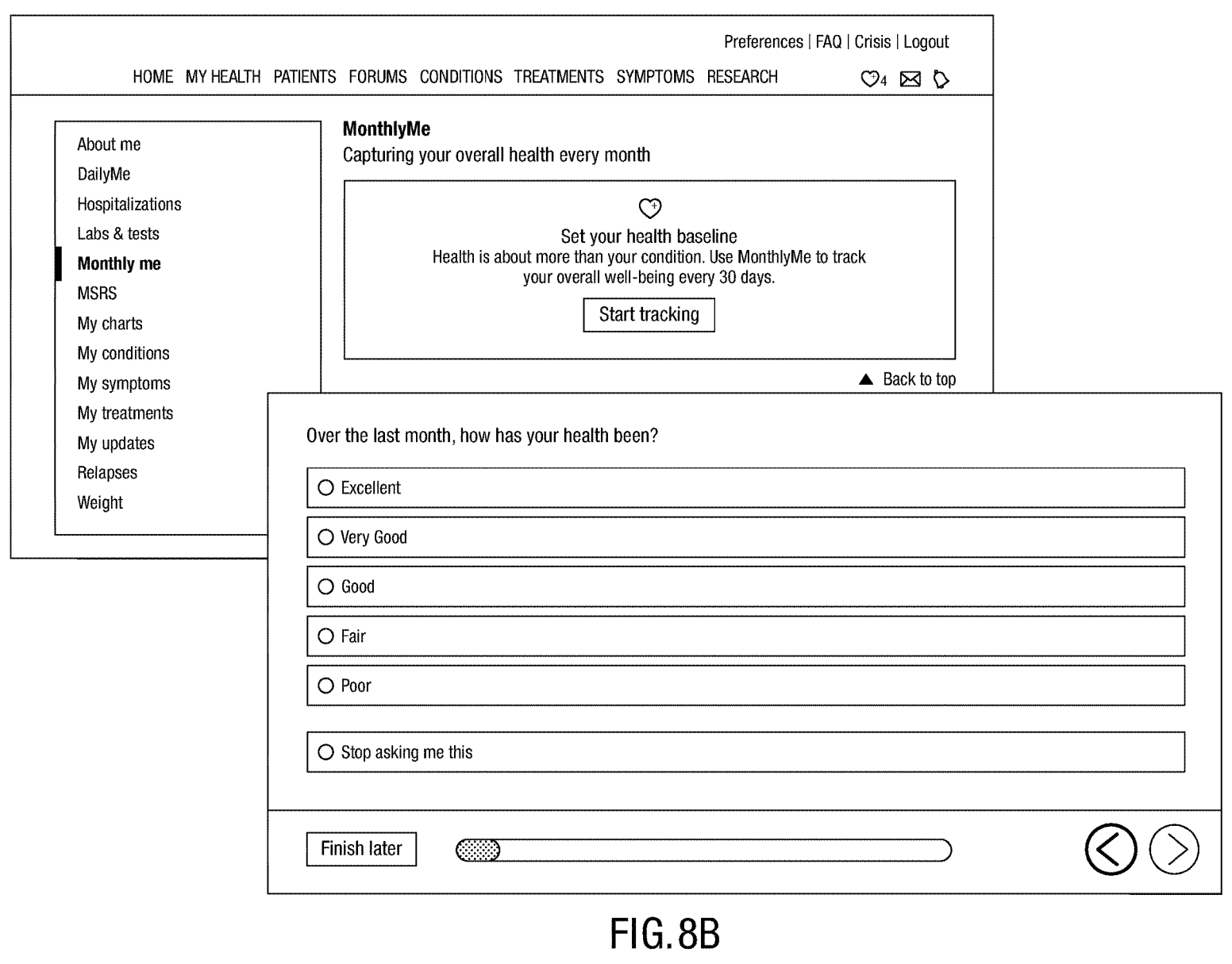
Figure 8F:
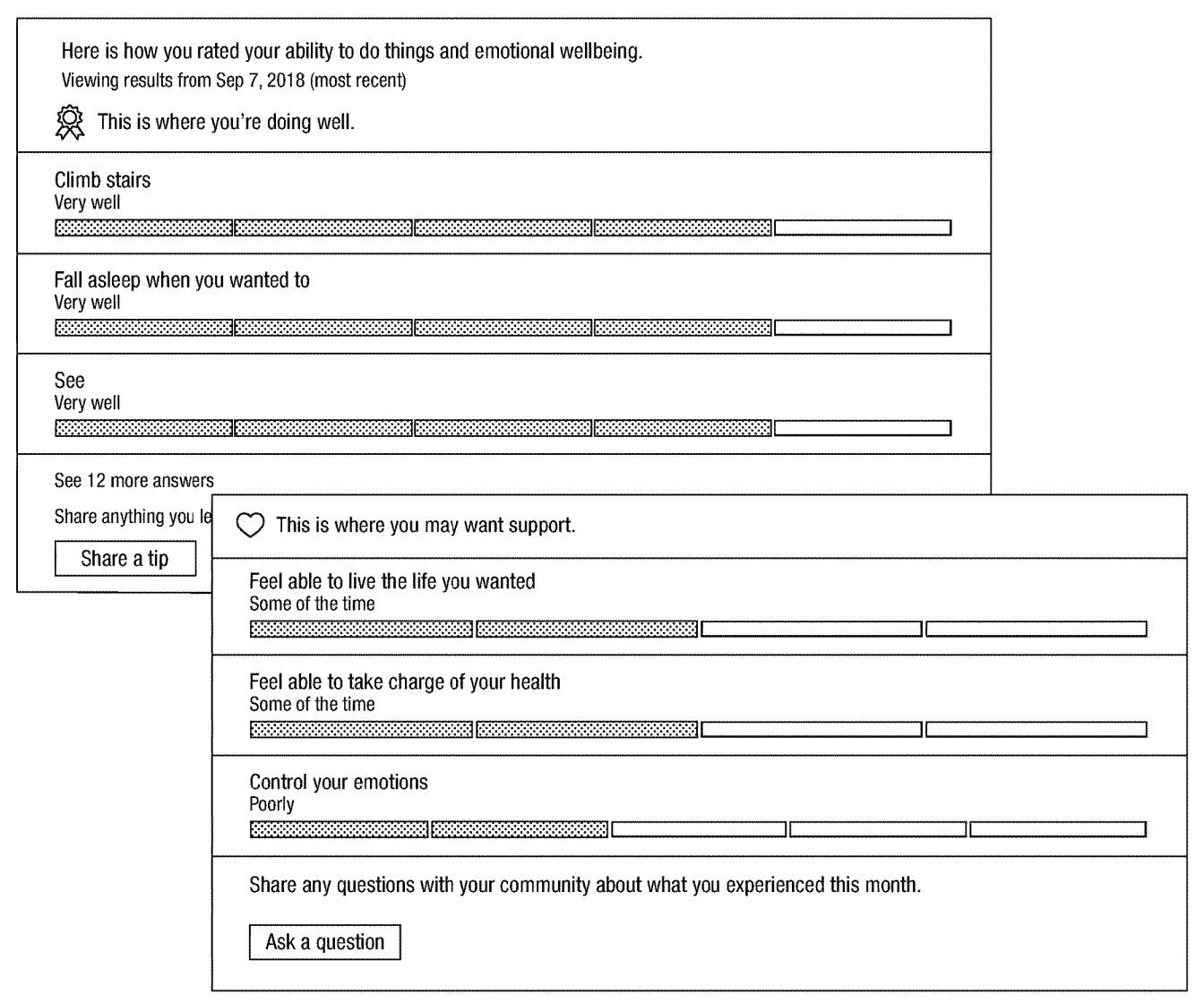

FIG. 8A, FIG. 8B, FIG. 8C, FIG. 8D, FIG. 8E, and FIG. 8F illustrate exemplary embodiments of a user interface for collecting data from a user;

FIG. 12 illustrates an exemplary embodiment of standard questions and responses that can be built as medical objects;

FIG. 14 illustrates an exemplary embodiment of dynamically-created questionnaires relating to the symptoms associated with one or more illnesses;

FIG. 15 illustrates an exemplary embodiment of dynamically-created questionnaires relating to the symptoms associated with one or more illnesses;

FIG. 18 is an exemplary embodiment of consumer offerings based on data that can be presented to a user;

FIG. 19A, FIG. 19B and FIG. 19C are exemplary embodiments of data presented to a user;

FIG. 20A, FIG. 20B, FIG. 20C, FIG. 20D, FIG. 20E, FIG. 20F, FIG. 20G, and FIG. 20H are exemplary embodiments of data presented to a user;

FIG. 22A and FIG. 22B are exemplary user interfaces for displaying insight information;

Figure 1:
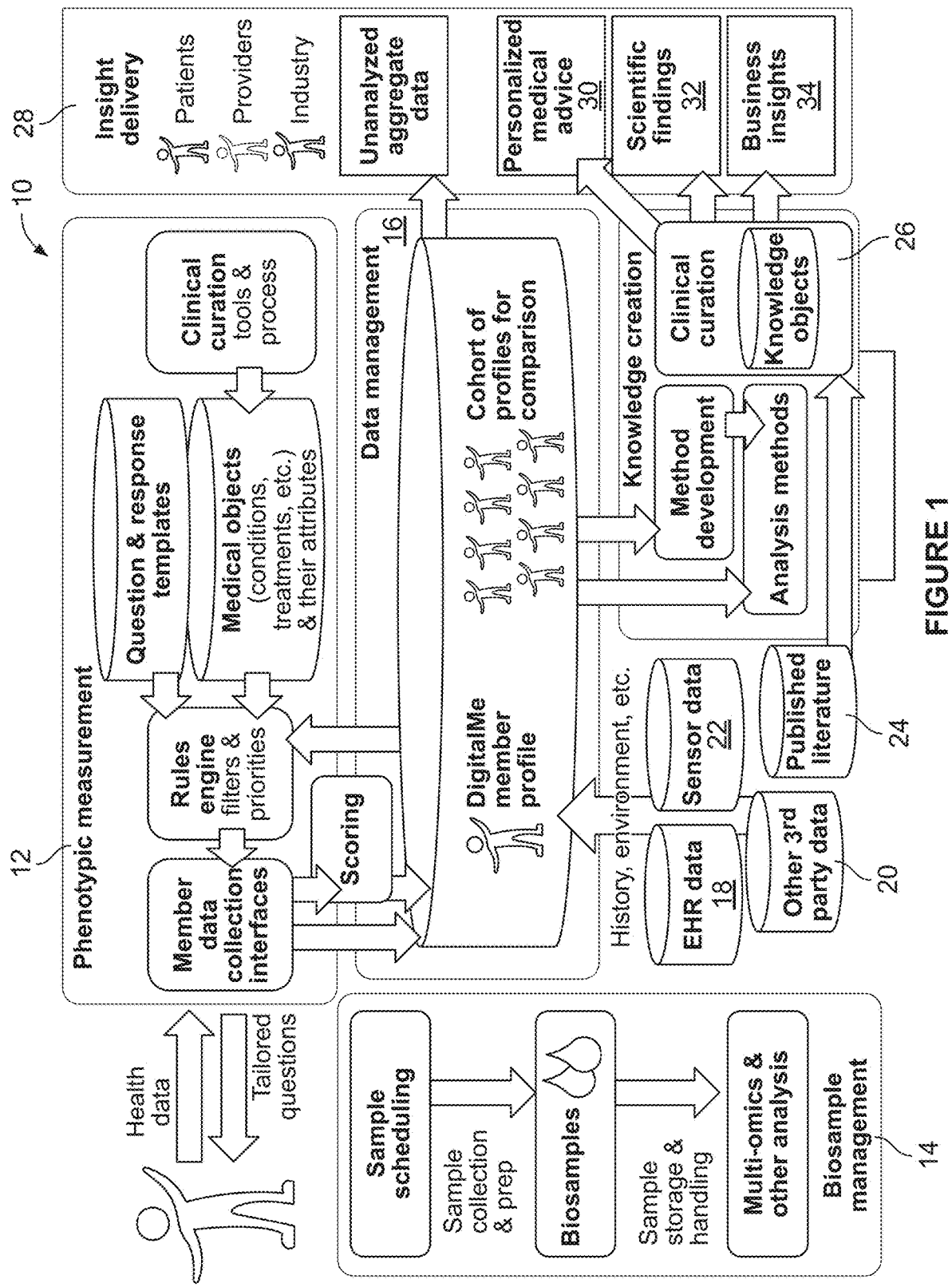
FIG. 1 illustrates an embodiment of a system for collecting, storing, and analyzing biological and medical data.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to systems and methods for collecting, dig and/or storing comprehensive electronic medical data from and about a user, analyzing the data of a plurality of users to find associations, and delivering findings to one or more users or other participants in the system in order to support care decisions or for medical research. In some embodiments, the system can also be involved in collecting and storing biological specimen data for each user in the system, as shown in FIG. 1. In some embodiments, analyzing the data can include various techniques, including applying statistical learning techniques to both types of data to identify possible findings of personal or scientific interest. In some embodiments, delivering information to a user can include communicating multiple of possible decisions to be taken, based in part on a computational knowledge engine.

In some embodiments, the system can be a registry framework whereby individual users can join as members and track information about their health. Data can be collected cross-sectionally and/or longitudinally from a variety of sources such that all the medical data about a user can be collected in a single location to inform medical research and/or individual health or treatment decisions. The data from various data sources can be combined into a patient profile that be used for a variety of functions, including providing the patient with the ability to obtain information about the state of their disease and/or quality of life. This information can be presented to the patient user in a variety of ways through the system. Data sources include but are not limited to electronic health records (EHRs), patient reported outcomes (PROs), biological sample collection and testing, demographic information, hospitalization information, lab tests results, treatment history, primary and/or secondary conditions to allow the patient to include information about other related or unrelated medical conditions, devices, wearables, sensors, and life strategy information. For example, life tracking strategy tracking can be used to allow a patient to enter information relating to quality of life goals, allowing these goals to be used to capture disease progression information. The information can be analyzed in a variety of ways for providing information to the user about their health, information to the user regarding their condition in relation to their health and information provided by other users, and studies that can be run to answer specific questions for patients and to inform changes in health care.

In some embodiments, the sum of a user's data is presented to them as a digitized version of themselves. This can include data about their status (such as surveys and objective labs or device measurements), their interventions (such as treatments, healthcare providers and encounter data, and lifestyle), their environment (such as living situation, relationships, geography, exposures, and healthcare access), and who they are (such as genetics, family history, demographics, and goals).

In some embodiments, the system can also include community-based aspects to allow individual users of the system to connect in one or more communities or through a plurality of information repositories, based on a variety of factors, including illness type and/or life goals related to their illness or their health. The community aspects of the system can allow users to learn from each other about how to manage their disease and/or well being. In some embodiments, this can include various information sources, including news feeds, scientific literature, presentations by experts or healthcare professionals, pose questions to sets or subsets of the community, and/or the ability to search caroled content of interest to a user.

In some embodiments, systems and methods for collecting information about a medical history and/or one or more conditions comprising identifying individuals al risk of or living with specific medical conditions such as but not limited to diseases, A user interface can prompt health information from these individuals or their caregivers such as their diagnoses, treatments, symptoms, patient-reported outcomes, quality of life, ability to perform activities of daily living, developmental milestones, infections, treatment evaluations, side effects, objective laboratory measures, and behaviors, and also incorporate third-party data from smartphones or other connected devices, and/or reports about them from third parties such as caregivers or parents, and/or from their electronic medical records, electronic health records, or insurance claims. This information can be combined with data obtained from a biological sample from the user, including but not limited to blood, saliva, and urine. The user interface can customize the specific information solicited from each individual using machine learning, computerized adaptive testing, item response theory, Rasch analysis, and/or Bayesian statistics. The user interlace can customize a time schedule for soliciting such information in a cadence that is relevant to the nature and progression of their condition(s) and/or treatment(s), drawing upon health information submitted by other individuals like them.

In some embodiments, the user interface can invite individuals to select a preferred time and date to provide a biological sample (e.g. blood, saliva, urine, feces, skin, breath) or a digital sample (e.g. voice, digital photographs, video morphometry). The biological and/or digital sample can yield data relating to genetics, metabolomics, protein signature derived from photoaptemer arrays, antibody-derived immunosignature, and/or other health indicators via machine-learning processing of digital files. The system's data can be analyzed using a database of biological networks derived from a review of the peer-reviewed literature and/or by comparisons to other individuals who have provided similar data.

In some embodiments, a graphical interface can be displayed to an individual to provide recommendations for their health. The graphical interface can be displayed to the individual's parent, caregiver, or trusted third party providing recommendations for their health or to the individual's healthcare provider providing recommendations for their management. The scientific strength of each recommendation is classified according to whether it is a new finding, a known finding from the literature, a replicated finding in the literature, a known test with regulatory approval, or a test undergoing regulatory approval.

In some embodiments, a database query can result in the generation of pre-filled forms for regulatory approval for new scientific findings to be developed into regulatorily-validated tests. A graphical interface can display to the individual soliciting their feedback as to the utility of the health recommendations at a later time. The graphical interface can display to the individual's parent, caregiver, or trusted third party soliciting their feedback as to whether they made the recommended changes and what the consequences were for their health. A database query can request relevant data from a third-party data source such as an EMR, EHR, PHR, or connected device to gather information on whether the individual made recommended charges and what the consequences were for their health. The graphical interlace can be updated with more relevant and stronger health recommendations as new information arises in the literature or from information provided by other individuals using the system. A database query can result in the veneration of pre-filled data export tables to support the creation of scientific publications for submission to the peer-reviewed literature, useful business insights such as drug target discovery, author personalized medical management insights such as the risk of disease or side effects.

As explained above, FIG. 1 illustrates an exemplary embodiment of a system 10 for collecting, storing, and/or analyzing medical data relating to a plurality of system users. In some embodiments, the system 10 includes various information sources about a user, including a phenotype measurement system 12 and a biosample management system 14. All the information gathered from a user from the phenotype measurement system 12, the biosample management system 14, and other outside sources including but not limited to electronic health records (EHR) 18, third-party sources 20, sensor/wearables data 22, and literature 24, is collected and stored within a data management system 16 in a user profile associated with the system. All that information is analyzed, either about an individual user, a subset of users, or all the users in the system, and various types of results are obtained, some of which can be delivered to the user. Those results can vary, and can include information relating to clinical/general knowledge about a disease created by a knowledge creation engine 26 and insights related to one or more user created by an insight delivery, engine 28. Those insights, as will be discussed in more detail below, can include but are not limited to personalized medical advice 30, scientific findings 32, and business insights 34.

Data Types

Figure 2:
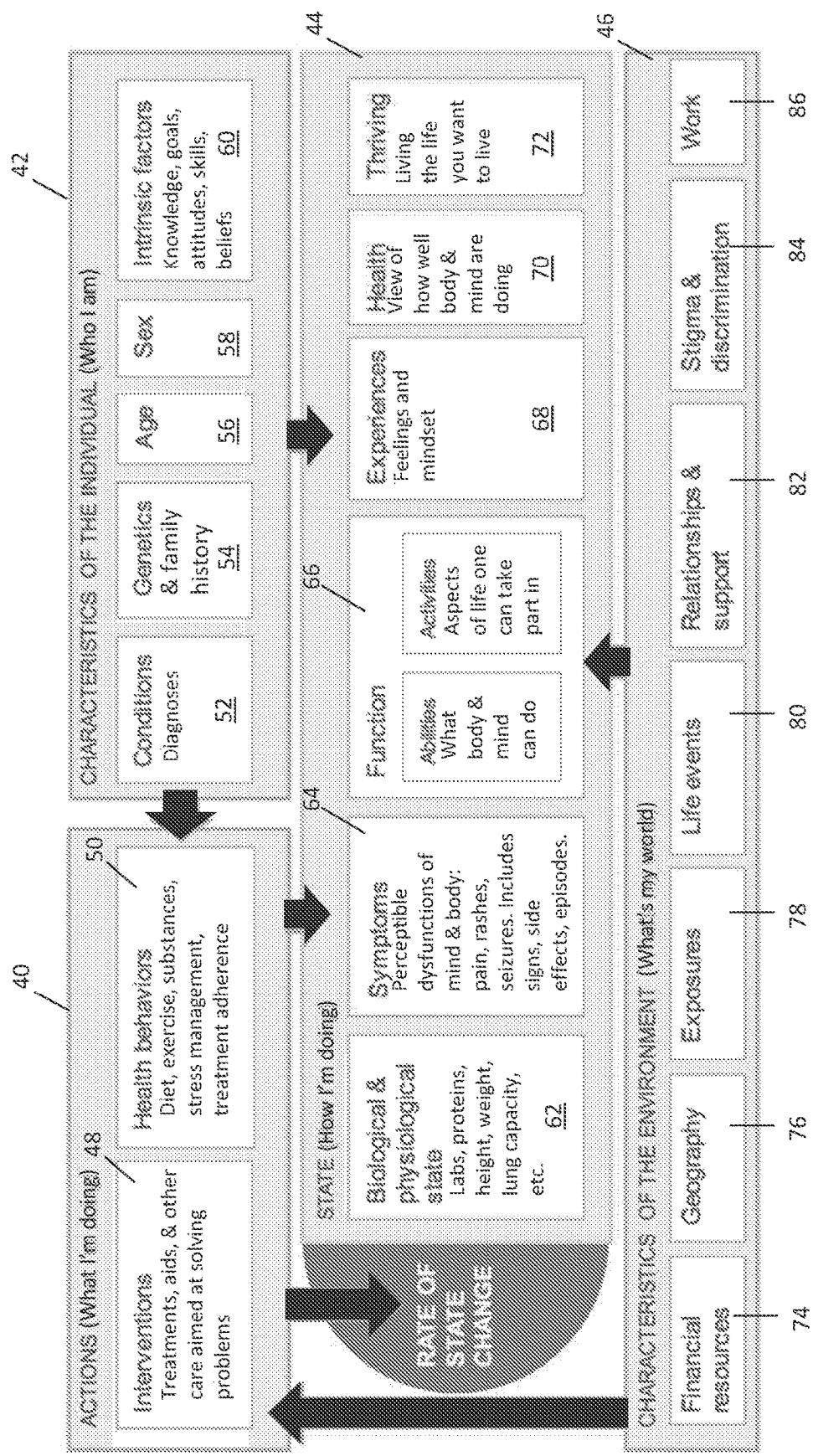
FIG. 2 an embodiment of a plurality of data types utilized by the system.
Figure 3:
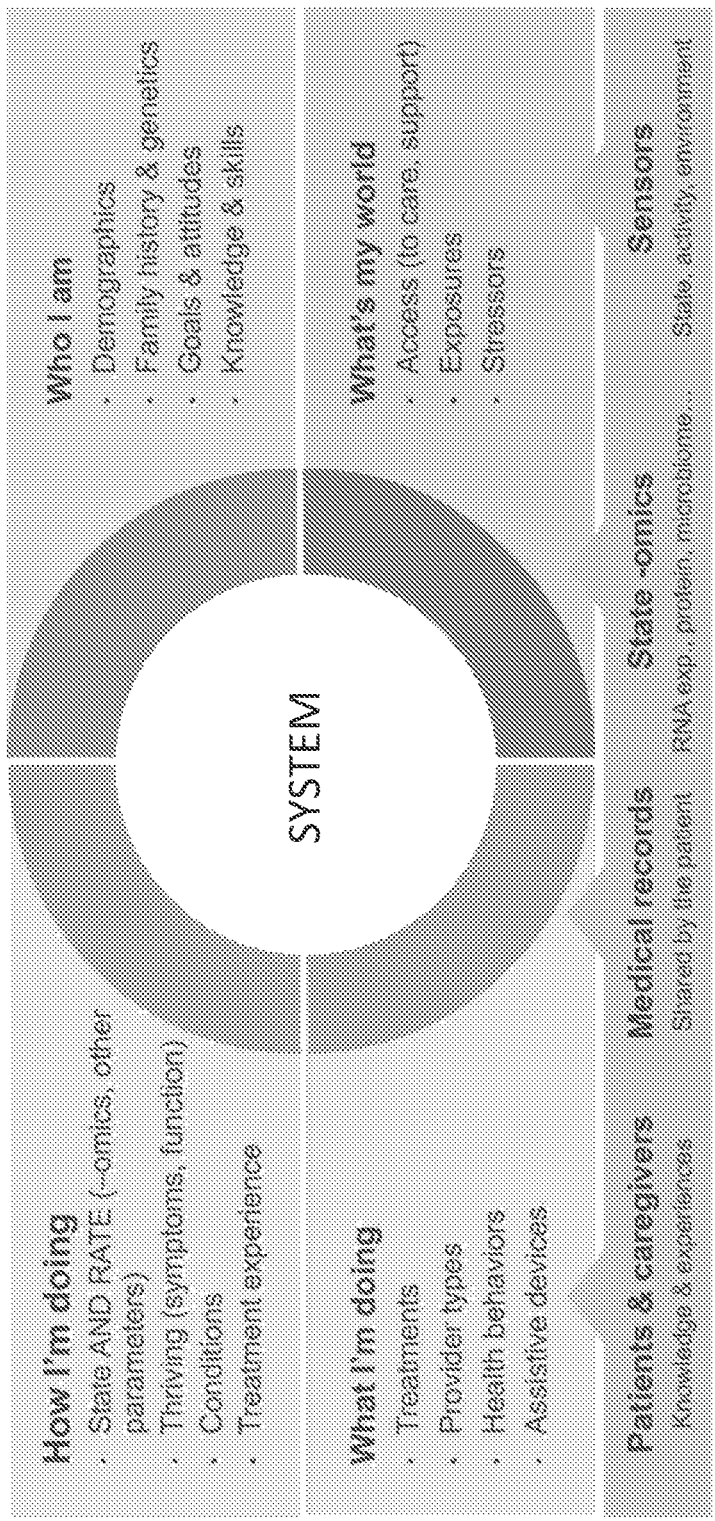
FIG. 3 is an embodiment of a plurality of data types utilized by the system.

Medical data can come from a plurality of sources, including but not limited to experiences and history reported by the individual or caregivers, data digitized from biological samples, electronic medical records, data from personal devices or sensors such as glucose meters, fitness trackers, or mobile phones, healthcare claims databases, and/or environmental and geographical databases. Exemplary embodiment of the sources and type of data that can be utilized by the system are shown in FIG. 2 and FIG. 3. As shown in FIG.

2, in some embodiments sources of information from a user can include actions 40, characteristics of the user 42, state of the user's health 44, and characteristics of the user's environment 46. Actions 40 can include interventions 48 and health behaviors 50. Characteristics of the user 42 can include conditions 52, genetics and family history 54, age 56, sex 58, and intrinsic factors 60. The state of the user 44 can include biological and physiological states 62, symptoms 64, function 66, experiences 68, health information 70, and thriving information 72. Characteristics of the user's environment can include financial resources 74, geography 76, exposures 78, life events 80, relationships 82, discrimination 84, and work 86. As shown in FIG. 3, data types that are sources of data for the system can include how the user is doing, what treatments and behaviors the user is participating in, identification and demographic information relating to the user, and the user's environment. Additional information can come from other people associated with the user, such caregivers, medical records, various "-omics" information, and devices such as sensors.

Phenotype System

The system of FIG. 1 can include a phenotype measurement subsystem that sources subjective status data (including but not limited to symptom severity) and medical history data from users. The system can complete and/or verify history data that can be available from other sources (including but not limited to diagnoses or treatments). The phenotypic measurement subsystem (PMSS) can collect data in a variety of ways. In some embodiments, the PMSS can query members to fill gaps in their historical medical profiles, monitor current status, and detect potential health changes that can trigger other actions by the system (for example, scheduling a biosample collection or alerting a provider to a status change).

In some embodiments, the PMSS can use information already known about each user (for example, diagnoses, treatments, age, or roles such as being a caregiver) to determine what data to collect, and/or at what frequency and priority. For example, the PMSS can construct sets of questions for an individual user to answer (using a set of question templates and/or a database of medical objects) and present those questions to the user at appropriate times. Based on the responses to those questions, the PMSS can make decisions on further actions, including asking additional questions, displaying content to the user (for example, data insights or links to similar users in the system), or triggering actions.

Figure 4:
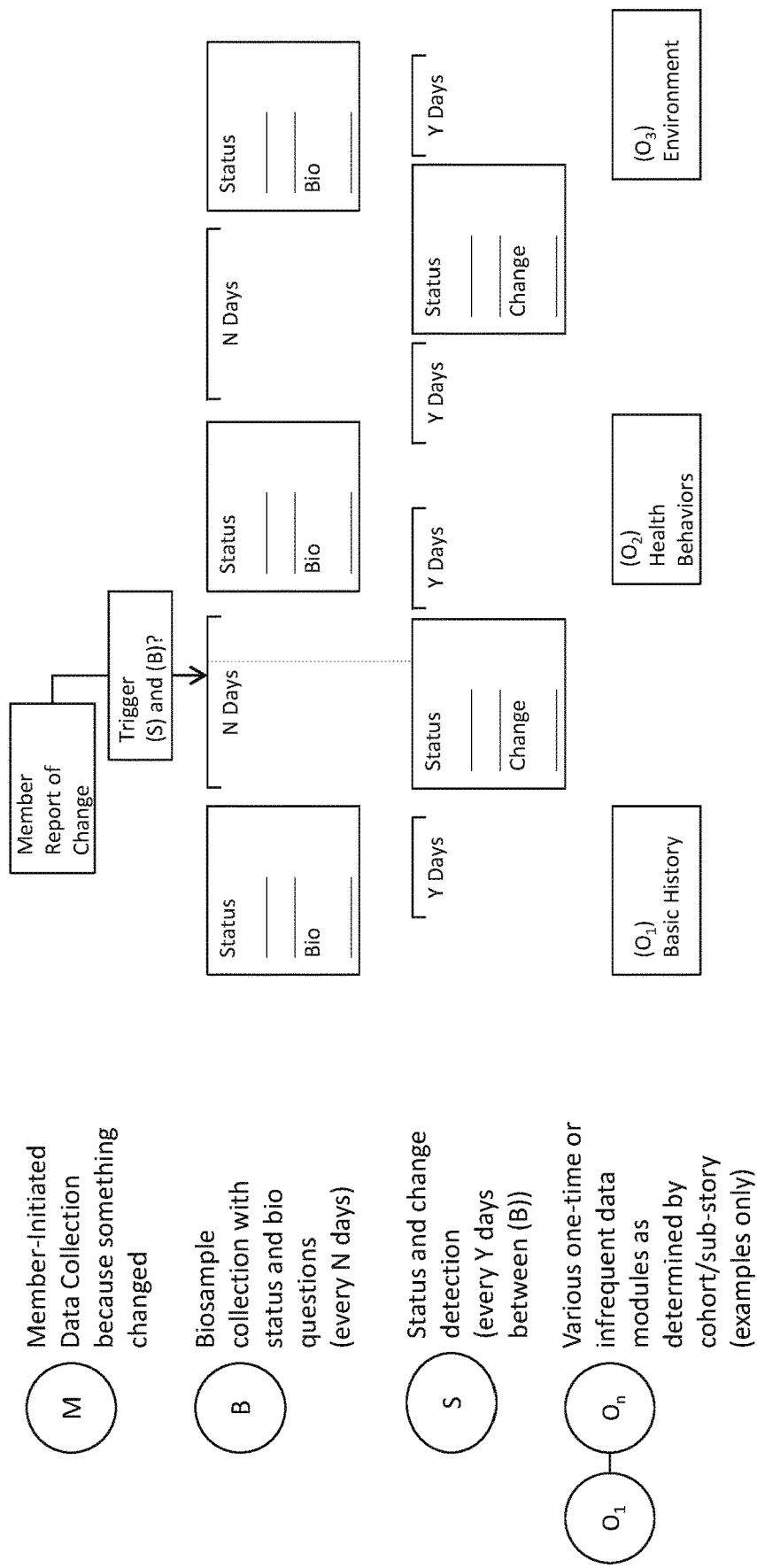
FIG. 4 is exemplary embodiment of a data collection process.

In some embodiments, the PMSS can allow for data entry to be user-initiated, prompted at varying frequencies or at a certain time, or triggered by the data itself. For example, an instance of scheduled or triggered data collection can include questions that fill out the medical history, assess current status (and attempt to detect significant changes in that status), or collect information important at the time of a biosample collection. An exemplary data collection process is illustrated in FIG. 4. Member data collection can be member-initiated, scheduled based on rules specific to a member cohort, or triggered based on member responses or other data (e.g. a large change in weight from a connected scale). The "clock" for scheduled data collection can be reset based on triggered data collection or the timing of biosample collection.

Figure 5B:
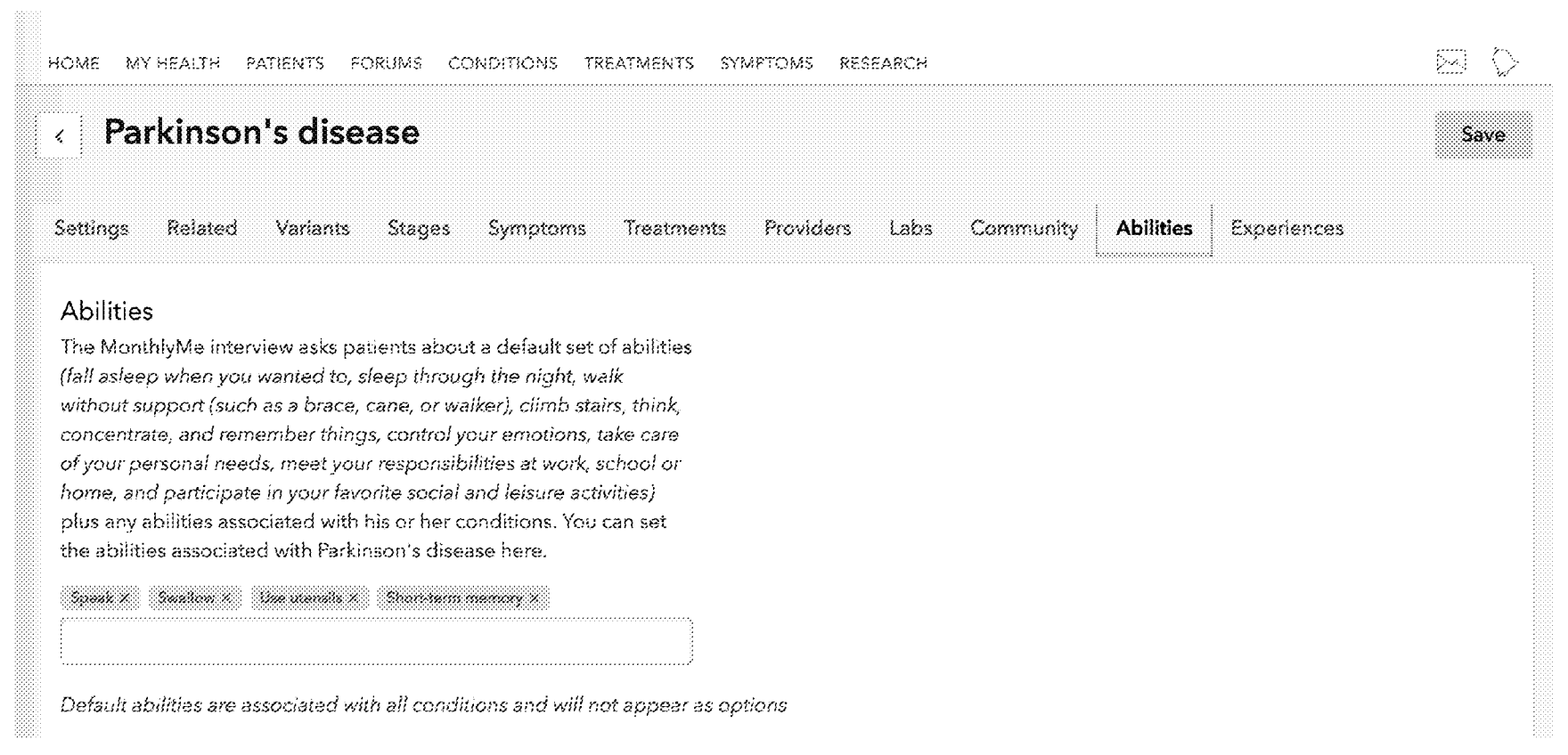
Figure 6A:
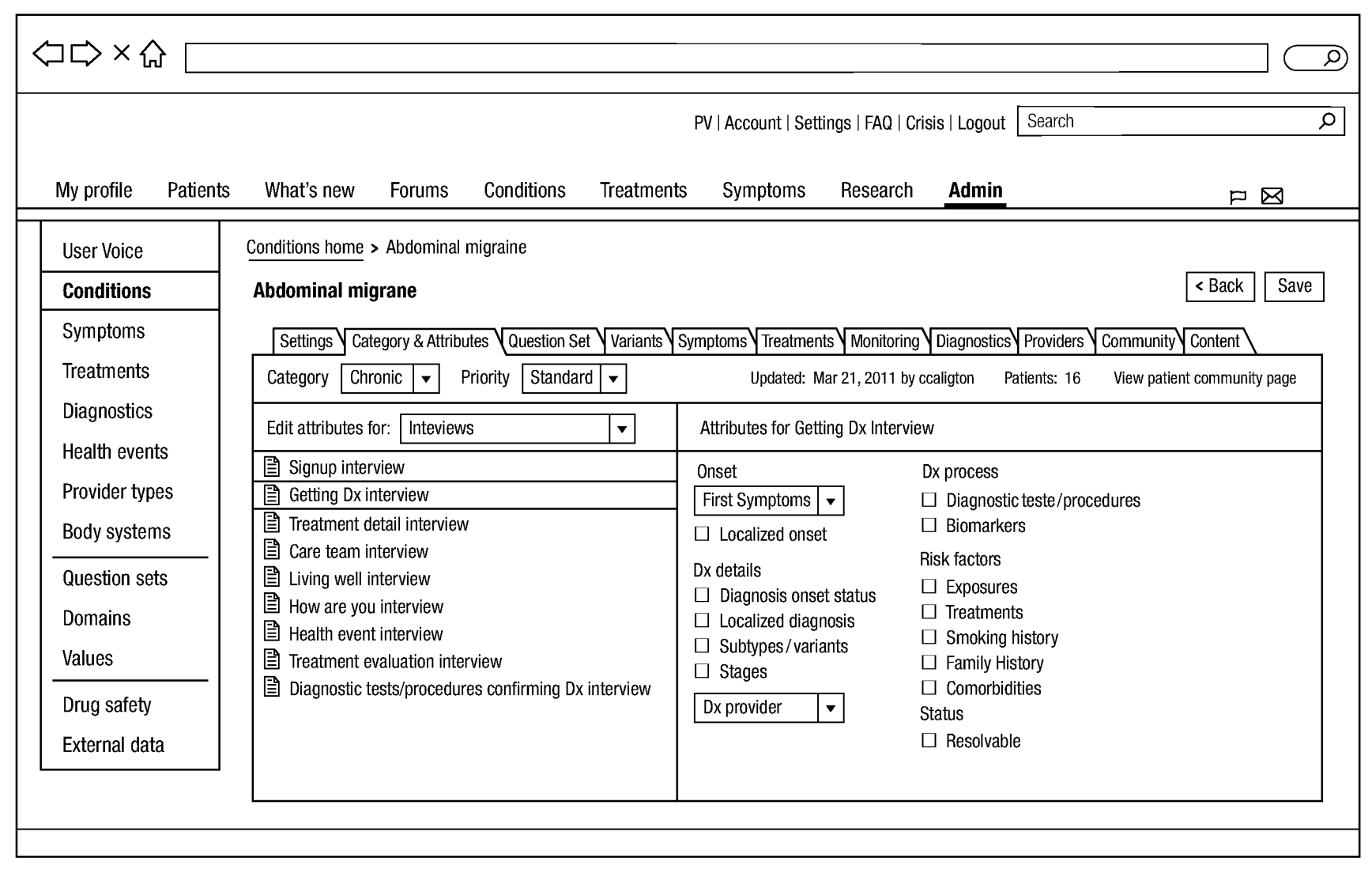
Figure 6D:
Figure 7:
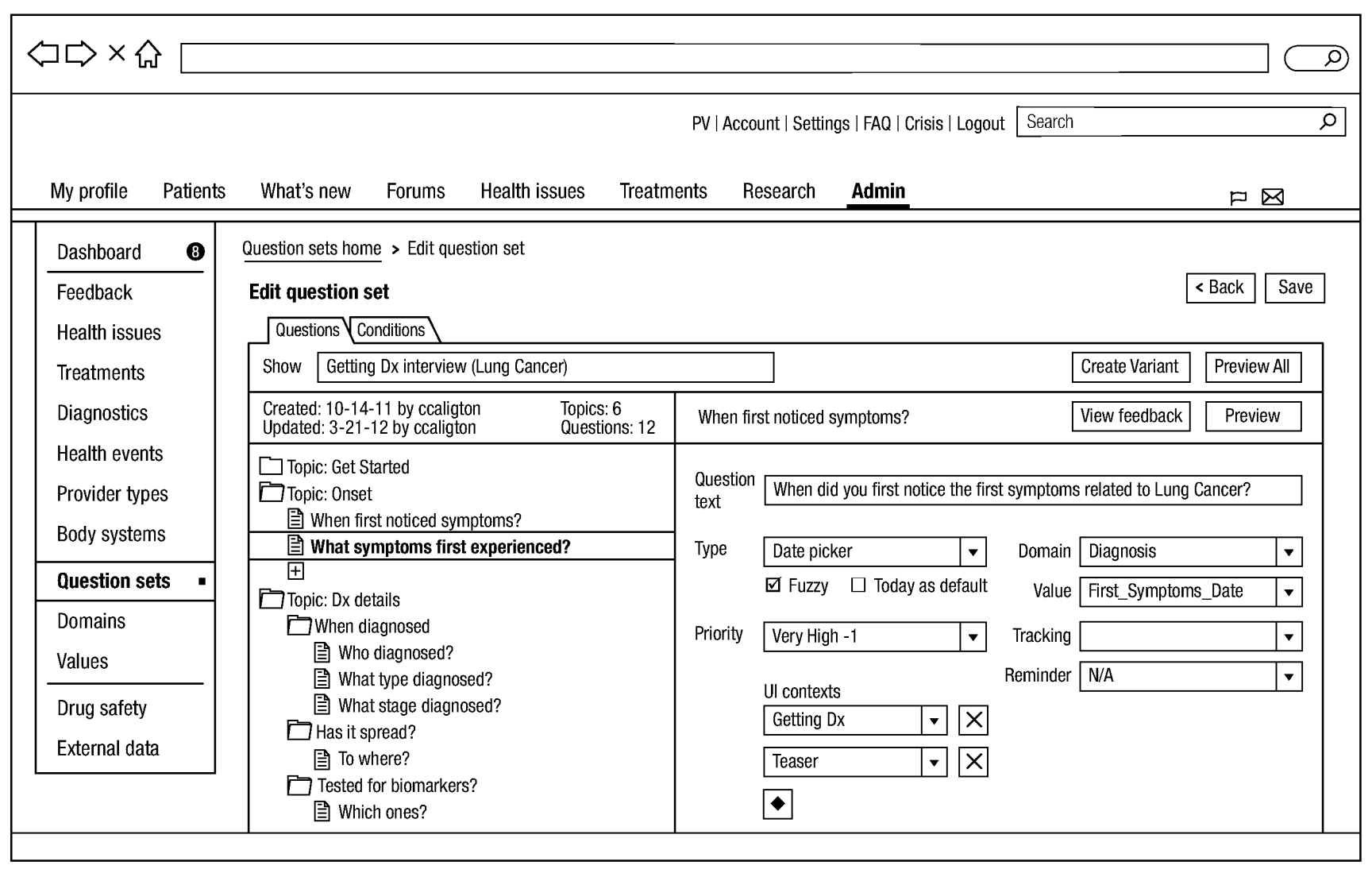
Figure 8E:
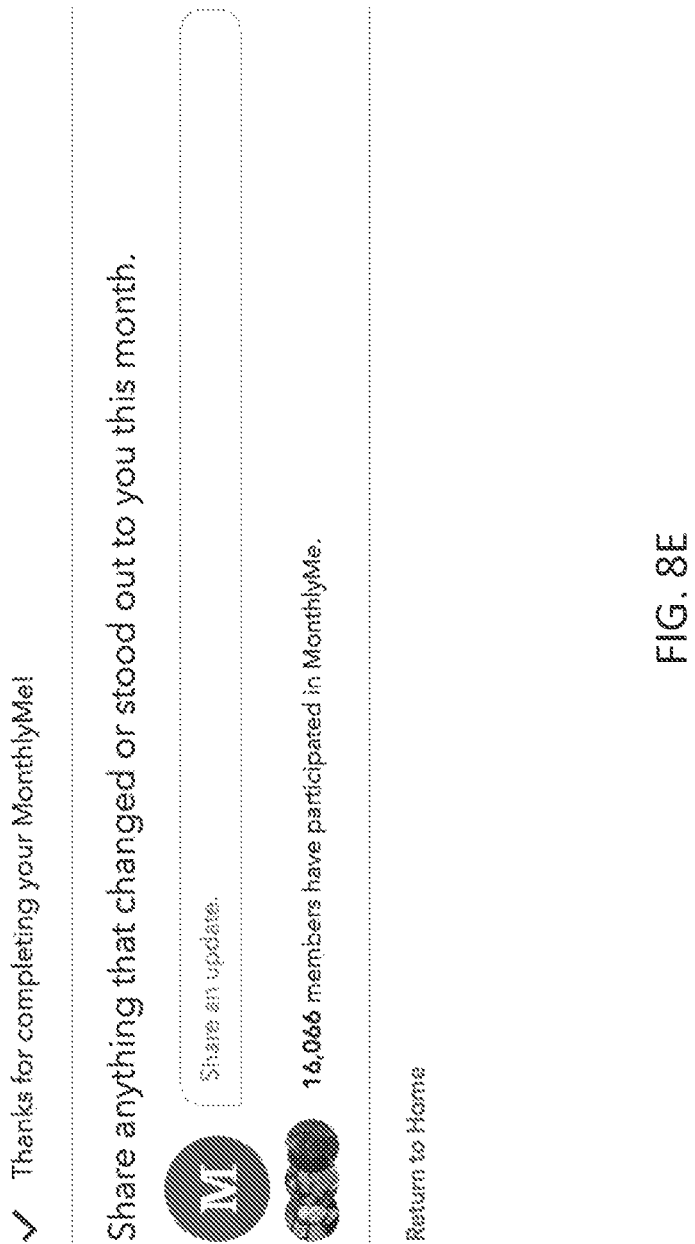
Figure 9:
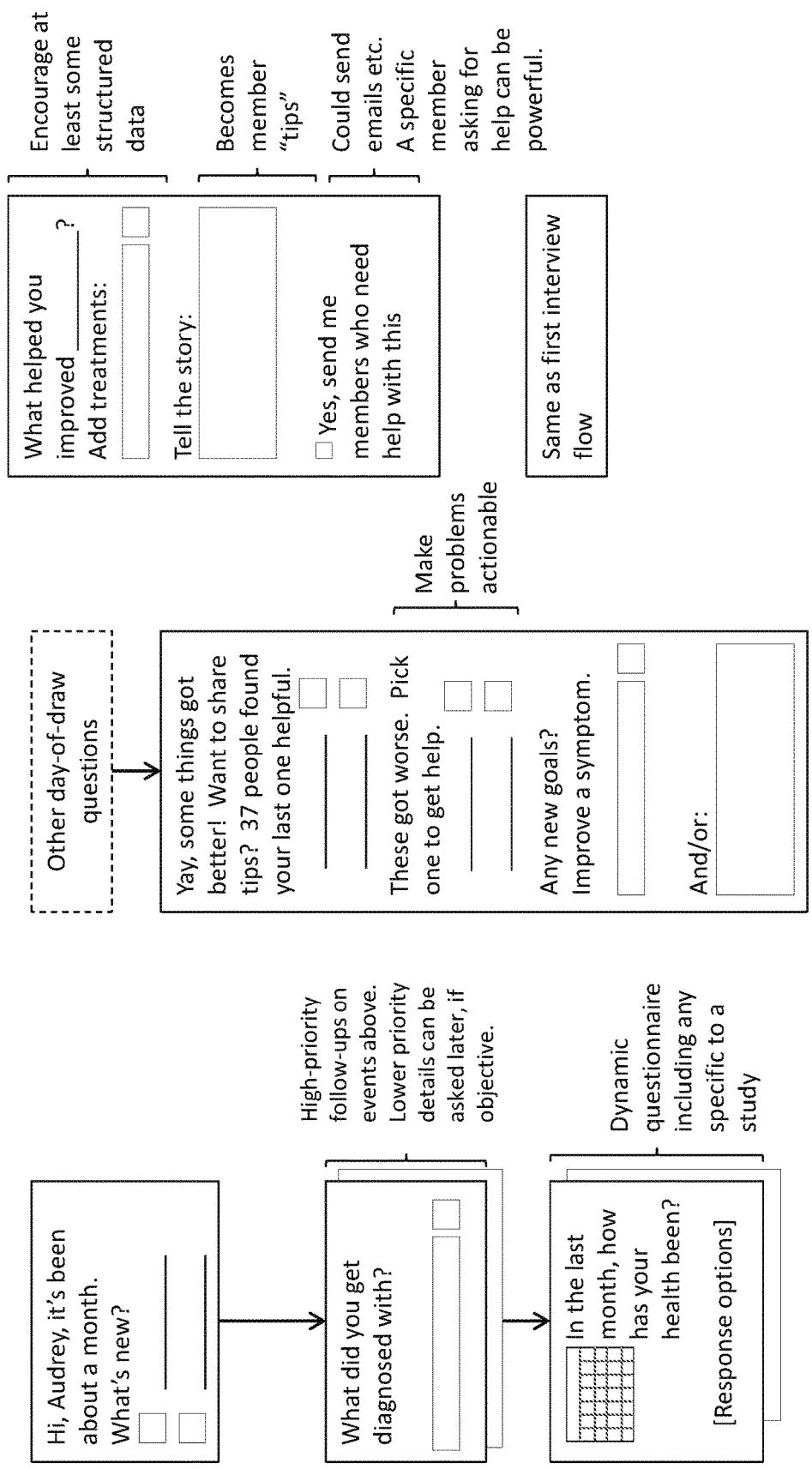
FIG. 9 illustrates an exemplary embodiment of a user interface for collecting data from a user.

Phenotypic data curation tools and processes can be used by the system. In some embodiments, conditions, symptoms, physical and mental abilities, and/or interventions (such as treatments, behaviors, and healthcare provider types) are curated medical objects such that a team of clinicians (such as nurses and pharmacists) are needed to clean up duplicate entries, ensure that the system is up to date with current disease definitions, etc. They can also assign attributes to medical objects that result in questions being asked of users. For example, they can assign a list of common treatments or symptoms for a condition results in users being asked about those, as shown in the exemplary user interface shown in FIG. 5A. FIG. 5A illustrates an interface for customizable lists of systems for a condition. FIG. 5B and FIG. 5C illustrate exemplary embodiments of user interfaces for detailing the ability to customize the abilities and experiences that a user can be prompted about that are associated with a specific condition. In addition, new types of medical objects (such as abilities and experiences) can be assigned and question priorities can be curated. FIG. 6A, FIG. 6B, FIG. 6C, FIG. 6D and FIG. 7 illustrate exemplary embodiments of user interfaces relating the assignment of medical objects. FIG. 6A illustrates an exemplary embodiment of an interface for controlling various interviews/question sets that could be associated with a specific condition. FIG. 6B illustrates an exemplary embodiment of an interface for assigning a version of a "getting diagnosed" interview that is associated with a specific condition. FIG. 6C illustrates an exemplary embodiment of an interface for viewing the various interviews that are available. FIG. 6D illustrates an exemplary embodiment of an interface related to questions and associated visibility rules for the "diagnosis-chronic" interview (for example, "Diagnosis & Onset—Chronic/Cancer"). In addition, the system can use expert curation for medical evidence. FIG. 7 illustrates an exemplary embodiment of an interface for editing a question set for presentation to a user.

Data Collection Interface

Figure 10:
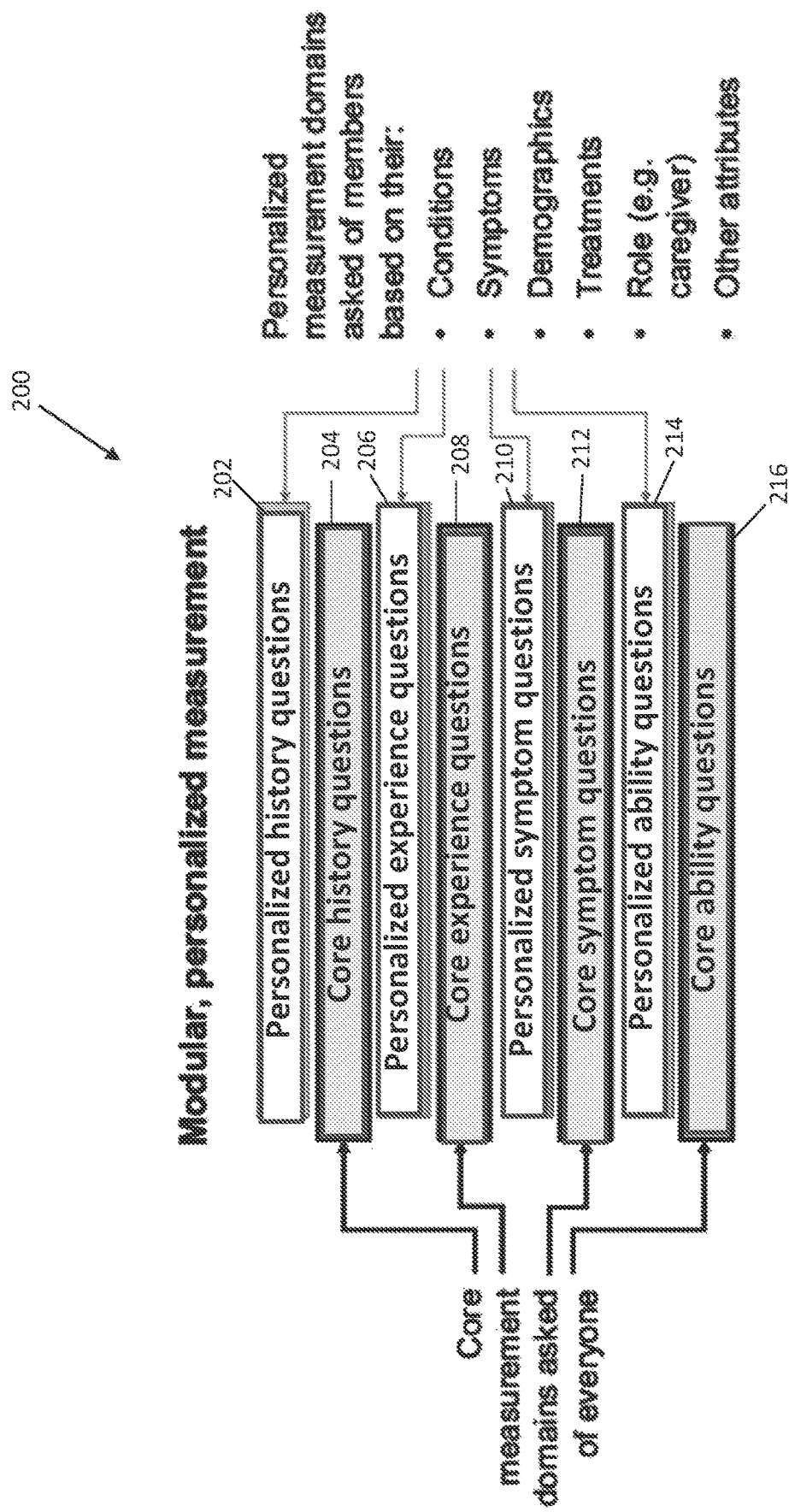
FIG. 10 illustrates an exemplary embodiment of steps for creating a modular measurement that can be tailored to an individual user.

A user can be prompted to provide information to the system using a variety of interfaces and displays. In some embodiments, a user data collection interface can include a historical data entry (via, for example, wizard-style "interviews" and/or static forms) and a longitudinal data entry (via, for example, prompted interviews). Longitudinal data can be prompted at varying intervals, such as daily or monthly, based on the information that needs to be measured. FIG. 8A, FIG. 8B, FIG. 8C, FIG. 8D, FIG. 8E, and FIG. 8F and FIG. 9illustrate exemplary embodiments of a user interface for collecting data from a user. The various data collection interfaces used by the system allow for the personalization of data collection for each user. For example, the system can use information relating to the user's condition and what the user may want to improve to guide the content presented to the user. The results received by the system can be compared to other users and to that user's previous results to provide information back to the user in addition to the questions being presented. When there is an improvement, the system can ask for information relating to how the improvement was achieved in order to share information with other users to allow for both structured and/or anecdotal learning about a medical condition based on user information, In some embodiments, information can be gathered from a user using modular (or personalized) measurement 200 that can be tailored to the individual user, but made up from standardized, or core (and therefore comparable), questions, as explained further in FIG. 10 and Table 1. The modular measurement 200 can include personalized history questions 202, core history questions 204, personalized experience questions 206, core experience questions 208, personalized symptom questions 210, core symptom questions 212, personalized ability questions 214, and core ability questions 216. The core questions can be asked of all the users, while the personalized questions are tailored to each individual user.

TABLE 1

How modularity works, e.g. with symptoms:

| Core Symptoms | Disease-specific symptoms | Patient-specific symptoms |
|---|---|---|
| Everyone is asked about: Pain Fatigue Insomnia Depressed mood Anxious Mood | Assigned in an admin tool, e.g.: Excessive saliva (ALS) _Foot Drop (PD) Brain fog (MS) Paranoia (PTSD) | Selected by patients themselves (from existing list or new entry curated/mapped by health data team) |

All types of questions are potentially modular; not only subjective questions (like symptoms) but also questions about health history, diet, etc. For example, someone with migraines might be asked about light sensitivity as well as whether they consume known trigger foods. Modularity can be important as a normal approach in healthcare is to use narrow clinical definitions of poorly-understood diseases. For example, patients with mood disorders (MDD, bipolar disorder, GAD, PTSD, etc.) can receive multiple diagnoses or changes in their diagnoses (based on, for example, life circumstances, changing diagnostic guidelines, or differing clinical opinions), so when researchers measure patient experience of just one disease with a PRO specific to that disease, insights may be missed about underlying mechanisms and treatment effectiveness. Also, if a patient has two or more related diagnoses, measuring both conditions would mean administering two sets of questions that can have very similar (but not identical) questions. This can be burdensome for the patient and the answers cannot easily be substituted for one another in analysis. In addition, assigning pre-existing modular questions to users with a condition is much faster than crafting a whole new measure.

Figure 11:
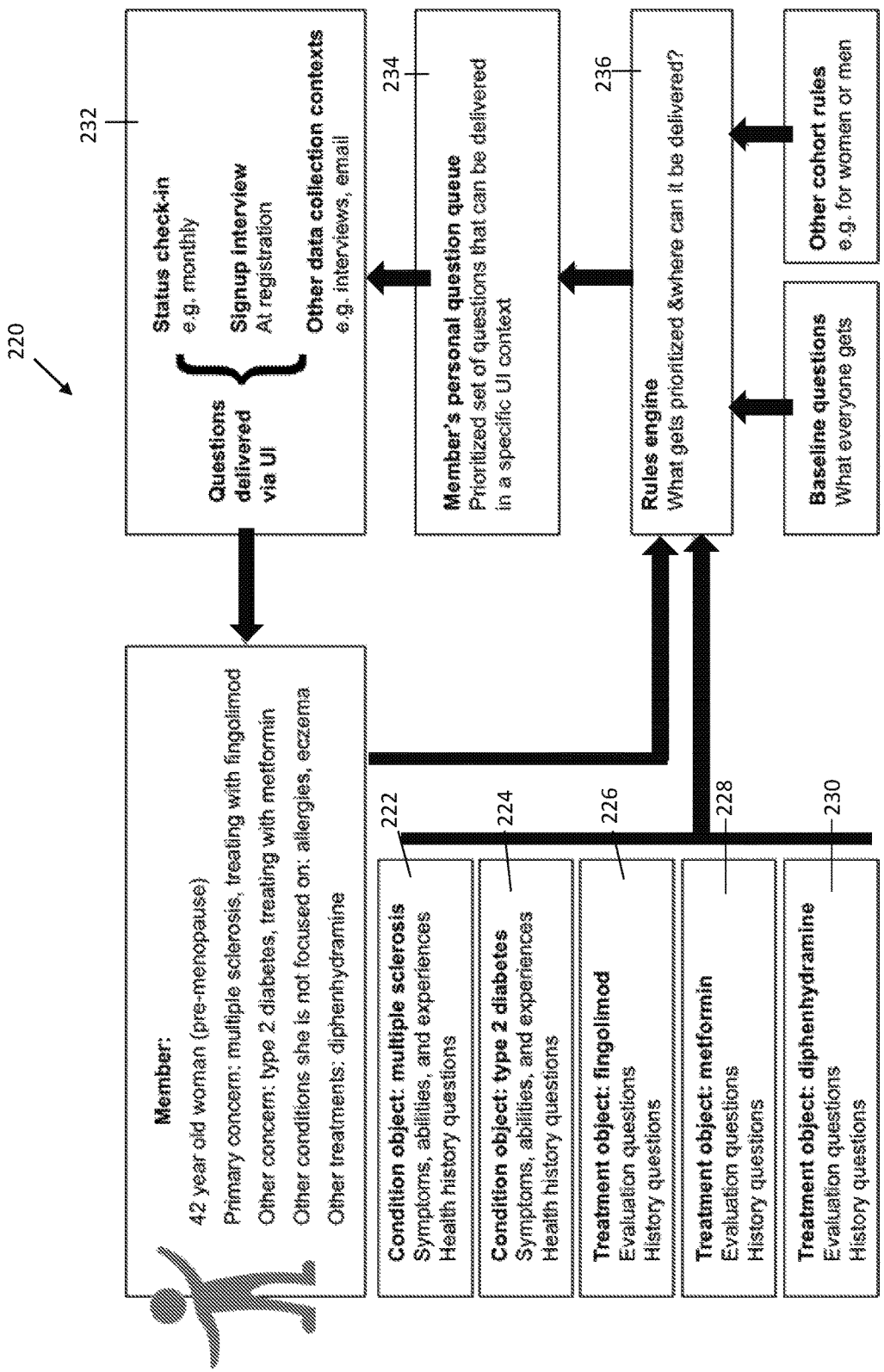
FIG. 11 is an exemplary embodiment of a user interface for generating personalized measures.
Figure 13:
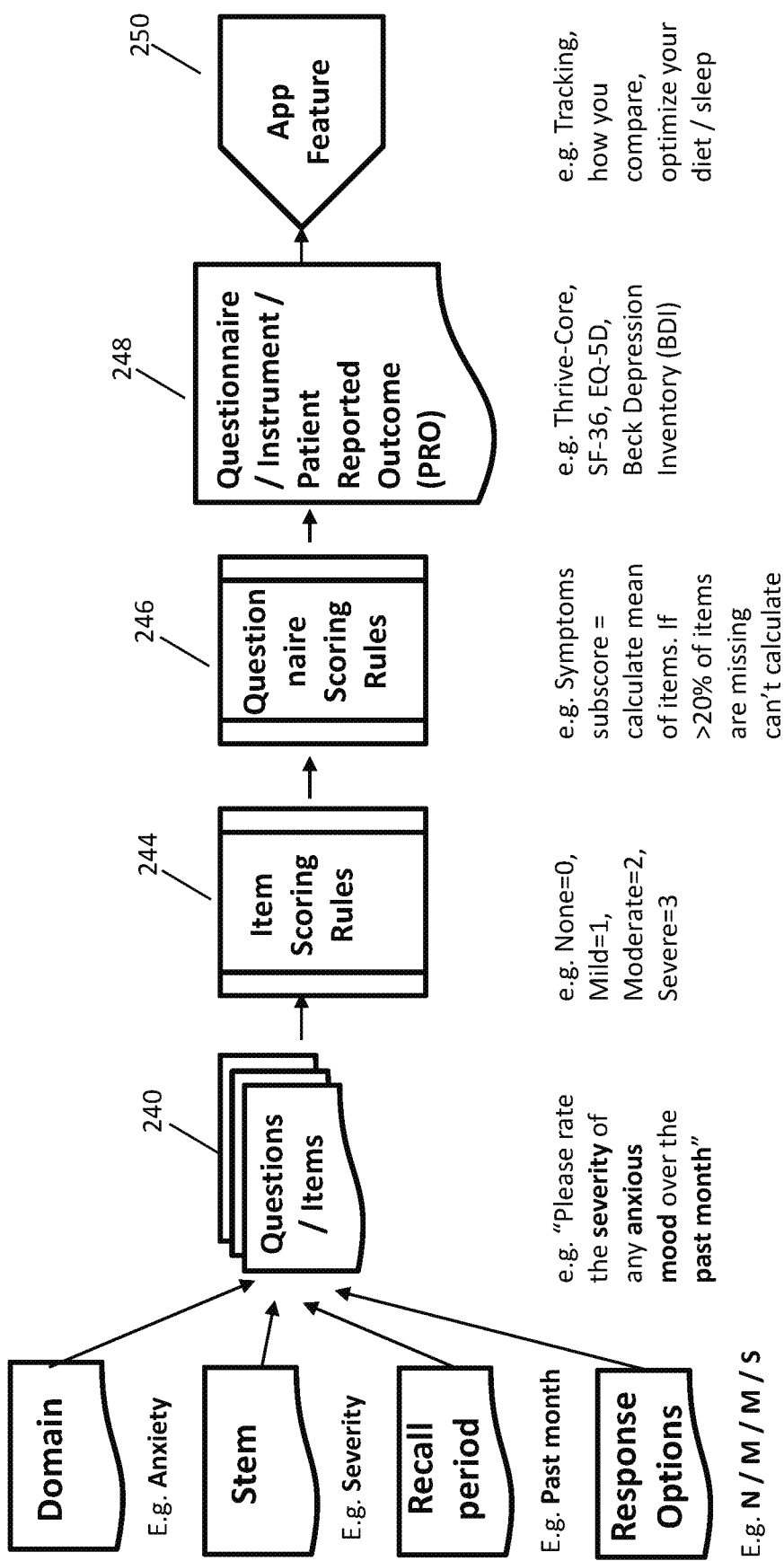
FIG. 13 illustrates an exemplary embodiment of standard questions and responses that can be built as medical objects.

In some embodiments, instead of crafting every question for every disease, personalized measures can be assembled using question templates and medical objects, as shown in the exemplary user interface 220 of FIG. 11. The user interface 220 includes information related to condition objects 222, 224, and treatment objects 226, 228, 230. One or more questionnaires 232 can be delivered to the user via the user interface 220 that is compiled from a queue 234 of questions prioritized for each user by a rules engine 236, A medical object type is a category of thing (or a class, in programming terms: a type of thing that has multiple instances, all with potentially different attributes), such as a condition, symptom, treatment, procedure, provider type, and lab test. A medical object is an instance of that type (e.g. pain, swelling, and redness are all medical objects of the "symptom" type). Each medical object can have a variety of different attributes and relationships assigned to it, including but not limited to other medical objects (e.g. two different conditions may each have different sets of symptoms assigned to them). Different medical object types can be mapped to standardized ontologies for ease of interpretation. FIG. 12 and FIG. 13 illustrate an exemplary embodiment of standard questions and responses that can be built as medical objects. For example, FIG. 12 illustrates various standard questions that can be presented to a user that are associated with database tables of medical objects relating to symptoms, abilities, and experiences that can have a plurality of attributes associated therewith. For example, in FIG. 13 medical objects relating to questions and responses can include questions/items 240, scoring rules 244 related to the questions/items 240, questionnaire scoring rules 246, patient report outcomes 248, and features 250 that relate to tracking symptoms and optimizing treatments.

Question templates include a question stem (which can contain one or more text variables, one of which is usually a medical object type) and a set of response options (which can be hard-coded into the template OR populated from a table based on the value of the text variable).

Below are non-limiting examples of exemplary embodiments of question templates:

A question template for "one-month symptom severity" with hard-coded response options:
Over the last month, please rate the severity of any <symptom>: none/mild/moderate/severe/stop asking me this A question template for "diagnosing provider type" with variable response options:
What kind of healthcare provider first diagnosed you with <condition>?<list of provider types associated with the condition>

The question template or the question template plus the medical object result in a data element, such as question template "30-day symptom severity"+medical object "pain"=data element "30 day pain severity." Some data elements can be populated by sources other than answering questions (e.g. "weight" could be populated by a smart scale or by a patient answering a question it can be considered the same data element, while preserving the provenance of where it came from).

Rules Engine for Dynamic Questionnaires

In some embodiments, a rules engine can be used to determine the questions each user sees and when, based on user attributes including but not limited to demographics, diagnoses, current or past treatments, or membership in a specific study. For example, the attributes can be medical objects, which can also have questions assigned to them. Several examples are shown in Table 2.

TABLE 2

| If member... | They see questions about... | Other rules |
|---|---|---|
| Is female | Pregnancy status - at every biosample First period --- once | Skip pregnancy if post-menopausal |
| Has asthma | Smoking | Higher priority than for other members |
| Has epilepsy | Frequency and severity of seizures - longitudinally e.g. monthly | Asked monthly for most members, but weekly for members on drug X |
| Is taking drug X | Side effects of drug X | Asked sooner if high-priority drug; may never be asked if low priority |

The attributes of a question template can determine which interface contexts it appears in. For example, a multiple-choice question that can be answered with a click could be asked directly in email, but a question requiring numeric entry cannot. Questions about treatments would not appear in the middle of a set of questions about symptoms.

The various rules can be used to create an individualized question queue for each user, winch determines winch questions are asked sooner and which are asked later. This allows the system to ask for the highest-priority data first. For example, questions about a member's treatments might be prioritized as follows: 1. Complete list of all current treatments, 2. Dosage information for current disease-modifying treatments, 3. Complete list of previous disease-modifying treatments, 4. Dosage information for other current treatments, 5. Patient evaluation of current disease-modifying treatments, 6. Patient evaluation of other current treatments, and then 7. Dosage information for other past treatments. This prioritization can change based on user entries at any time.

An exemplary embodiment of a dynamically-created questionnaires relating to the symptoms associated with lupus, Parkinson's, and psoriasis are shown in FIG. 14 and FIG. 15. An exemplary embodiment illustrating the types of questions asked of a user in a dynamically-created questionnaire is shown in Table 3. The questions shown in Table 3 can be used with any illness to assess the overall health of a patient.

The various biosamples can be collected in a variety of ways, including through the user of third-party services. In some embodiments, sample collection scheduling can be done on a regular schedule and/or using state change detection, explained in further detail below, to trigger biosample collection at biologically interesting times. A sample can be prepped, multi-omics can be applied, and the sample can be storage and management by the system or a third party storage.

In order to collect biosamples al the most critical times, the phenotypic measurement subsystem can be configured to detect potential state changes in a variety of ways, any of which can trigger a request to schedule a biosample collection. The criteria for triggering the collection can vary based a variety of factors, including user attributes and compo-

TABLE 3

Figure 16:
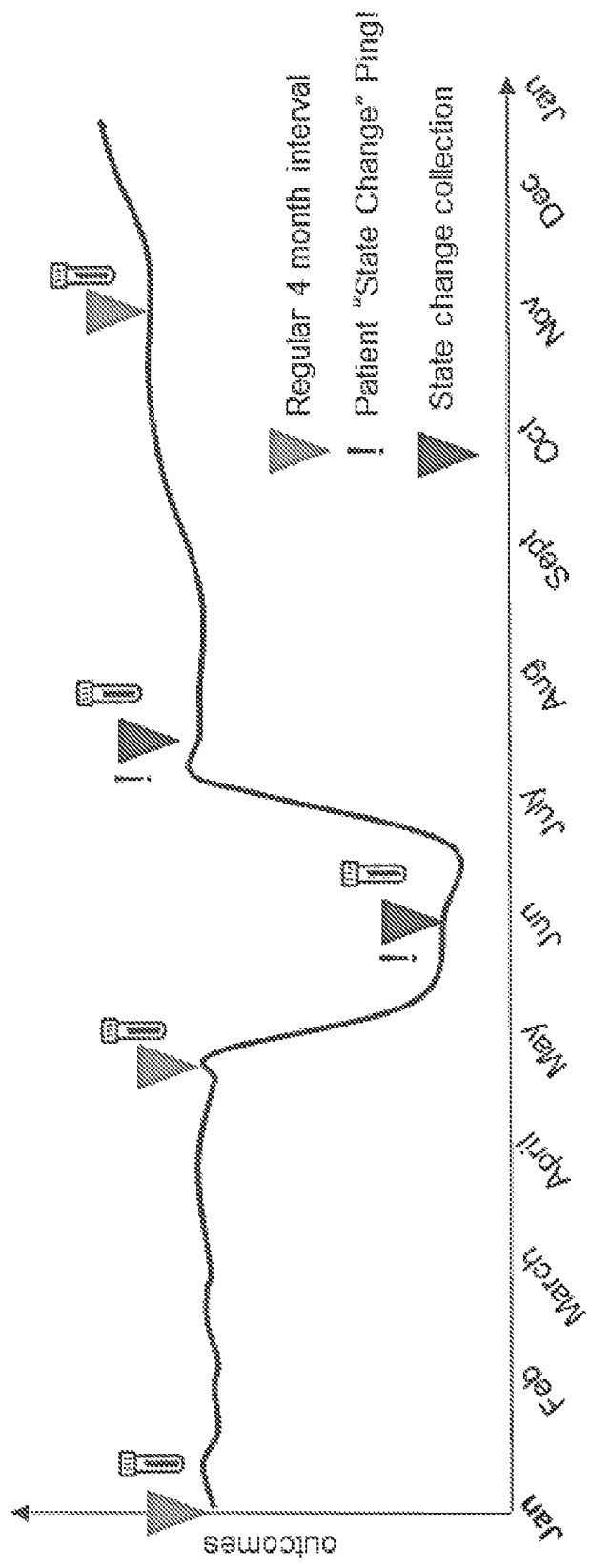
FIG. 16 is an exemplary graph of the timing of biological sample collections based on set intervals and state changes

1. Over the last month, how has your health been?
   Excellent    Very good    Good    Fair
2. Over the last month, how has your health changed?
   Much    Better    A little    About the    A little    Worse    Much
   better              better      same         worse                worse
3. Over the last month, how much has your <condition name> affected your life?
   Not at all                A little                    Some
4. Please rate the severity of any pain over the last month.
   None        Mild            Moderate            Severe
5. Please rate the severity of any depressed mood over the last month.
   None        Mild            Moderate            Severe
6. Please rate the severity of any anxious mood over the last month.
   None        Mild            Moderate            Severe
7. Please rate the severity of any fatigue over the last month.
   None        Mild            Moderate            Severe
8. Please rate the severity of any stress over the last month.
   None        Mild            Moderate            Severe
9. Over the last month, how well could you fall asleep when you wanted to?
   Extremely well    Very well    Fairly well    Poorly    Not at all
10. Over the last month, how well could you sleep through the night?
    Extremely well    Very well    Fairly well    Poorly    Not at all
11. Over the last month, how well could you walk without support (such as a brace, cane, or walker)?
    Extremely well    Very well    Fairly well    Poorly    Not at all
12. Over the last month, how well could you climb stairs?
    Extremely well    Very well    Fairly well    Poorly    Not at all
13. Over the last month, how well could you think, concentrate, and remember things?
    Extremely well    Very well    Fairly well    Poorly    Not at all
14. Over the last month, how well could you control your emotions?
    Extremely well    Very well    Fairly well    Poorly    Not at all
15. Over the last month, how well could you take care of your personal needs?
    Extremely well    Very well    Fairly well    Poorly    Not at all
16. Over the last month, how well could you meet your responsibilities at work, school or home?
    Extremely well    Very well    Fairly well    Poorly    Not at all
17. Over the last month, how well could you participate in your favorite social and leisure activities?
    Extremely well    Very well    Fairly well    Poorly    Not at all
18. Over the last month, how often did you feel good about yourself?
    All of the time    Most of the time    Some of the time
19. Over the last month, how often did you find meaning in your life?
    All of the time    Most of the time    Some of the time
20. Over the last month, how often did you feel connected to others?
    All of the time    Most of the time    Some of the time    None of the time
21. Over the last month, how often did you feel able to live the life you wanted?
    All of the time    Most of the time    Some of the time    None of the time Biological Sample Collection and State Changes The system also includes a subsystem to organize and arrange for the collection and/or storage of biological samples from the users to provide another source of information relating to the medical and biological makeup of a user in some embodiments, each user of the system has a profile that includes a combination of user experiences, biology, and/or third party data relating to the user that all reference each other. The profile can also track user consent relating to the data, and can have information relating to access controls as well.

nents of the medical condition related to the user. FIG. 16 illustrates an exemplary graph over time of the timing of biological sample collections based on set intervals and state changes.

State changes can be related to information reported from users relating to certain changes, including hospitalizations, changes in various health status scores, answers to specific questions (e.g. a user can be experiencing a flare or relapse, reports changing a medication dose, or reports some other significant health event), changes in wearable/sensor data (e.g. scale weight), and/or events from other third-party data sources (e.g. a hospitalization, new treatment start, or shift in lab values is recorded in the EHR).

Table 4, Table 5 and Table 6 illustrate examples of state change decision rules, in which there is a specified minimum interval between biosample collections, and any condition-specific rules override general rules. Similar state change rules can be generated for any disease or condition, including but not limited to multiple sclerosis, ALS, Parkinson's disease, Alzheimer's disease, systemic lupus erythematosus, diabetes, neurological disorders, cancer, and other diseases, disorders, and conditions.

TABLE 4

General Rules

| State change | Origin of data | Rule (content and time delta) | Collect blood, time frame and other instructions |
|---|---|---|---|
| Pregnancy | Profile: Collection C: CU update_10 == 1 "What's new with your health since the last time you updated? Please select all that apply." | Once it changes from NO-->ES Patient may have more than one pregnancy throughout the registry, but each pregnancy is one SC | Yes, always. No time limit. Ideally in time to get two collections during pregnancy |
| Planning on changing disease- modifying treatment (DMT) | Profile: Report from prompted treatments page for collection C changes from those recorded with last collection C or collection B - Unprompted addition of DMT to profile data C: Q38 tx_change == 1 "Are you planning to stop or start any treatments in the next month?", free text content of tx_explain "It may be important to get a blood sample before or after your change." | Select YES | If previous collection can be used as baseline, this one can be skipped. 1)Last collection more than 60 days--> yes, collect before change of medication 2)Last collection less than 60 days → no |
| Removal of DMT | Profile C: Q39 | If DMT is no longer added when compared to last report | Yes, more than 30 days AND no addition of DMT If switching (add at the same time as removing) --> use addition of DMT rule |
| Addition of DMT | Profile C: Q39 | If a new DMT is added (not present in the last report AND present in current report) | If patient planning on the change → follow "Planning on changing DMT" rule If already started taking → record fact and make sure next collection happens >30 days after starting taking |
| Change diagnosis or a subtype of a diagnosis (disease classification/variant) | Profile: C: Q1 ( Changed diagnosis (or the subtype of a diagnosis) If update_2 == 1 give bioinf content of dx_change | Select 'Changed diagnosis (or the subtype of a diagnosis)' | No time sensitivity, at earliest convenience (<21 days) |
| New diagnosis | Profile: C: Q1 (New diagnosis) if update _? == 1, give bioinf content of new_dx | Select 'New diagnosis' | No time sensitivity, at earliest convenience (<21 days) |

TABLE 4-continued

General Rules

| State change | Origin of data | Rule (content and time delta) | Collect blood, time frame and other instructions |
| --- | --- | --- | --- |
| New symptom started or new location for an existing symptom | Profile: medical.user_symptom_history records new symptom added with severity > 0 OR existing symptom that was always scored at 0 is now > 0 C: Q1 (New location for an existing symptom; New symptom started) If update_8 == 1 give bioinf content of sx_location, sx_loc_date and sx_loc_still OR If update_9 == 1 give bioinf content of new_sx, sx_date, new_sx_still | Select "New symptom started" or "New location for an existing symptom" | It has stopped-->NO It has lasted more than 3 days AND still ongoing-->YES, within 5 days If less than 3 days AND patient believes it's related to disease-->YES, within 5 days If less than 3 days AND not sure it's related to disease AND ongoing--> contact patient again after 3d--> if it's ongoing--> yes, within 5d Fever-->patient believe it's related to disease-->yes, within 5 days |
| Patient is having a relapse or flare | Profile: C: Q1, 1c ( (flare or relapse) if update_5 == 1, send bioinf content of flare_date | Select "Flare or relapse" | Yes, within 5 days, regardless of when it started. Less than 3 would be ideal |
| Big change in health | C: Q1, 1i if update_14 == 1, send bioinf content of health_change | Select "Something else you think is a big change in your health" | Probably yes, within 7 days but decision based on a case-by-case scenario |
| Change in Thrive (Perceived health is worse/much worse or better/much better) | C: health_ch (Over the last month, how has your health changed?) = 1,2(much worse/worse) or = 7,6 (much better/better) if 7 provide response to good_change, if 1 provide response to bad_change | Select "Much better/Better" or "Much worse/Worse" | Probably yes, within 7 days but decision based on open text content |
| Patient is worsening, gaining symptoms (not only symptom | Profile: C:whoosh, will all be detected from patientbase | Profile: Removal of a symptom, report which symptom was added to bioinf Change in symptom compared to last report <= -2 C: If change between current severity and last month's severity <= -2 OR change between current tx_se and last month's tx_se <= -2 (None to Moderate or Severe, Mild to Severe) | Yes → within 14 days |

TABLE 4-continued

General Rules

| State change | Origin of data | Rule (content and time delta) | Collect blood, time frame and other instructions |
|---|---|---|---|
| Patient is improving, losing symptoms | Profile: C: whoosh, will all be detected from patientbase | Profile: Medical.user_symptom_history symptom score stays at 0 for <duration> or removed from profile and once had a recorded score > 0<br>C:<br>If change between current severity and last month's severity>= 2<br>OR<br>change between current tx_se and last month's tx_se>= 2 | Yes → within 14 days |
| Hospital stay/ER visit | Profile: C: Q1, if update_6 == 1 OR update_3 == 1, give bioinf content of hospital, er_visit and update_12 | Select "Emergency room visit" or "hospital stay" | If visit was related to disease AND situation doesn't fall under other rule → yes, within 7 days from discharge Regardless of the medication, but should make sure we annotate all tx used during stay and ongoing If any reason to believe it isn't related to the disease (heart attack, asthma, broken bone, sore throat, bleeding . . . ) --> NO Opportunistic infections (aspiration pneumonitis, bed sores/pressure sores, ) → NO |

TABLE 5

AMYOTROPHIC LATERAL SCLEROSIS STATE CHANGE

| State change | Origin of data | Rule (content and time delta) | Collect blood, time frame and other instructions |
|---|---|---|---|
| ALS-FRS | Profile C | >1 point increase (reverse) OR <2 points decrease (worsening) sustained over last 60 days | At patient convenience (<21 days) |
| Forced vital capacity/Forced vital capacity percentage | Profile | Change of 7% when compared to previous measurement OR to last 30 days | Yes, within 7 days |
| Addition of ventilator | (ALSFRS - Respiratory insufficiency) Profile C: | Change any option with BiPAP or mechanical ventilation | Yes, at earliest convenience (<21 days) |

TABLE 5-continued

AMYOTROPHIC LATERAL SCLEROSIS STATE CHANGE

| State change | Origin of data | Rule (content and time delta) | Collect blood, time frame and other instructions |
|---|---|---|---|
| Addition of wheelchair | Breathe_aide_1 == 1 OR (whatever mechanical ventilation) and was not 1 on last C (ALSFRS - Walking) Profile C: devices_6 == 1 and was not checked on last C | Change to Nonambulatory functional movement | Yes, at earliest convenience (<21 days) |
| Addition of feeding tube | (ALSFRS - Feeding) Profile C: nutrition_1 == 1 or nutrition_2 == 2 | Change to needs supplemental feeding tube or NPO | Yes, at earliest convenience (<21 days) |
| Removal of DMT | Profile C: Q39 | If DMT is no longer added when compared to last report | Follow general rule |
| Addition of DMT | Profile C: Q39 | If a new DMT is added (not present in the last report AND present in current report) | Follow general rule |
| Hospital stay/ER visit | Profile C: Q1 | Select "Emergency room visit" or Hospital stay | Complications that indicate worsening of disease -->YES, within 7d from discharge Regardless if ongoing or not Regardless of treatment Examples: Ventilatory failure Incontinence Sialorrhea Limb stiffness Thickened secretion Depression and anxiety Pain Cramps Sleeping problems Loss of appetite Sleeping problems Loss of appetite OTHER COMPLICATIONS Respiratory support complications -- > NO Tracheostomy complications Aspiration pneumonia Barotrauma/hypotension related to intrathoracic pressure Sinusitis Percutaneous endoscopic gastrostomy complications → NO Peritonitis Beds sore/pressure sores Hemorrhage Tube migration and the buried bumper syndrome Gastrocolocutaneous fistula Wound infection and necrotizing fasciitis Inadvertent removal of PEG tube |

TABLE 6

EXAMPLE MEDICATIONS RELEVANT TO DETECTING STATE CHANGE

| Disease | Medication | ID |
|---|---|---|
| ALS | Riluzole | |
| ALS | Baclofen | |
| MS | Alemtuzumab (Lemtrada) | |
| | Daclizumab (Zinbryta, Zenapax)) | |
| | Dimethyl fumarate (Tecfidera) | |
| | Fingolimod (Gilenya) | |
| | Glatiramer acetate (Copaxone, Glatopa) | |
| | Interferon beta-la IM Injection (Avonex) | |
| | Interferon beta-la SubQ Injection (Rebif) | |
| | Interferon beta-lb SubQ Injection (Betaseron, Extavia) | |
| | Natalizumab (Tysabri, Antegren) | |
| | Peginterferon beta-la (Plegridy) | |
| | Teriflunomide (Aubagio | |
| PD | Amantadine | |
| | Carbidopa-Entacapone-Levodopa | |
| | Carbidopa-Levodopa | |
| | Deep Brain Stimulation (DBS) | |
| | Entacapone | |
| | Pramipexole | |
| | Rasagiline | |
| | Ropinirole | |
| | Rotigotine Selegiline | |
| | Pimavanserin (Nuplazid) | |
| SLE | Azathioprine | |
| | Belimumab | |
| | Cyclophosphamide | |
| | Hydroxychloroquine | |
| | Methotrexate | |
| | Methylprednisolone | |
| | Mycophenolate mofetil | |
| | Prednisone | |

Dynamic Scoring

In some embodiments, the system can utilize PRO disease measures that score severity (or broader concepts like quality of life) based on a predefined set of questions, regardless of individual member characteristics. This approach can be used by the system to begin with a new user. For example, initial questions can be used to yield a score that describes how severe a particular disease is in relation to the user. Over time, more personalized scoring can be used based on the attributes of the individual user. For example, if a first user has 8 symptoms and a second user has 12 symptoms, their symptom severity scores will take their individual symptoms into account.

Figure 17:
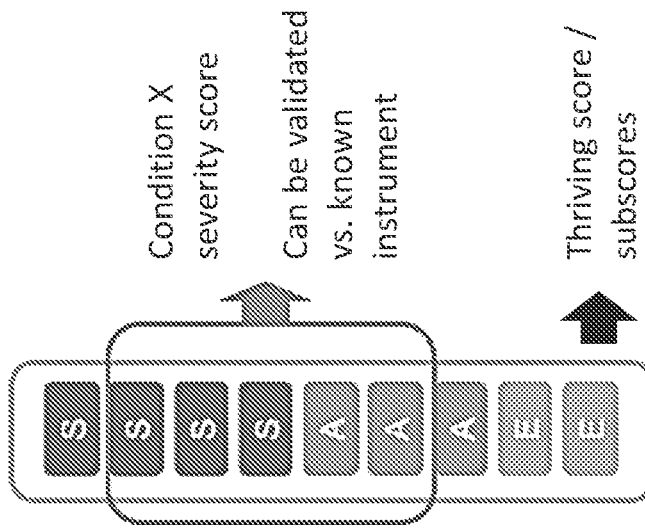
FIG. 17 illustrates an exemplary embodiment of a scoring approach.

An exemplary embodiment of a scoring approach is shown in FIG. 17, where S, A, and F are all different question templates relating to symptom severity, ability, and experience.

In some embodiments, the use of the dynamic measure can benefit from use of advanced measurement techniques (modern psychometric theory) such as Rasch modelling to ensure that information reflected back to patients is meaningful. For example, the user can be provided with information including average scores showing how the user is doing relative to others, providing information regarding changes in their score that are clinically meaningful, and that scores can reflect a full range of severity, In some embodiments, various scores can be gleaned from the data. Some of these scores, such as symptom severity or functional ability (for example, walking, cognition, etc.) can be used to determine treatment effectiveness, while others, such as thriving, can be used to understand the impact of one or more interventions on the quality of life of the patient. In some embodiments, a symptom severity score can be used to indicate, overall, how bad the negative effects of a user's conditions and treatments are to the user, including any side effects. Various approaches can be used to determine this score, including a Rasch score.

In some embodiments, a symptom severity scale can be used that is an average of tracked symptoms, or it can be an index that accounts for a percentage of "moderate" and "severe" responses. In some embodiments, scoring can include a weight system that assigns heavier weights to some symptoms over others. In some embodiments, the frequency of symptom episodes (for example, how often seizures occur and how many of those involve loss of consciousness) can be used to access severity. In some embodiments, scoring can include questions specific to a diagnosis, treatment, gender, age, or other user characteristics.

In some embodiments, ability or functioning scores describe a user's perception of functioning, meaning how well does the user feel able to function. These scores may or may not track with objective measures of specific abilities like walking, remembering, or breathing. In some embodiments, scoring can be achieved using Rasch scoring of core items, translated, for example into a 1-10 scale, for patient interpretation. In some embodiments, scoring can include questions specific to a diagnosis, treatment, gender, age, or other user characteristics.

In some embodiments, a thriving score can be comprised of core experience items (connectedness, effectiveness, etc.) and encompasses the domains a user describes as "thriving" or living well. In some embodiments, scoring can be achieved using Rasch scoring with a translation, for example into a 1-10 scale, for user interpretation. In some embodiments, this score can include questions specific to a diagnosis, treatment, gender, age or other user characteristics such as a caregiver role.

Additional scoring can include a condition impact score (s) that relates to condition severity in conditions that don't have specific severity measures.

Knowledge Creation

Various scientific tools and methods can be applied to the data collected by the system to develop methods based on the finding related to the data. For example, a hierarchy of hypotheses can be tested using descriptive statistics, between-group comparisons, correlations, the building of associative networks and N-of-1 studies across different levels of complexity. Further, data gather can be expressed in the context of a knowledge engine using tools such as Biological Expression Language (BEL) which allows for comparison of new data to existing findings from the literature or other studies.

Insight Delivery and Givebacks to Users

In some embodiments, the system can have the ability to reflect information back to the patient. Typically, when patients complete a health questionnaire, do a survey in research, or visit their doctor, they receive little in the way of context back. The system can reflect back to individuals (whether patients with a medical condition or "healthy" people wishing to learn more about their bodies) unique information gleaned from other people with similar health and/or life profiles, for example, who suffer from the same or similar disease, have a shared biomarker, or share similar life circumstances and goals.

In some embodiments, the system can develop scientific insights relating to the characterization and progression of disease or new analysis methods for identifying disease and drug activity. For example, longitudinal data can characterize the natural history of a progressive condition and interrogation of associated biological data could identify markers in bio-specimens associated with deviance from the typical progression pattern, such as rapid progression, slow progression, or harbingers of changes in rates of progression such as relapses or flares.

In some embodiments, the system can reflect back insights about patient behavior and sentiment that highlight potential competitive advantages, unmet patient needs, potential cost savings, or other business opportunities relevant to life sciences, payers, and healthcare providers. For example, identification of changes in biological networks associated with worsening or improvement of disease might provide clues to the viability of different approaches to advancing a putative therapy from a drug company's portfolio of candidates from its pipeline.

Figure 19A:
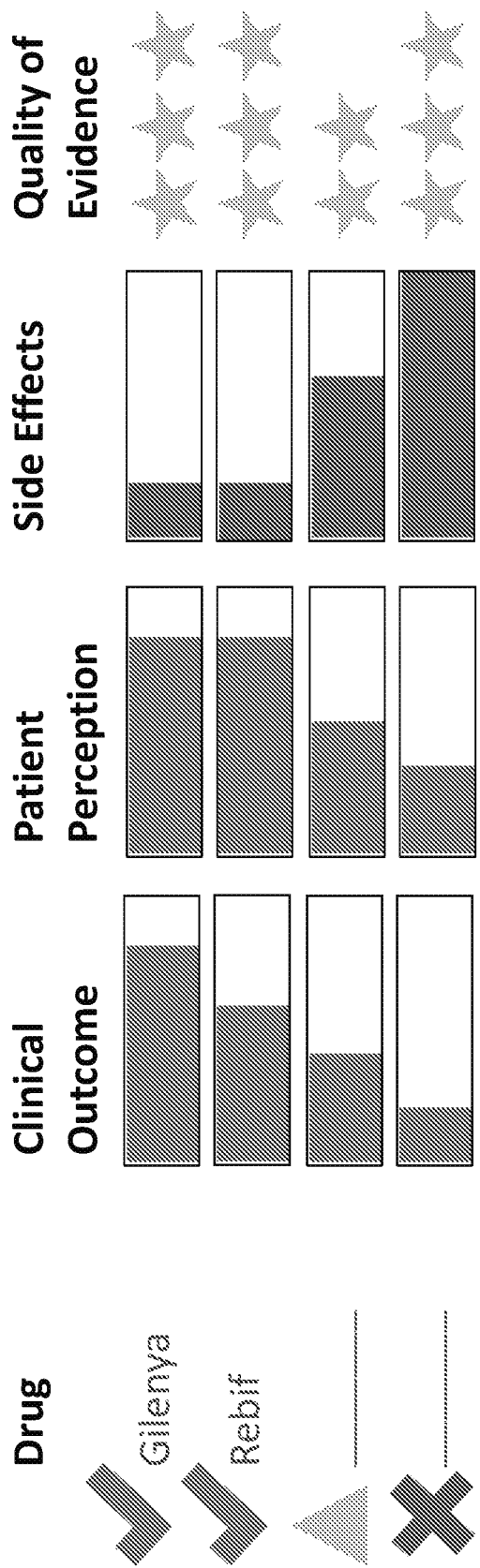
Figure 19B:
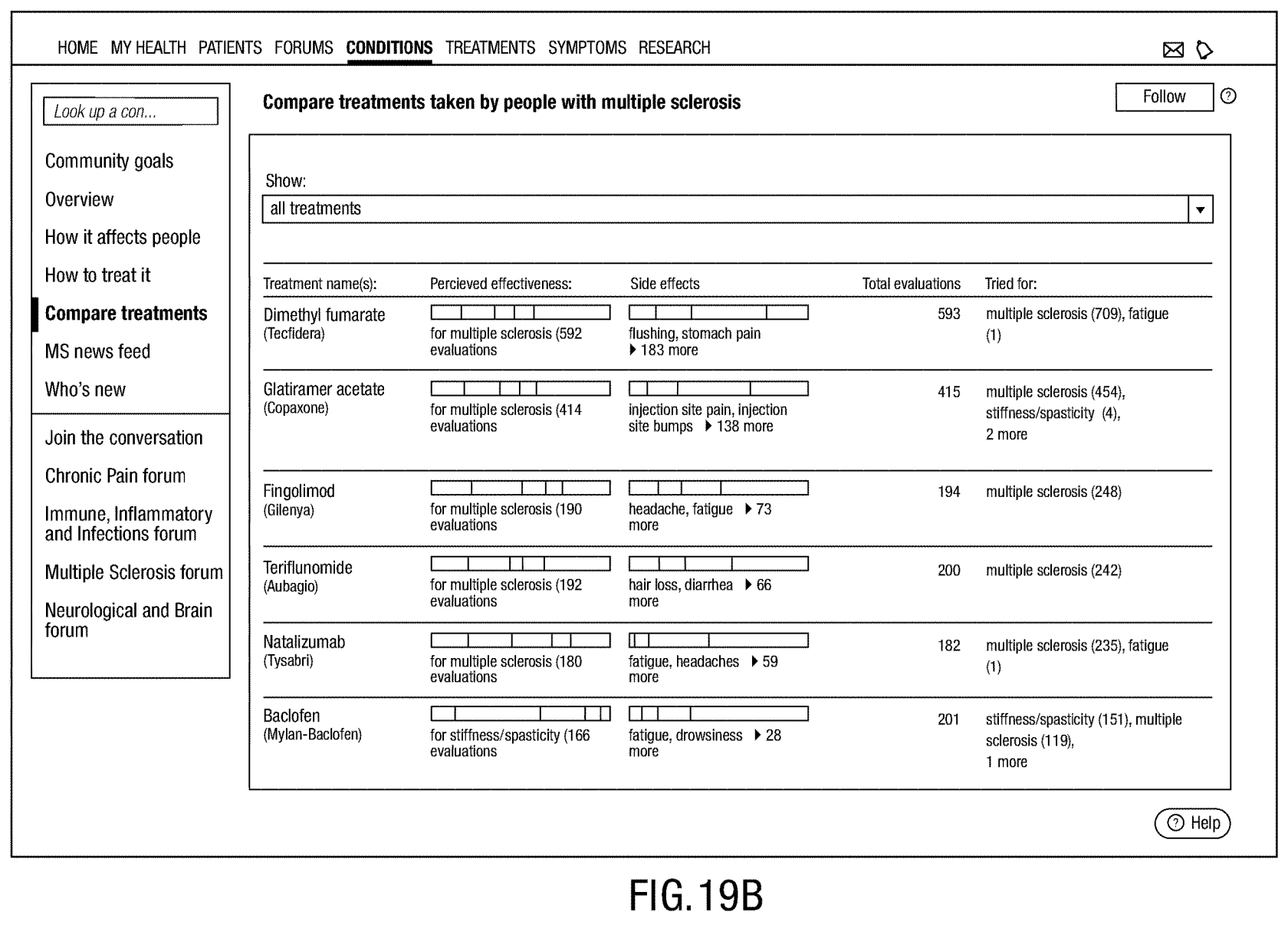
Figure 20A:
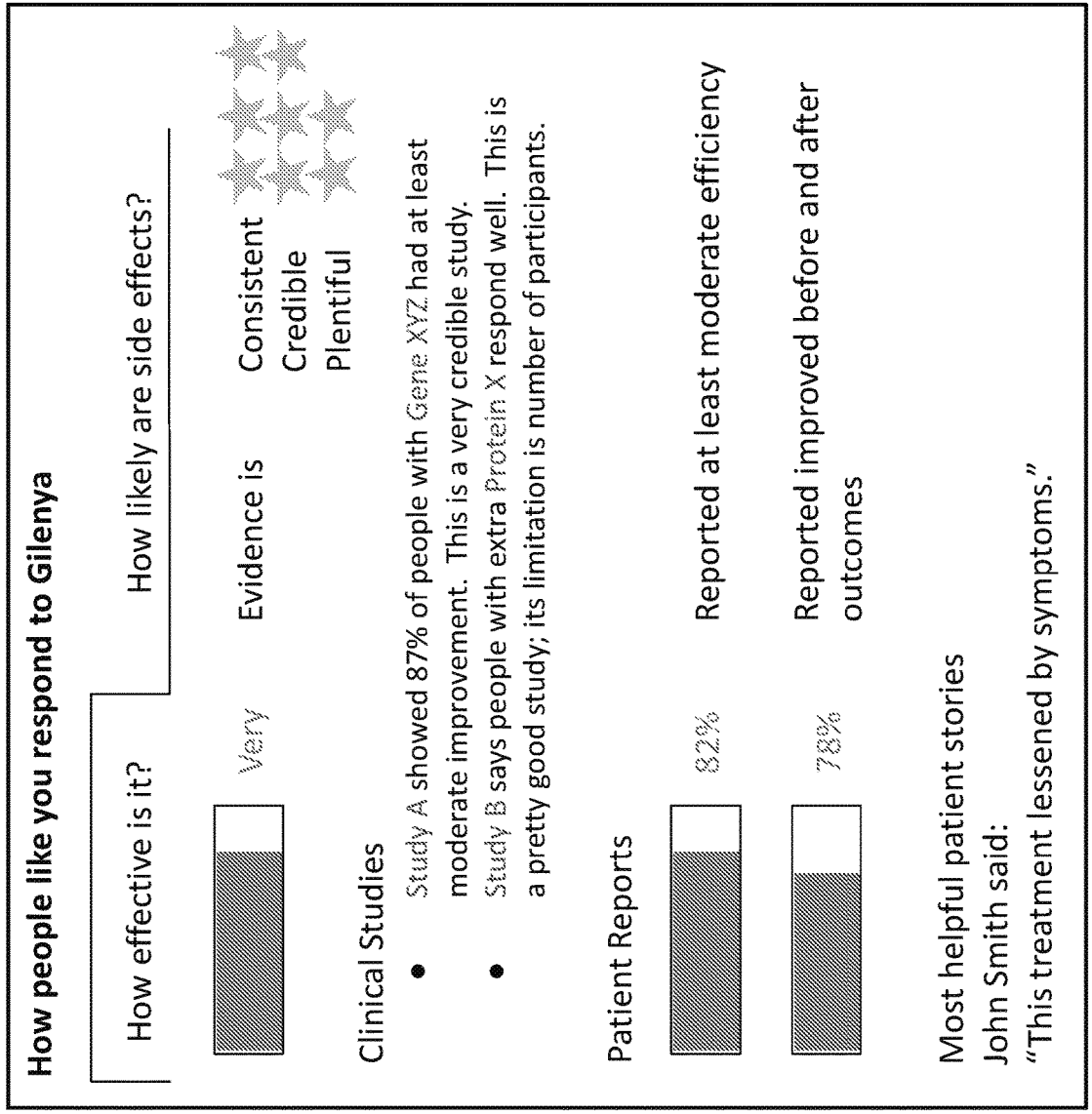
Figure 20D:
Figure 20E:
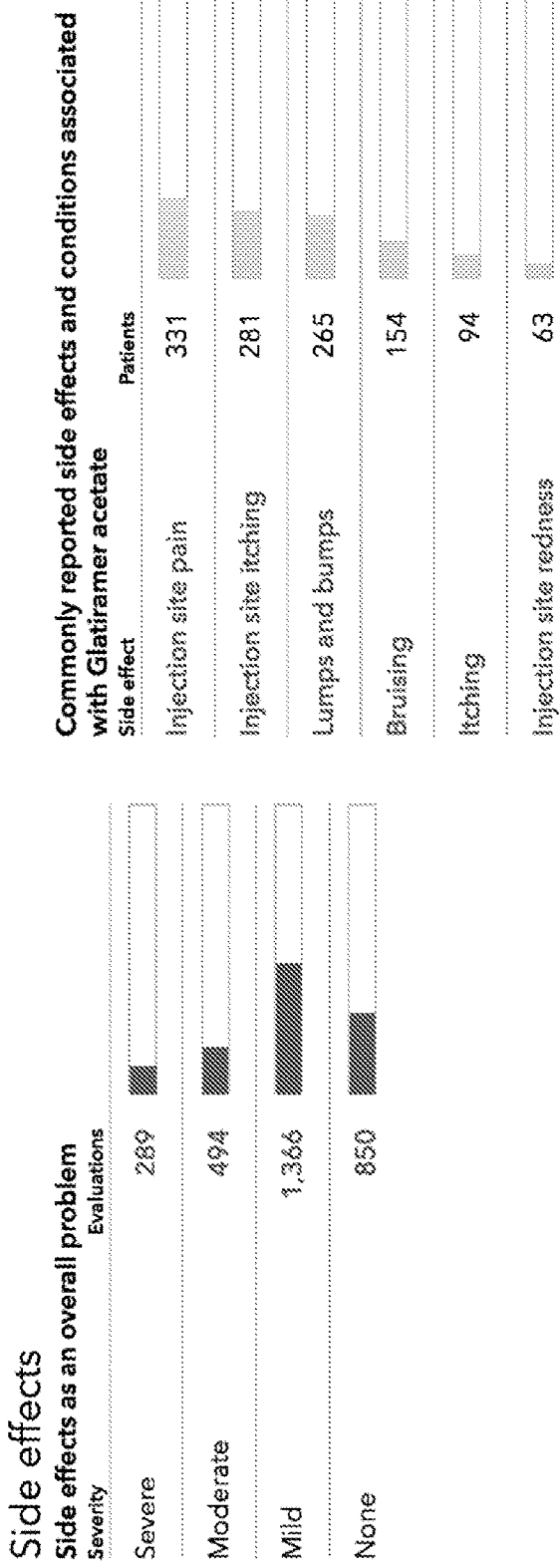
Figure 20G:
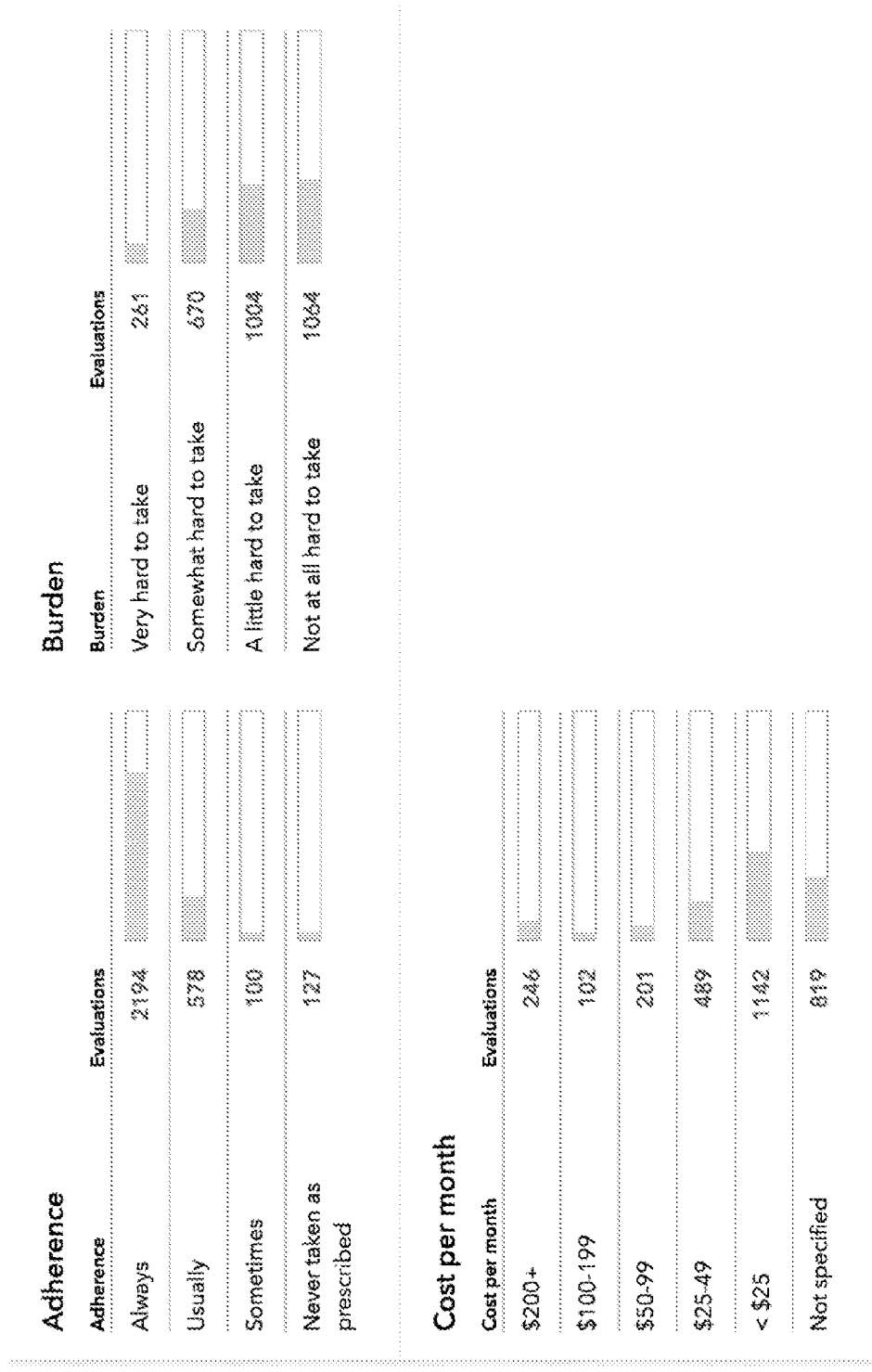

In some embodiments, the system has the capability to deliver both aggregated data (which has not been analyzed for meaning) and rigorously developed insights. Examples of data presented to a user are shown in FIG. 18, FIG. 19A, FIG. 19B, FIG. 19C, FIG. 20A, FIG. 20B, FIG. 20C, FIG. 20D, FIG. 20E, FIG. 20F, FIG. 20G, and FIG. 20H, For example, FIG. 19A illustrates an exemplary embodiment of an interface showing content that is available in "compare treatments" and "how people treat it" pages within a specific condition report. FIG. 19B illustrates an exemplary embodiment of an interface of a report that is available for a patient interested in learning more about treatments for a disease, such as multiple sclerosis, based on aggregated data shared by patients. FIG. 19C illustrates an exemplary embodiment of an interface of a report that is available for a patient interested in learning more about treatments for a disease, such as multiple sclerosis, based on aggregated data shared by patients. FIG. 20A illustrates an exemplary embodiment of an interface showing content that is available in individual treatment evaluations and report pages. FIG. 20B illustrates an exemplary embodiment of an interface of information shared in individual treatment evaluations. FIG. 20C illustrates an exemplary embodiment of an interface of information shared in individual treatment evaluations. FIG. 20D, FIG. 20E, FIG. 20F, FIG. 20G, and FIG. 20H illustrate exemplary embodiments of an interface showing the type of information shared in specific treatment report pages.

In some embodiments, aggregate member data can be used to show users unanalyzed numbers based on user information collected by the system (for example, what percentage of people with condition X have Y symptom). Users are left to draw their own conclusions from this type of data.

For example, when an individual submits a biosample or completes medical history and patient-reported outcome (PRO) data about themselves, including health questionnaires (such as the questionnaire shown in Table 3), the individual can be shown an image and/or text demonstrating how many other people there are like them based on criteria such as demographics and their own responses, They can be presented with simplified statistics and charts showing, for example, where they rank in terms of percentiles or quartiles for some attribute, including but not limited to patient-reported status (such as symptom severity or walking ability) or some biological measure (such as a blood test result or the prevalence of a particular bacterium in their biosample). Further, if they have provided the same data point more than once, they can be shown the trend in their data.

Figure 21:
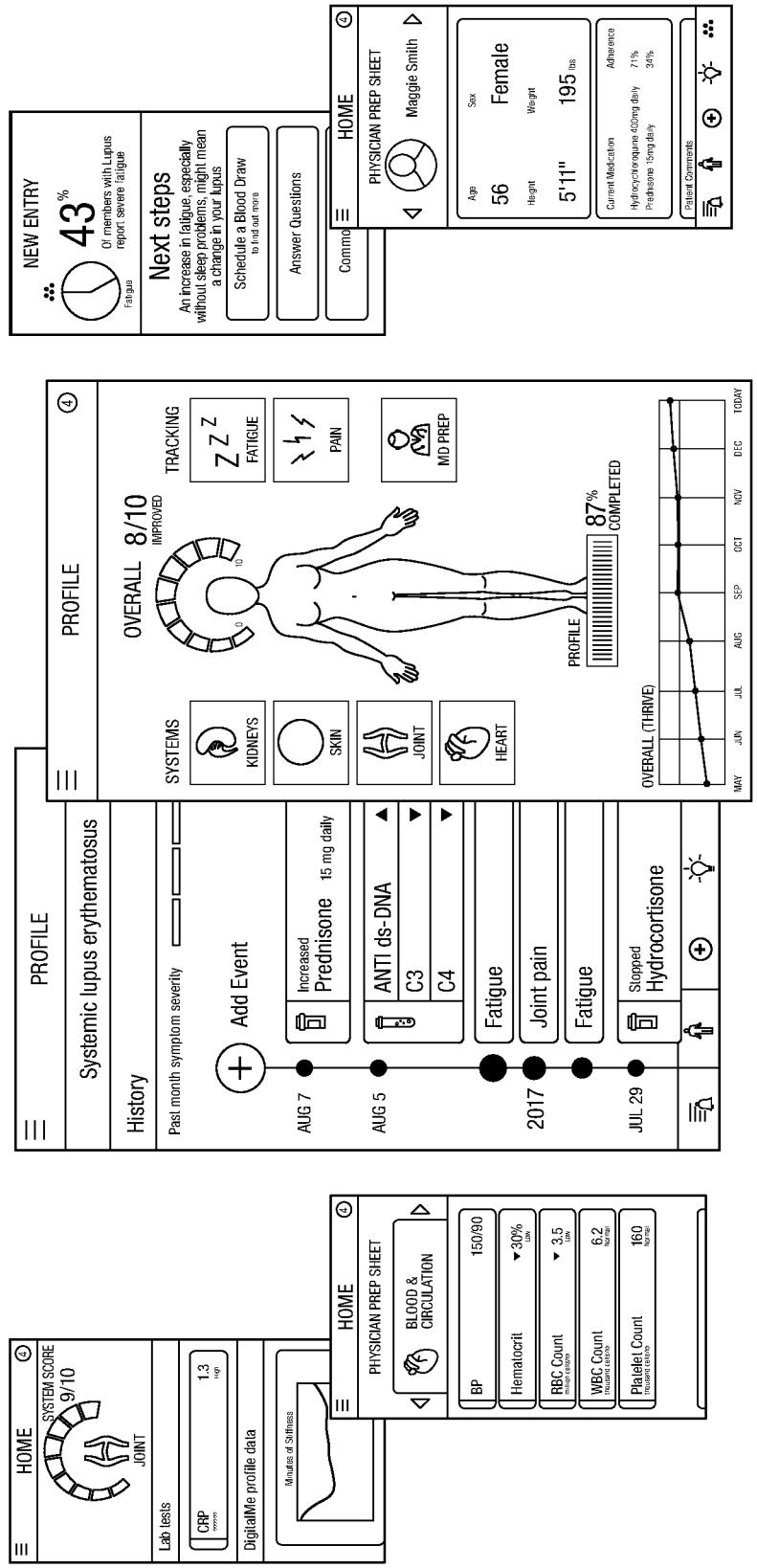
FIG. 21 is an exemplary body system diagram for visualizing a health assessment.

In some embodiments, results are combined in various ways to provide users with a view of overall system status or an assessment of some aspect of health, Examples include but are not limited to assessments of: cardiovascular risk, overall kidney function, physical fitness, or health risk due to behavior. These assessments can be based on a combination of lab values, physical measurements, device data, health history, patient-reported data, and/or other sources. The assessments can be based on validated clinical studies or—with appropriate disclaimers and as required by regulation—on preliminary scientific models. These can be depicted in various ways, including but not limited to graphs, lists of results, or body system diagrams. One exemplary embodiment of a body system diagram used to visualize a health assessment is shown in FIG. 21. Thus, in some embodiments, a visual representation of a disease, a patient's life strategy, or other information collected and/or processed can be presented to a user to visually convey an understanding of their condition/illness or health status.

In some embodiments, personalized medical advice can be provided to users. Using various methods to analyze user data and samples, the system can deliver personalized medical advice to help users and their healthcare providers make the best preventive care, lifestyle, and treatment decisions. In addition to user data, packaged insights can draw upon third-party data (such as existing clinical guidelines or scientific literature). Such advice can include, but is not limited to, the best tests, treatments, and lifestyle interventions for managing a disease or symptom (such as "reducing fatigue" or "slowing kidney damage due to lupus") or accomplishing a health goal (such as "building muscle" or "losing weight"). In some embodiments, these interventions are presented as experiments to try and report back on, Any such recommendation can be delivered along with a confidence rating based on the strength of the evidence (such as whether it is a new and unvalidated finding on the one hand vs. confirmed in a systematic review or meta-analysis of interventional clinical trials on the other).

In some embodiments, the system can provide various customized reports of "omics" information. In some embodiments, a customized report can be generated that can be geared towards a doctor. The system can use a variety of omics technologies, including but not limited to full genome/exome sequencing, transcriptomics (RNA sequencing), metabolomics, proteomics, immunosignature, microflora/fauna, and others. Often, the raw data regarding omics information can be incomprehensible and can need to be curated. For example, various "givebacks" may include basic information about the test, its level of validation, how much evidence we have generated for individuals like the doctor's patient, patient-specific findings (such as deviation from norms, changes over time, correlations between—omics and patient reported symptoms), our confidence for each recommendation, and supplementary assay quality assurance information (e.g. batch number). For example, genetic sequencing of an individual with ALS may show that they have the genetically inherited form of the disease, regardless of whether they have any family history of disease (whether as a spontaneous mutation or because of unclear family history).

Based on the patient's informed consent, preferences for information giveback, the local regulations where a user lives, and other considerations, software can be used to generate an outline report for the patient and/or their clinician to indicate information of clinical significance to report to them based on research finding. A report can include various types of data along with the omics information, including genetic data from public databases (for example, ALSOD.org, the public database of ALS genetic mutations), as well as appended articles from the scientific literature. For example, it might reveal that a patient has a recessive SOD1 D90A mutation (found among those of Scandinavian descent) which contains the key context that patients with this form of the illness tend to live much longer than average (around 10 years) as opposed to the mean duration for most patients (2-5 years) or more aggressive genetic mutations (e.g. A4V, 18 months). Depending on whether the test was performed in a CLIA lab, it can be possible to repeat the test before sending results to the clinician or make a recommendation that they repeat the test. The report can be reviewed by a healthcare professional for quality and accuracy before sending.

In some embodiments, a customized report can be generated that can be geared towards a user, such as a patient or customer. Similar considerations as described above for doctors apply though in some embodiments these reports can be consumer-grade reports of lower medical significance. In some embodiments, the same or similar results as those sent to a doctor can be sent to a patient along with one or more pieces of accompanying material, such as educational material or a quiz to confirm that the user understands what conclusions can and cannot be drawn from this type of data. In some embodiments, the system can recommend or allow the user to book an appointment with a genetic counsellor or clinician to explain the results before the user can see them.

In some embodiment, the system can also be used to share potentially meaningful research results (for example, newly identified subtypes in a disease) that are personalized but are not actionable medical advice. During the course of scientific research the use of clustering techniques like Principal Component Analysis (PCA) can discover latent variables that group patients together. Although these will be statistically identified clusters (e.g. "Type A") rather than having a pathophysiological descriptor (e.g. "T-cell mediated"), it can still be interesting and worthwhile for patients to be able to group themselves with a similar patients who are similar by statistical grouping based on their underlying omics, not merely their clinical or demographic data. For patients with sufficient interest and appropriate informed consent, the patient can be "matched" with other patients who are like them biologically for purposes of group comparisons or for social features (e.g. forums, message boards, or other social features). In another example, a specific immunosignature might be identified which is highly predictive of individuals with systemic lupus erythematosus (SLE). Patients who report a diagnosis of SLE could get access to their levels of this unique immunosignature at baseline and over time as their condition waxes and wanes. Such information can be provided with appropriate caveats, for example, that the information is "research grade" and therefore experimental, not "clinical grade."

In some embodiments, users can receive other "givebacks" of general interest, such as explanations of research goals and methods or discussion of preliminary findings. Examples of various user givebacks can include, but are not limited to:

Explanation of what is measured and why

How and why are we trying to change our measurement model?

Explanation of the limitations in how diseases are categorized and diagnosed, and why syndromic conditions need to be measured differently.

How general health perception and common domains vary across conditions

How symptom severity and other domains vary by time since diagnosis

Who reports more limitations with certain activities and abilities (by condition, by time since diagnosis.

What other domains correlate with good or bad "experience" domains (e.g. do bad symptoms or sleep seem to track with low self-esteem, does low self-efficacy seem to correlate with low health perception, etc.)

Are there conditions where side effects are perceived as worse than symptoms

Mobility: how ALSFRS, PDRS, MSRS measure these, what additional insight we can get from a questionnaire (e.g. mobility aids used)

When people perceive a change in their health, which measurement domains seem to shift with that (e.g. a change in <this symptom> or <this experience domain> correlates with a bigger perceived health change).

How much health change people perceive in various conditions

Lifestyle factors: How stress, sunlight, self-reported fitness, diet, and sleep data correlate with perceived health and condition impact Substance impact: how alcohol, caffeine, and nicotine use correlate with outcomes How "health events" (e.g. new diagnoses, falls, ER visits, etc.) correlate with outcomes (e.g. perceived health change, other domains)

What outcomes correlate with any signal in blood

What health events correlate with any signal in blood

The following is an exemplary analysis of data results for a general interest giveback to users. A study was conducted that carried out a survey of 1,270 users of the system (69% female) reporting primary conditions of:

Neurological diseases (N=717, 56.4%)

371 MS (29.2%)

203 PD (16.0%)

143 ALS (11.2%)

Mood disorders (N=434, 34.1%)

15 GAD (1.2%)

287 MDD (22.6%)

132 PTSD (10.4%)

Lupus—121 SLE (9.5%)

The users were asked how much their primary condition affected their life in the last month on a scale of "none, mild, moderate, or severe." Ranked by adding "moderate" and "severe" together, the user rating the highest level of impact were:

PTSD (86% moderate or severe impact)

MDD (81%)

SLE (80%)

ALS (68%)

GAD (67%)

MS (68%)

PD (55%)

The users were asked how they felt their general health had been on a scale of "Poor, fair, good, very good, and excellent." Ranked by adding "Poor" and "Fair" together with the lowest health were:

SLE (68% poor or fair)
PTSD (58%)
MDD (57%)
MS (40%)
ALS (31%)
PD (28%)
GAD (20%)

By comparing both of these items, the impact reported by the users of their conditions is relatively high (at least half reported moderate or severe impact), but it might be counterintuitive that neurological conditions appear to have less impact than mental health conditions in our system. The different magnitude of responses to the health question (20%, 68%) relative to the impact question (55%, 86%) also suggest that "health" and "impact of a condition" mean different things to people, and the multi-systemic condition of SLE scoring highest on health impact is perhaps not that surprising, but then, again, PTSD and MDD appear to have a worse health state than ALS, often considered a particularly terrible disease.

Users were asked how they felt their health had changed (if at all) over the last month. Most users (33-52%) felt they were either about the same, or a little worse (20-39%).

Although the sample was smaller (N=15), patients with a primary condition of GAD were the only group likely (40%) to report an improvement. ALS patients were the least likely (6%) to report an improvement, reflecting the progressive nature of their condition, but 16% of MS patients and 19% of PD patients said they were feeling better. In terms of feeling "worse" or "a lot worse," SLE patients had the highest rate (17%) followed by PTSD (12%), as shown in Table 7 below.

TABLE 7

| | MS | PD | ALS | GAD | MDD | PTSD | SLE | Total |
|---|---|---|---|---|---|---|---|---|
| Last month change | | | | | | | | |
| Much worse | 1% | 1% | 1% | 0% | 1% | 1% | 2% | 1% |
| Worse | 8% | 4% | 8% | 0% | 8% | 11% | 15% | 8% |
| A little worse | 23% | 28% | 39% | 20% | 28% | 38% | 31% | 29% |
| About the same | 52% | 49% | 46% | 40% | 42% | 33% | 35% | 45% |
| A little better | 11% | 11% | 3% | 13% | 15% | 13% | 13% | 11% |
| Better | 5% | 7% | 2% | 27% | 5% | 4% | 5% | 5% |

TABLE 7-continued

| | MS | PD | ALS | GAD | MDD | PTSD | SLE | Total |
|---|---|---|---|---|---|---|---|---|
| Much better | 1% | 1% | 1% | 0% | 2% | 0% | 0% | 1% |
| Last month change (collapsed categories) | | | | | | | | |
| Worse | 32% | 33% | 48% | 20% | 37% | 50% | 47% | 38% |
| About the same | 52% | 49% | 46% | 40% | 42% | 33% | 35% | 45% |
| Better | 16% | 19% | 6% | 40% | 22% | 17% | 18% | 17% |

Users can have a variety of experiences with treatment side effects. In an exemplary study, about 90% of users were taking some sort of treatment. Of these, about a third (36%) had no side effects from treatment, about a third (32.5%) had only mild side effects, about one in 5 (18%) had moderate side effects, and just 1 in 25 (4%) reported severe side effects, as shown in Table 8 below. Those with PTSD were the most likely (32%) to report moderate or severe side effects, closely followed by patients with SLE (31%), MDD (28%), GAD (27%), and PD (24%), as shown in Table 8 below. Rates in ALS were relatively low (7%) although they also had a higher proportion of patients not taking any treatments as shown in Table 8 below.

TABLE 8

| | MS | PD | ALS | GAD | MDD | PTSD | SLE |
|---|---|---|---|---|---|---|---|
| Tx Side Effects | | | | | | | |
| None | 41.20% | 34.50% | 53.80% | 13.30% | 31.70% | 25.80% | 23.10% |
| Mild | 30.70% | 38.40% | 23.80% | 46.70% | 33.80% | 30.30% | 35.50% |
| Moderate | 12.70% | 18.70% | 7.00% | 20.00% | 24.00% | 25.80% | 25.60% |
| Severe | 3.80% | 5.40% | 0.00% | 6.70% | 3.80% | 6.10% | 5.00% |
| I'm not taking any treatments | 11.60% | 3.00% | 15.40% | 13.30% | 6.60% | 12.10% | 10.70% |
| Tx Side Effects Compressed | | | | | | | |
| None + Mild | 71.90% | 72.90% | 77.60% | 60.00% | 65.50% | 56.10% | 58.60% |
| Moderate + Severe | 16.50% | 24.10% | 7.00% | 26.70% | 27.80% | 31.90% | 30.60% |
| I'm not taking any treatments | 11.60% | 3.00% | 15.40% | 13.30% | 6.60% | 12.10% | 10.70% |

The following are exemplary results of various questions posed to users:

Over the last month, how well could you sleep?
Poorly (38%)
Fairly well (44%)
Very well (14%)
Extremely well (4%)
Over the last month, how much sleep did you get?
Not enough (54%)
The right amount for me (33%)
Too much (13%)
Please rate the difficulty of falling asleep over the last month
None (23%)
Mild (33%)
Moderate (30%)
Severe (14%)
Please rate the severity of any difficulty staying asleep over the last month
None (13%)
Mild (34%)

Moderate (35%)
Severe (18%)
Thriving elements
Over the last month, how often did you feel good about yourself?
None of the time (17%)
Some of the time (44%)
Most of the time (30%)
All of the time (9%)
Over the last month, how often did you find meaning in your life?
None of the time (17%)
Some of the time (42%)
Most of the time (27%)
All of the time (14%)
Over the last month, how often did you feel connected to others?
None of the time (14%)
Some of the time (50%)
Most of the time (26%)
All of the time (10%)
Over the last month, how often did you feel able to live the life you wanted?
None of the time (18%)
Some of the time (42%)
Most of the time (31%)
All of the time (10%)

Curation and Automation of Insight Delivery

In some embodiments, the system can filter recommendations and other insights based on the characteristics of the patient, including but not limited to biological measures, health history, demographics, or goals. Insights generated based on the data of other members are automatically tagged with the attributes of those members.

Figure 22A:
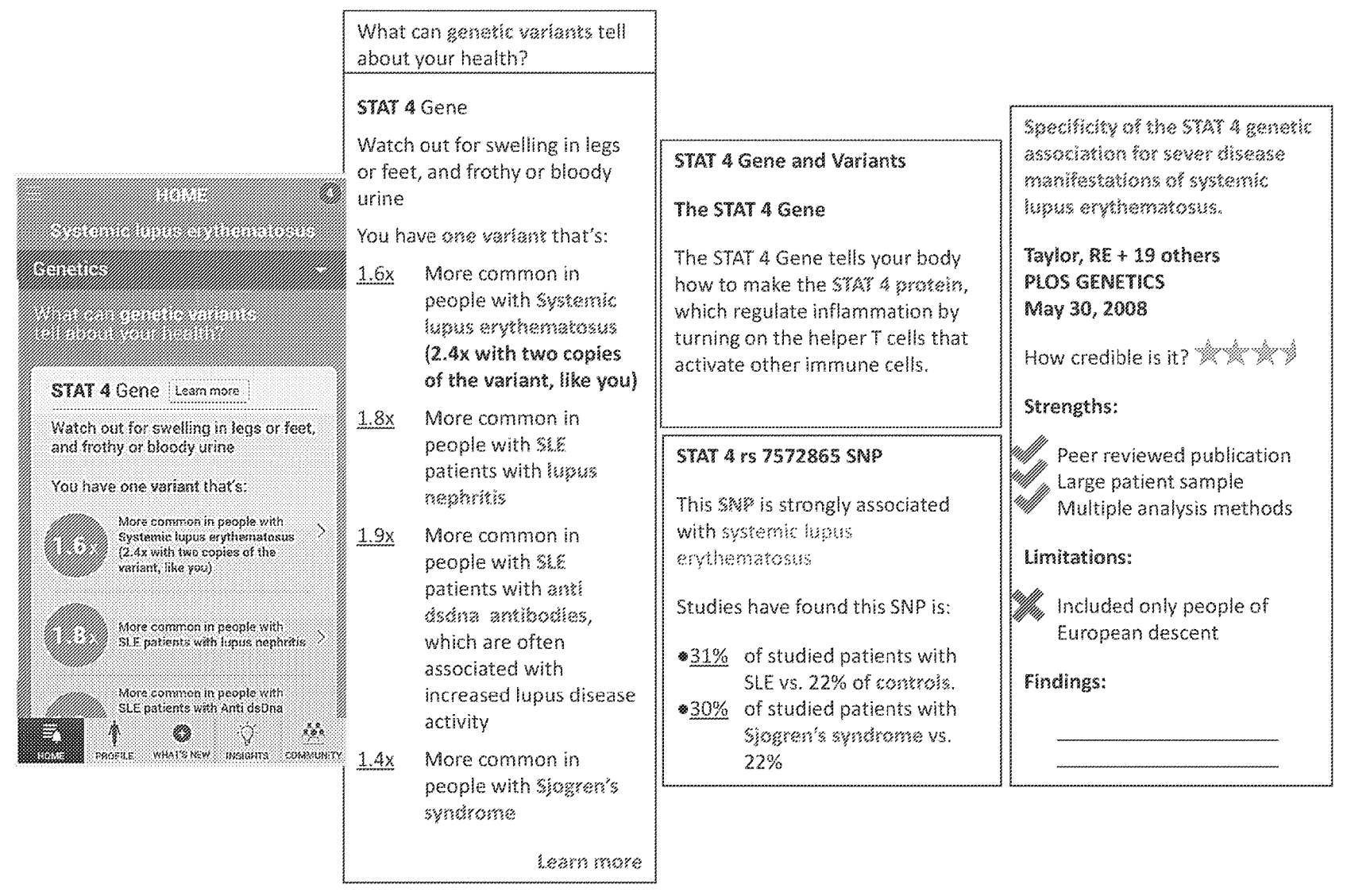
Figure 22B:
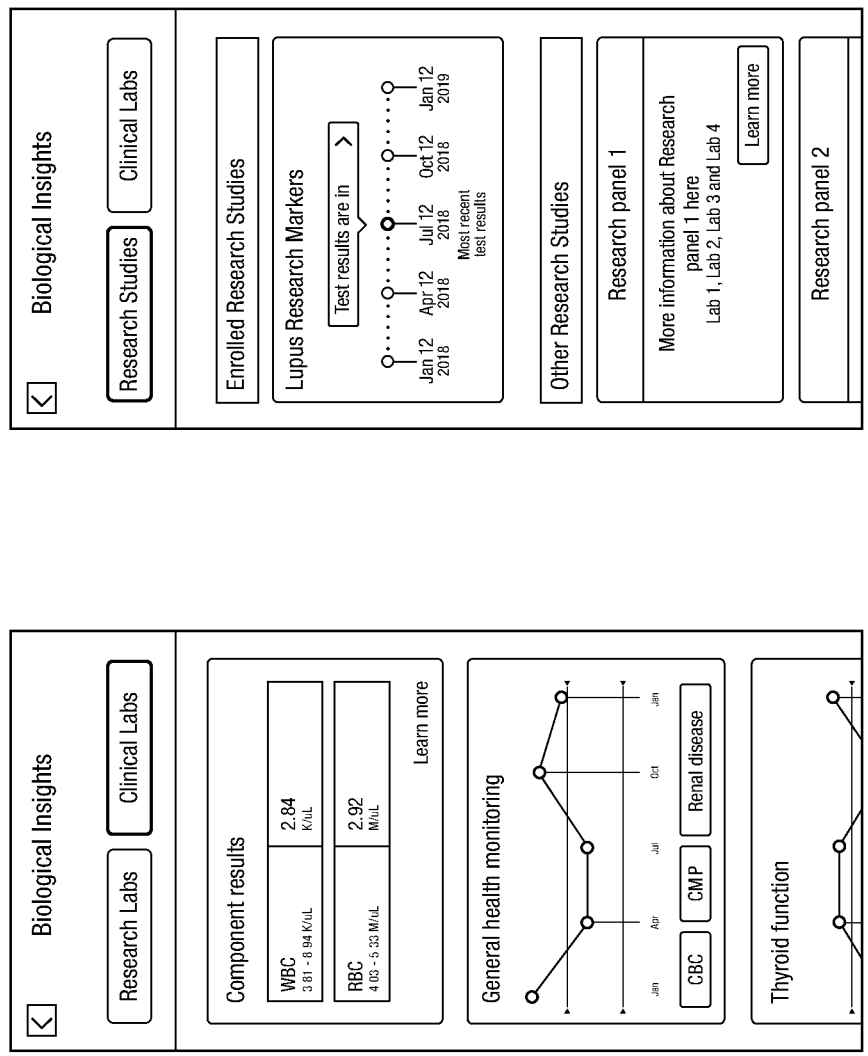

In some embodiments, to deliver insights based on third-party guidelines or research studies, the system can use professional curation that codifies the characteristics of the people in the cited study, the benefits and problems they experienced, a rating of the study's quality, and the reasons for that rating. These attributes of a recommendation are used to filter what each member sees. Further, these recommendations can be presented with contextual information that helps users assess how applicable those insights are to the individual. For example, the system would show an individual that 31% of other lupus patients with her same genetic variation experienced improvement in fatigue on a particular drug, vs. 18% of controls; further, it could tell the patient that the study's might be less applicable because it did not include patients of African American descent. One exemplary embodiment of a user interface for displaying insight information is shown in FIG. 22A and FIG. 22B.

Givebacks that Solicit Additional Data Input

In some embodiments, insight delivery of any of the types described herein can also be used to solicit further data entry. For example, when a user reports a significant positive change in symptom or ability score, optional open "tips and tricks" text boxes can be used to encourage members to report tips and advice they would offer to other members going through a similar experience to effect positive change. For example, a member whose ability to "Connect with others" may have improved might report that they have joined a local exercise club. A member in a wheelchair reporting an improvement in cognitive function and social connectedness may report that they have found a way to connect their ventilator to an external battery, therefore allowing them to sleep better and leave the house more.

Healthcare professionals can read, curate, tag, and structure these health hacks. Members reporting poor scores in the same domain may optionally choose to receive a curated set of tips to help enable them to improve their outcomes. These members can rate the helpfulness of tips and make their own suggestions or modifications to the techniques or advice offered.

Research and Trials

In some embodiments, the system can be used to run experiments to improve outcomes, and can recommend either third-party clinical trials or virtual experiments for which the user might be eligible.

Most clinical trials are large-scale expensive experiments (costing from millions of dollars up to $2.6 billion at the highest estimates) which attempt to control for a multitude of factors through randomization, typically of an experimental group against a placebo-controlled group taking an inert substance. However, such experiments typically have highly restrictive inclusion/exclusion criteria (limiting generalizability of the eventual findings), are restricted to experimental products (as opposed to approved ones), can only be conducted for a very limited subset of medical interventions (typically new disease modifying therapies), and are very resource intensive, requiring many visits to clinical centres and coordination of a range of clinical personnel.

By contrast, the system can be used to perform "hybrid virtual trials" online, using virtual study visits, patient self-report, telephone or teleconference follow-up, an open protocol design, and the use of real-time data aggregation to show individual results as they are entered by trial participants. In some embodiments, the system can be configured to allow users to volunteer to take part in pragmatic trials, i.e. trials leveraging the existing data they are submitting as part of their participation, but with the expectation that they will volunteer to be randomized to one of a number of non-placebo interventions where there is a lack of clinical certainty as to which approach is best.

For example, in a cohort of members with ALS self-identifying as suffering from uncontrollable outbursts of emotional expression such as laughter, crying, and smiling, software can be used to identify those patients not currently taking any treatment know to be indicated (or in widespread off-label use) for PBA and to ask patients to volunteer to be randomized into one of several groups. In practice this would involve providing them with informed consent documentation, basic educational materials, a request to send to their clinician, and tools to randomize the patient to request from their clinician that they be provided a randomized intervention from a fixed list of feasible treatments (e.g. Nuedexta (Dextromethorphan/quinidine, Avanir Pharmaceuticals), citalopram (generic), fluoxetine (generic), or amitriptyline (generic)) or dose ranges (e.g. amitriptyline at 10 mg, 20 mg, 30 mg, 40 mg, 50 mg). Patients can document in an "n-of-1" manner their experience with the intervention, and as the experiment continues, be shown edited summaries of data from the trial in general, designed so as not to bias the interpretation of the patients taking part but to maintain their interest.

In some embodiments, the system can also be used for research involving other interventions, including those that are non-pharmacological such as dietary interventions, behavioural modifications, psychotherapy, telemedicine, or subscribing to nutraceutical/health food deliveries.

In some embodiments, the system can be used in relation to omics changes and graph backs. Tools can be used to help users/patients understand the way different omics function inside their bodies, e.g. proteomics. A user interface, for example a browser can be used to help them view how some aspects of their biology and/or patient-generated health data remain stable over time, some change. For example, protein expression is highly stable over certain periods of time for many proteins, such as a time span of 4 months (for example, which can be the planned blood draw sequence. Among those that are variable over time, machine learning software could help extract unselected candidate proteins that seem to change for that individual in synchrony with worsening/improvement of their disease status.

Annotated browsers can take a selected subset of proteins identified from the scientific literature or from proprietary libraries used by omics assays vendors as being particularly relevant to certain diseases. For example, a specific Health-Tell immunosignature has been identified which is highly predictive of individuals with systemic lupus erythematosus (SLE). Patients who report a diagnosis of SLE could get access to their levels of this unique immunosignature at baseline and over time as their condition waxes and wanes. Such information can be provided with appropriate caveats, for example, that the information is "research grade" and therefore experimental, not "clinical grade."

There are a variety of ways to make the system accessible to a user and to collect data from the user. The system allows people to learn about the opportunity to participate in a scientific research program, and if eligible, give their informed consent to enroll. At regularly designated intervals they will be asked to submit self-reported electronic data and biological samples (for instance, surveys about their well-being every month and blood about 3 times a year). In addition, if they experience a "state change," for example a significant worsening or improvement in their health, they can opt to request another biological sample collection at any time. As they take part, they are provided with "give-backs" which provide contextual feedback as to how they are doing with their condition. The data collected is merged into a single electronic system which can be interrogated for scientific research purposes, leading to novel scientific discoveries, business insights, and personalized medical advice.

Figure 23A:
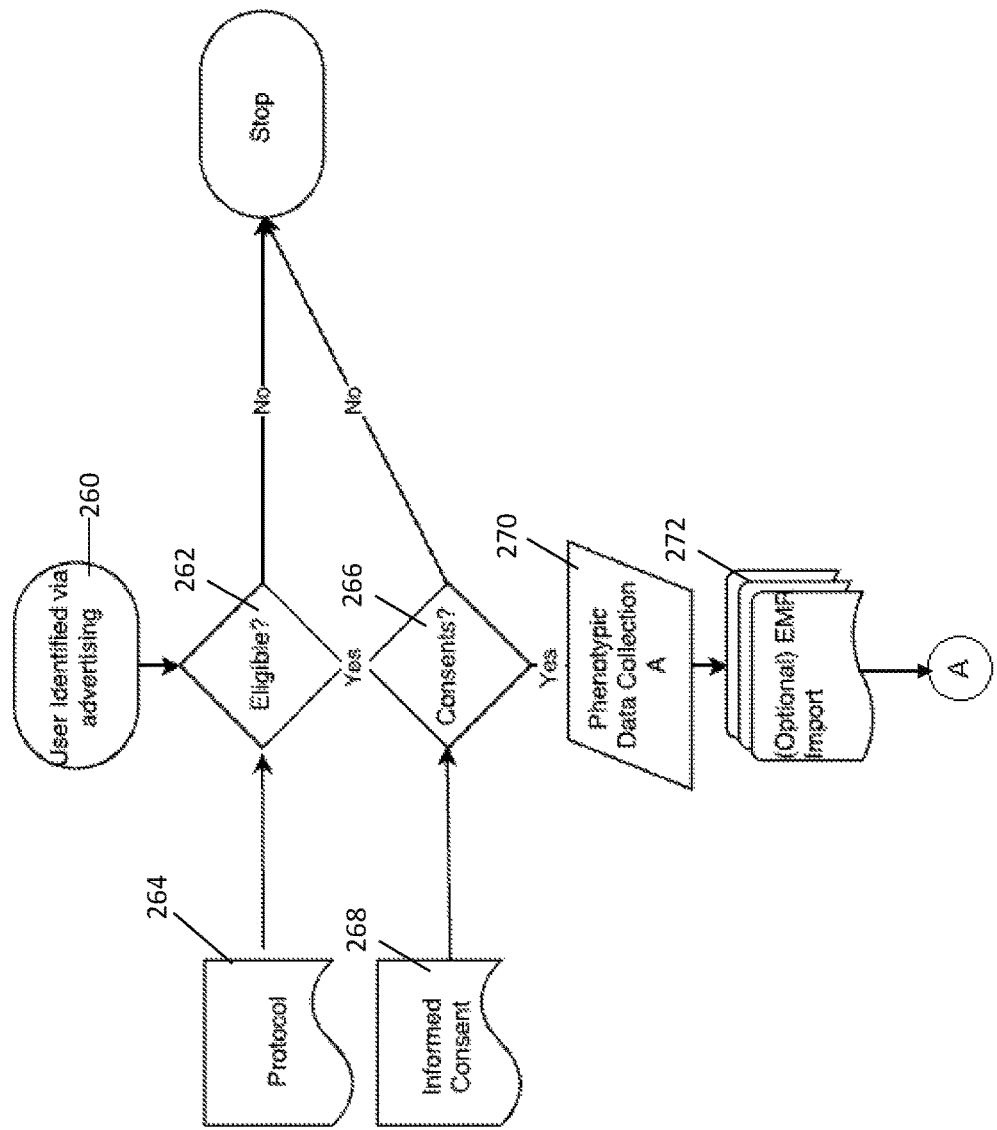
FIG. 23A and FIG. 23B illustrate exemplary flowcharts for collecting and analyzing biological and phenotypic data from a user.
Figure 23B:
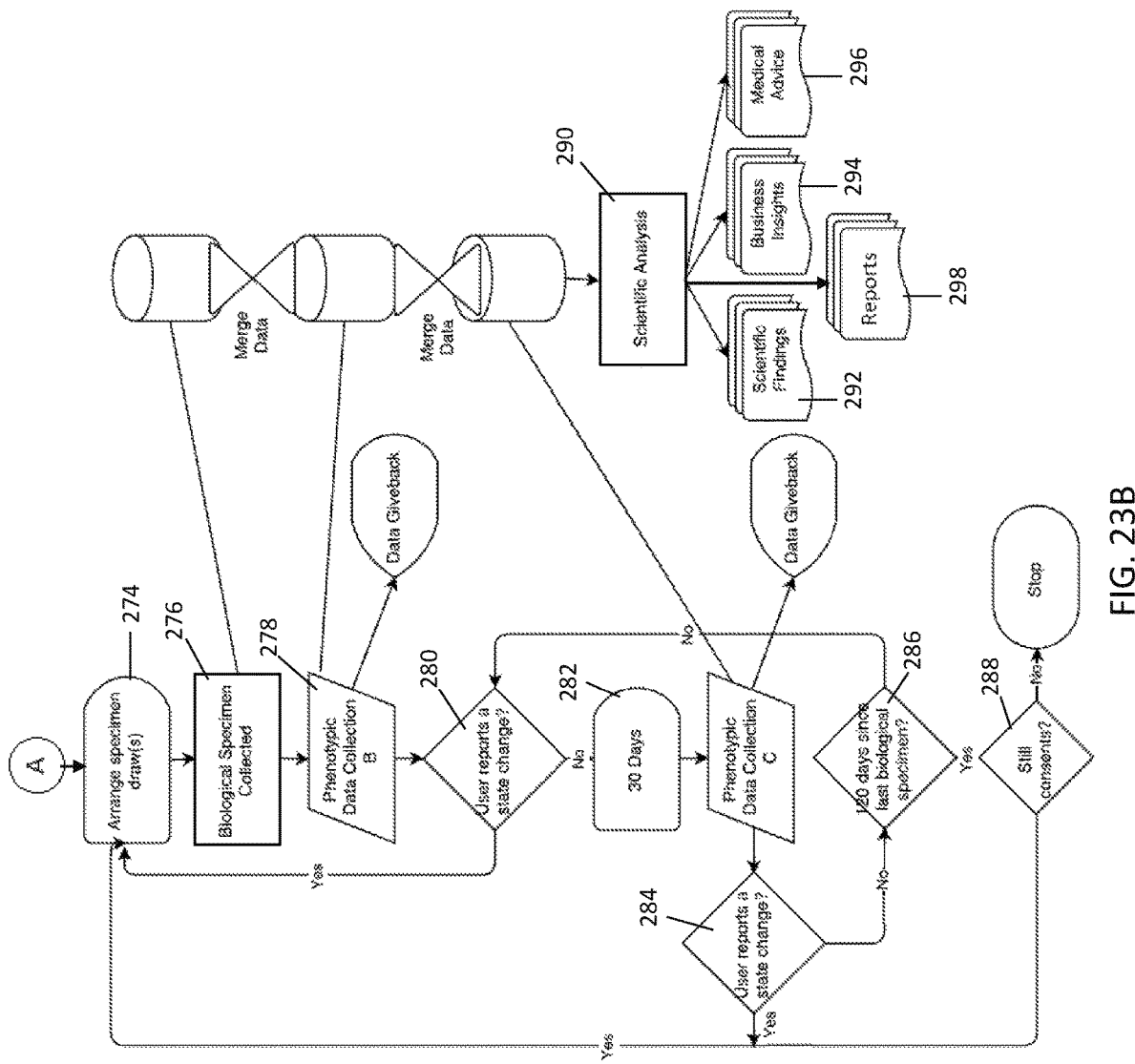
Figure 24:
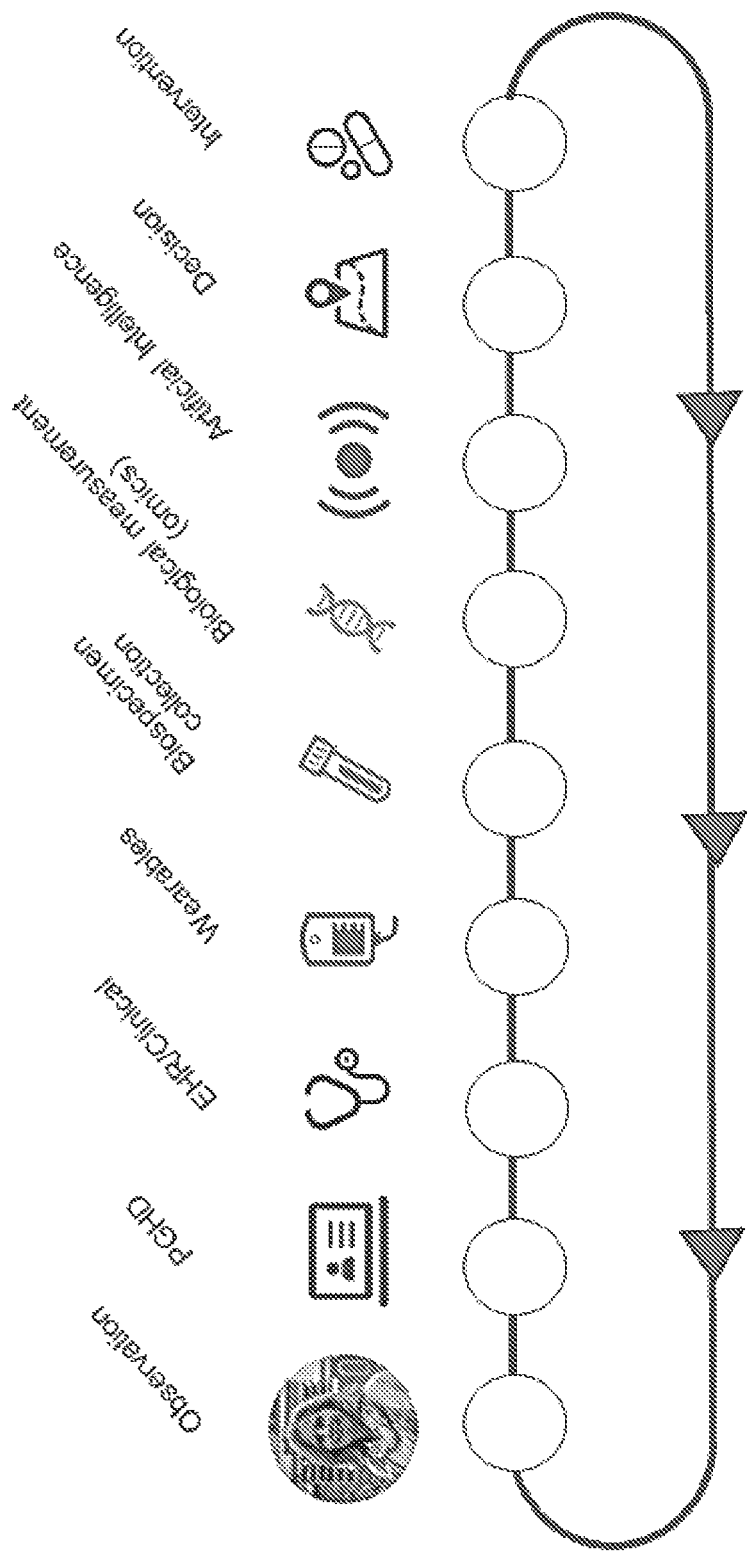
FIG. 24 illustrates an exemplary flowchart of data collection and analysis.

FIG. 23A and FIG. 23B illustrates an embodiment of a method for collecting and analyzing data from a user. In some embodiments, potentially eligible users are identified (step 260) by advertising, word of mouth, or direct referral, and a "landing page" can be displayed detailing the risks and benefits of accessing the system. A user can be registered if they are not already members of the system. A series of questions can be presented to a user to gauge their eligibility (step 262), as defined by a protocol 264, and an informed consent document for their review can be displayed (step 266). If they agree to take part, informed consent 268 can be recorded. Once a user is registered and has given consent, the process of collecting data can begin. For example, a baseline set of information can be collected ("Phenotypic Collection A") in step 270, including contact details and basic health history information. It can also be possible to get permission and relevant access details to obtain their electronic medical records (EMRs) in step 272. In order to collect one or more biological specimens, the system can schedule a time to arrange a specimen draw in step 274 (e.g. blood, saliva, feces, urine, and/or breath). After collection of the one or more biological specimens in step 276, information ("Phenotypic Collection B") can be collected in step 278 about their health status and other data useful in analyzing their specimen (e.g. last time they ate anything) within a threshold period of time. For example, information can be collected within 24 hours of collection of the one or more biological specimens. Following sample collection, users can be provided with an option to report a change in their medical status ("State change") in between monthly surveys (step 280). If no state change is reported, users can be provided with regular monthly electronic surveys about their health status (step 282). In some embodiments, the monthly surveys can also include questions meant to detect state changes. Users can be asked to schedule specimen collection if they meet certain state change criteria (step 284), and if not then specimen draws can occur at specified intervals (e.g. every 120 days) in step 286. This process can be repeated until consent is withdrawn (step 288) or the service ends. The data that is collected can be merged such that scientific analysis can be performed (step 290), that can result in scientific findings 292, business insights 294, medical advice 296, and/or reports 298. FIG. 24 illustrates another exemplary flowchart of data collection and analysis.

It will be understood that the process of obtaining samples and/or information from a user can vary and can depend on the type of information required based on the type of service an individual user has consented to. Thus, sample and/or information collection can occur on a pre-set time interval, can be initiated by the user, or can be triggered based on criteria found in the data. The data that can trigger a sample and/or information collection can include, but is not limited to, data reported by the user, from a previous sample collection, any wearable devices or sensors collecting data from the user, or from any other source related to the user.

Healthcare Provider and Caregiver Involvement

In some embodiments, the system can be used for one- or two-way communication with a user's healthcare provider or other caregivers. Users can specify which providers or caregivers have access to what data, or can manually share specific data with the provider. In some embodiments, a patient/user can create a care circle that can include people that can view and/or share information as part of the patient's profile and data in the system. Providers can receive the data in a variety of ways, including but not limited to a provider graphical user interface, a printout shared by the patient, or via the existing electronic health record's PDF or other data acceptance functionality. In some embodiments, a physician or healthcare provider visit prep sheet can be utilized, that functions as a way to capture information in the system to present the current state of the patient to the healthcare provider, for example, before a scheduled appointment. This allows the healthcare provided to receive patient-provided information before a visit, and in some embodiments the system can include lab data, biological analysis, and/or care suggestions based on that information and insights obtained from the patient as compared to the community of users. The communication gap between patients and healthcare providers can be lessened and allow healthcare providers to treat the whole patients and not just their illness. The prep sheet can include patient-reported profile changes, such as information relating to symptoms, life strategies, and any changes or concerns, and can be presented to the physician in a concise report. In some embodiments, the prep sheet can include insights relating to the illness, and information about new treatment options with supporting materials for their use in treating the patient. The prep sheet can be provided to a healthcare provider in a variety of ways, including but not limited to an encrypted pdf document sent for example via email, through a mobile application, and a data upload to a system in the office of the healthcare provider.

In some embodiments, a healthcare provider can set parameters or add data on behalf of the patient. Parameters include, but are not limited to, custom targets or alerts for a patient's test results (including results that may indicate medication non-adherence), patient-reported data, or medication adherence. In addition, a healthcare provider might make a determination that a patient-reported symptom or side effect can be attributed to a particular disease or treatment; for example, a patient may share a photo of a rash, which a physician determines is related to their fibromyalgia rather than their systemic lupus, and should therefore be treated differently.

Case Study Examples

Below are various non-limiting examples within the spirit and scope of the presently disclosed embodiments.

Multiple Sclerosis (MS)

A 30-year old white female patient with a 10-year history of relapsing-remitting multiple sclerosis (RRMS) has been treated with an older disease-modifying therapy and has recently started experiencing relapses (new symptoms or worsening of existing symptoms lasting more than 24 hours and confirmed by a neurologist or with MRI evidence). She joins the system and has blood drawn at baseline and completes Thrive and the MS Rating Scale (a clinically validated measure for legacy comparison purposes). In the first year she has her blood drawn on the regular cadence of every 4 months but 30 days after her most recent draw she alerts the PLM team that she is experiencing a state change; she can't shake a head cold and is worried that this might trigger a relapse of her condition. An additional blood draw is taken within 24 hours and added to a tagged series of blood specimens which goes into a pool of other specimens labelled as "state changes" signifying that patients may be more likely to have a relapse. A week after her blood draw she is admitted to hospital where her neurologist confirms new lesions on MRI; she reports back to the system that the blood draw was taken either just before or during the relapse. Her clinician is given an automated report of how her omics and patient-generated health data varied over the preceding year's worth of samples from the state change draw. Her clinician is able to see that in her immune system a particular type of immune cell appears to be particularly active, which is targeted by a recently approved therapy. She is switched onto the new therapy and reports an improvement in her symptoms and has no further relapses over the next 5 years.

Lupus

A 55-year old African-American woman with a 20 year history of systemic lupus erythematosus (SLE) has been struggling to manage her symptoms and the impact that SLE has on her daily life. In particular she has felt isolated, stigmatized, and depressed by the fact that much of her disease is "invisible," and so unlike people with a more obvious physical impairment she faces scepticism and hostility at work as to how sick she is really feeling. On joining the system, she provides a blood sample, completes the questionnaire and the Lupus Impact Tracker (LIT, a clinically validated measure for comparison purposes). An automated report is generated for her which shows her that, relative to other patients who have had SLE for a similar duration of the same background, she is in the worst 25% of all patients in terms of her experiences. The system automatically highlights several areas including fatigue, sleep quality, and connectedness to others where she is scoring poorly and where she does not appear to be using any treatments. The system highlights pharmacological and non-pharmacological treatments for her symptoms that other patients like her have reported as effective. In addition, she sees a series of text tips written by patients like her about how to deal with issues such as isolation and stigma, She is offered social connections to other patients who have been living with the disease for a little longer than she has and a conversation thread is prompted to which she is invited to read, on how other people have found ways to explain their situation to their employers. When her blood results come back, she feels validation from seeing the tell-tale immunosignature of someone with lupus and shares summaries of the findings with her colleagues to help explain how the invisible parts of her immune system are attacking her organs.

ALS

A 65 year old white male with recent onset of slurred speech and swallowing difficulties is given a diagnosis of "possible ALS". He was adopted and does not know his family history. Upon enrolment to the system, he has blood drawn and completes Thrive and the ALS Functional Rating Scale, Revised (ALSFRS-R, a clinically validated measure for comparison purposes). Whole genome sequencing reveals a mutation in the superoxide dismutase-1 that is known to be causative of ALS. Because he opted to have his clinician (but not himself) be informed of any clinically relevant results, his doctor receives a report letting her know about this development, alongside prognostic information combining publicly available data such as ALSOD.org's listing for his mutation as well as the progression of other similar patients who have enrolled in the system. This contains predictive models of when he might experience spread to other regions of his body such as arms, legs, and breathing muscles. It also contains predictions of other key milestones in ALS progression such as need for feeding tube, external ventilator support, and use of a power wheelchair. The patient opted not to receive this information himself and so the clinician uses it to advise her multidisciplinary team when he next visits clinic. As a result, problems are pre-empted in a stepped approach that avoids crises but also disclosing information to the patient or his family which they might be unable to handle. His status as a genetic disease carrier is never disclosed to the patient or his family, per his request.

Diabetes

A 32 year old Chinese female with type I diabetes registers for the system to learn more about her metabolism. In addition to blood draws and patient-generated health data from the Thrive measure, she chooses to upload blood glucose and insulin dosing data from her continuous glucose monitor (CGM), implanted insulin pump (known as an "artificial pancreas" or "closed loop"), her internet-enabled weighing scales, and her smartphone's accelerometer and GPS. She also takes regular photographs of her meals with a smartphone app. By combining her data with that of thousands of other patients like her, machine learning algorithms are able to identify that a significant proportion of variance in her continuous blood glucose, metabolic HBA1C levels, and other metabolic markers is accounted for by features of her diet and low-intensity exercise. Through a partnership with the company that supplies her CGM, she is offered free sensor pads each month that she achieves a personally-tailored step count based on her occupation, commute, and demographics. For a monthly fee, she subscribes to delivery of personalised diet foods that help her maintain her optimal metabolism and is able to see for herself the improvement to her risk factors and health outcomes that such changes have made to her life. Once enough data has been collected, the system can begin making suggestions to the software engineers who designed her CGM algorithm as to further ways to optimise her loop.

The present disclosure is described with reference to block diagrams and operational illustrations of systems, methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

For the purposes of this disclosure a computer readable medium (or computer-readable storage medium/media or non-transitory computer readable recording medium) stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage medium/media or non-transitory computer readable recording medium, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media or non-transitory computer readable recording medium includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure the term "server" or central computer should be understood to refer to a service point which provides processing, database, and communication facilities. By way of example, and not limitation, the term "server" or central computer can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure, a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a wired or wireless line or link, for example.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly.

A wireless network may further employ a plurality of network access technologies, including Wi-Fi, Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For purposes of this disclosure, a client device, such as, for example, a smart device, a tag, or an aggregator, may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device, a Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

A client device may vary in terms of capabilities or features. Claimed subject matter is intended to cover a wide range of potential variations. For example, a simple smart phone, phablet or tablet may include a numeric keypad or a display of limited functionality, such as a monochrome liquid crystal display (LCD) for displaying text. In contrast, however, as another example, a web-enabled client device may include a high-resolution screen, one or more physical or virtual keyboards, mass storage, one or more accelerometers, one or more gyroscopes, global positioning system (GPS) or other location-identifying type capability, or a display with a high degree of functionality, such as a touch-sensitive color 2D or 3D display, for example.

A client device may include or may execute a variety of operating systems, including a personal computer operating system, such as a Windows, iOS or Linux, or a mobile operating system, such as iOS, Android, or Windows Mobile, or the like.

A client device may include or may execute a variety of possible applications, such as a client software application enabling communication with other devices, such as communicating one or more messages, such as via email, for example Yahoo!® Mail, short message service (SMS), or multimedia message service (MMS), for example Yahoo! Messenger®, including via a network, such as a social network, including, for example, Tumblr®, Facebook®, LinkedIn®, Twitter®, Flickr®, or Google+®, Instagram™, to provide only a few possible examples. A client device may also include or execute an application to communicate content, such as, for example, textual content, multimedia content, or the like. A client device may also include or execute an application to perform a variety of possible tasks, such as browsing, searching, playing or displaying various forms of content, including locally stored or streamed video, or games. The foregoing is provided to illustrate that claimed subject matter is intended to include a wide range of possible features or capabilities.

Figure 25:
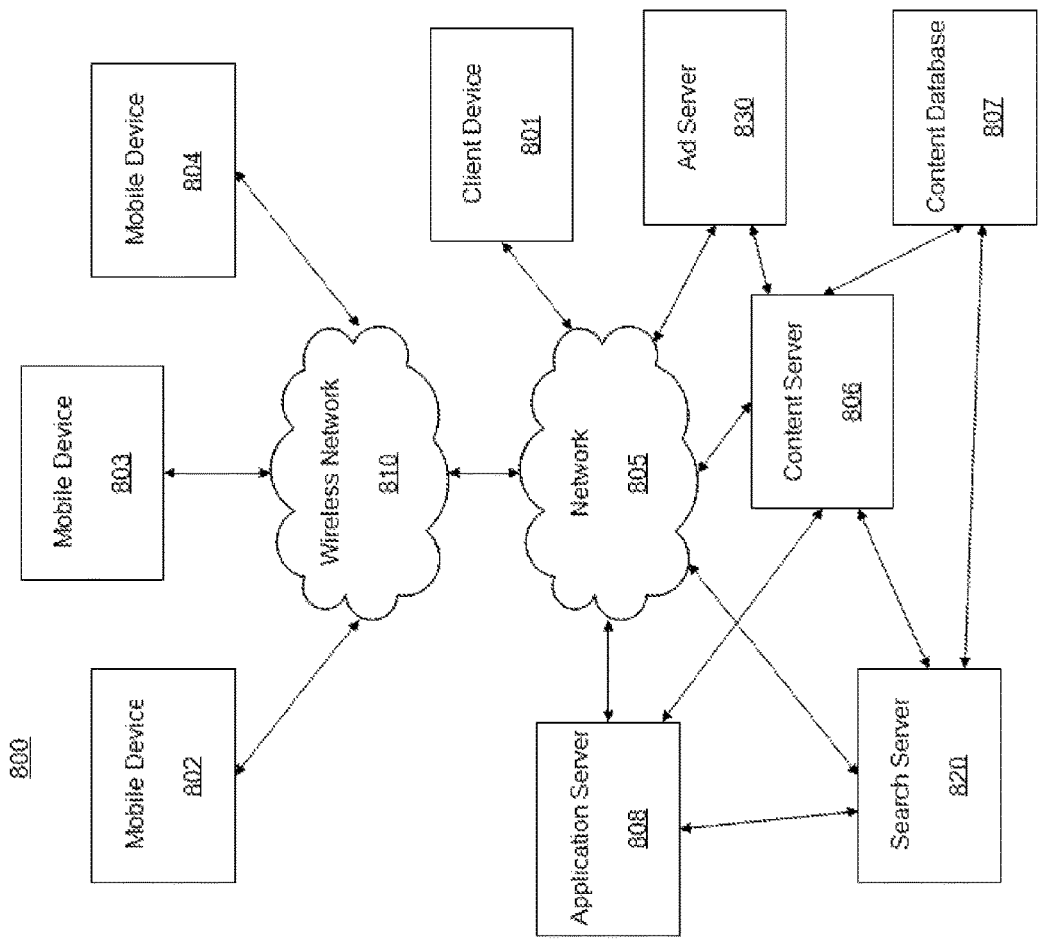
FIG. 25 is an exemplary block diagram illustrating mobile devices and a client device in communication with servers.

In general, with reference to FIG. 25, a system 800 in accordance with an embodiment of the present disclosure is shown. Not all the components may be required to practice the disclosure, and variations in the arrangement and type of the components may be made without departing from the spirit or scope of the disclosure. As shown, system 800 of FIG. 25 includes local area networks ("LANs")/wide area networks ("WANs")—network 805, wireless network 810, mobile devices (client devices) 802-804 and client device 801. One or more of mobile devices 802-804 and/or client device 801 may be a tag, a smart device, and/or an aggregator. FIG. 25 additionally includes a variety of servers (e.g., central computer), such as content server 806, application (or "App") server 808, search server 820 advertising ("ad") server 830, and content database 807.

One embodiment of mobile devices 802-804 is described in more detail below. Generally, however, mobile devices 802-804 may include virtually any portable computing device capable of receiving and sending a message over a network, such as network 805, wireless network 810, or the like. Mobile devices 802-804 may also be described generally as client devices that are configured to be portable. Thus, mobile devices 802-804 may include virtually any portable computing device capable of connecting to another computing device and receiving information.

A web-enabled mobile device may include a browser application that is configured to receive and to send web pages, web-based messages, and the like. The browser application may be configured to receive and display graphics, text, multimedia, and the like, employing virtually any web based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message.

Mobile devices 802-804 also may include at least one client application that is configured to receive content from another computing device. The client application may include a capability to provide and receive textual content, graphical content, audio content, and the like. The client application may further provide information that identifies itself, including a type, capability, name, and the like. In one embodiment, mobile devices 802-804 may uniquely identify themselves through any of a variety of mechanisms, including a phone number, Mobile Identification Number (MIN), an electronic serial number (ESN), or other mobile device identifier.

In some embodiments, mobile devices 802-804 may also communicate with non-mobile client devices, such as client device 801, or the like. Client device 801 may include virtually any computing device capable of communicating over a network to send and receive information. The set of such devices may include devices that typically connect using a wired or wireless communications medium such as personal computers, multiprocessor systems, microprocessor-based or programmable consumer electronics, network PCs, or the like. Thus, client device 801 may also have differing capabilities for displaying navigable views of information.

Client devices 801-804 computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like.

Wireless network 810 is configured to couple mobile devices 802-804 and its components with network 805. Wireless network 810 may include any of a variety of wireless sub-networks that may further overlay stand-alone ad-hoc networks, and the like, to provide an infrastructure-oriented connection for mobile devices 802-804. Such sub-networks may include mesh networks, Wireless LAN (WLAN) networks, cellular networks, and the like.

Network 805 is configured to couple content server 806, application server 808, or the like, with other computing devices, including, client device 801, and through wireless network 810 to mobile devices 802-804. Network 805 is enabled to employ any form of computer readable media or non-transitory computer readable recording medium for communicating information from one electronic device to another. Also, network 805 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another, and/or other computing devices.

Within the communications networks utilized or understood to be applicable to the present disclosure, such networks will employ various protocols that are used for communication over the network. Signal packets communicated via a network, such as a network of participating digital communication networks, may be compatible with or compliant with one or more protocols. Signaling formats or protocols employed may include, for example, TCP/IP, UDP, QUIC (Quick UDP Internet Connection), DECnet, NetBEUI, IPX, APPLETALK™, or the like. Versions of the Internet Protocol (IP) may include IPv4 or IPv6. The Internet refers to a decentralized global network of networks. The Internet includes local area networks (LANs), wide area networks (WANs), wireless networks, or long haul public networks that, for example, allow signal packets to be communicated between LANs. Signal packets may be communicated between nodes of a network, such as, for example, to one or more sites employing a local network address. A signal packet may, for example, be communicated over the Internet from a user site via an access node coupled to the Internet. Likewise, a signal packet may be forwarded via network nodes to a target site coupled to the network via a network access node, for example. A signal packet communicated via the Internet may, for example, be routed via a path of gateways, servers, etc. that may route the signal packet in accordance with a target address and availability of a network path to the target address.

According to some embodiments, the present disclosure may also be utilized within or accessible to an electronic social networking site. A social network refers generally to an electronic network of individuals, such as acquaintances, friends, family, colleagues, or co-workers, that are coupled via a communications network or via a variety of sub-networks. Potentially, additional relationships may subsequently be formed as a result of social interaction via the communications network or sub-networks. In some embodiments, multi-modal communications may occur between members of the social network. Individuals within one or more social networks may interact or communication with other members of a social network via a variety of devices. Multi-modal communication technologies refers to a set of technologies that permit interoperable communication across multiple devices or platforms, such as cell phones, smart phones, tablet computing devices, phablets, personal computers, televisions, set-top boxes, SMS/MMS, email, instant messenger clients, forums, social networking sites, or the like.

In some embodiments, the disclosed networks 810 and/or 805 may comprise a content distribution network(s). A "content delivery network" or "content distribution network" (CDN) generally refers to a distributed content delivery system that comprises a collection of computers or computing devices linked by a network or networks. A CDN may employ software, systems, protocols or techniques to facilitate various services, such as storage, caching, communication of content, or streaming media or applications. A CDN may also enable an entity to operate or manage another's site infrastructure, in whole or in part.

The content server 806 may include a device that includes a configuration to provide content via a network to another device. A content server 806 may, for example, host a site or service, such as streaming media site/service (e.g., Netflix®), an email platform or social networking site, or a personal user site (such as a blog, vlog, online dating site, and the like). A content server 806 may also host a variety of other sites, including, but not limited to business sites, educational sites, dictionary sites, encyclopedia sites, wikis, financial sites, government sites, and the like. Devices that may operate as content server 806 include personal computers desktop computers, multiprocessor systems, microprocessor-based or programmable consumer electronics, network PCs, servers, and the like.

Content server 806 can further provide a variety of services that include, but are not limited to, streaming and/or downloading media services, search services, email services, photo services, web services, social networking services, news services, third-party services, audio services, video services, instant messaging (IM) services, SMS services, MMS services, FTP services, voice over IP (VOIP) services, or the like. Such services, for example a video application and/or video platform, can be provided via the application server 808, whereby a user is able to utilize such service upon the user being authenticated, verified or identified by the service. Examples of content may include images, text, audio, video, or the like, which may be processed in the form of physical signals, such as electrical signals, for example, or may be stored in memory, as physical states, for example.

Moreover, although FIG. 25 illustrates servers 806, 808, 820 and 830 as single computing devices, respectively, the disclosure is not so limited. For example, one or more functions of servers 806, 808, 820 and/or 830 may be distributed across one or more distinct computing devices. Moreover, in one embodiment, servers 806, 808, 820 and/or 830 may be integrated into a single computing device, without departing from the scope of the present disclosure.

Figure 26:
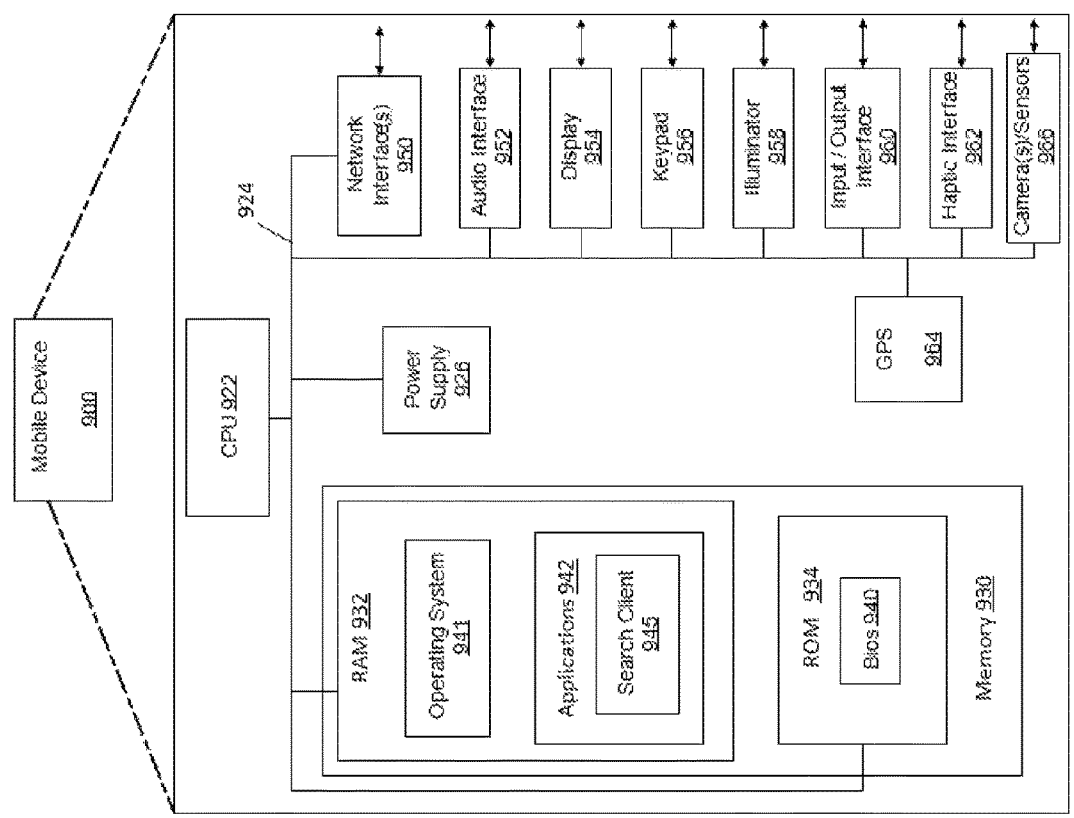
FIG. 26 is an exemplary block diagram illustrating components of a mobile device.

FIG. 26 is a schematic diagram illustrating a client device showing an example embodiment of a client device that may be used within the present disclosure. Client device 900 may include many more or less components than those shown in FIG. 26. However, the components shown are sufficient to disclose an illustrative embodiment for implementing the present disclosure. Client device 900 may represent, for example, client devices discussed above in relation to FIG. 26.

As shown in the figure, client device 900 includes a processing unit (CPU) 922 in communication with a mass memory 930 via a bus 924. Client device 900 also includes a power supply 926, one or more network interfaces 950, an audio interface 952, a display 954, a keypad 956, an illuminator 958, an input/output interface 960, a haptic interface 962, an optional global positioning systems (GPS) receiver 964 and a camera(s) or other optical, thermal or electromagnetic sensors 966. Device 900 can include one camera/sensor 966, or a plurality of cameras/sensors 966, as understood by those of skill in the art. The positioning of the camera(s)/sensor(s) 966 on device 900 can change per device 900 model, per device 900 capabilities, and the like, or some combination thereof.

Power supply 926 provides power to Client device 900. A rechargeable or non-rechargeable battery may be used to provide power. The power may also be provided by an external power source, such as an AC adapter or a powered docking cradle that supplements and/or recharges a battery.

Client device 900 may optionally communicate with a base station (not shown), or directly with another computing device. Network interface 950 includes circuitry for coupling Client device 900 to one or more networks, and is constructed for use with one or more communication protocols and technologies as discussed above. Network interface 950 is sometimes known as a transceiver, transceiving device, or network interface card (NIC).

Audio interface 952 is arranged to produce and receive audio signals such as the sound of a human voice. For example, audio interface 952 may be coupled to a speaker and microphone (not shown) to enable telecommunication with others and/or generate an audio acknowledgement for some action. Display 954 may be a liquid crystal display (LCD), gas plasma, light emitting diode (LED), or any other type of display used with a computing device. Display 954 may also include a touch sensitive screen arranged to receive input from an object such as a stylus or a digit from a human hand.

Keypad 956 may comprise any input device arranged to receive input from a user. For example, keypad 956 may include a push button numeric dial, or a keyboard. Keypad 956 may also include command buttons that are associated with selecting and sending images. Illuminator 958 may provide a status indication and/or provide light. Illuminator 958 may remain active for specific periods of time or in response to events. For example, when illuminator 958 is active, it may backlight the buttons on keypad 956 and stay on while the client device is powered. Also, illuminator 958 may backlight these buttons in various patterns when particular actions are performed, such as dialing another client device. Illuminator 958 may also cause light sources positioned within a transparent or translucent case of the client device to illuminate in response to actions.

Client device 900 also comprises input/output interface 960 for communicating with external devices, such as a headset, or other input or output devices not shown in FIG. 26. Input/output interface 960 can utilize one or more communication technologies, such as USB, infrared, Bluetooth™, or the like. Haptic interface 962 is arranged to provide tactile feedback to a user of the client device. For example, the haptic interface may be employed to vibrate client device 900 in a particular way when the Client device 900 receives a communication from another user.

Optional GPS transceiver 964 can determine the physical coordinates of Client device 900 on the surface of the Earth, which typically outputs a location as latitude and longitude values. GPS transceiver 964 can also employ other geo-positioning mechanisms, including, but not limited to, triangulation, assisted GPS (AGPS), E-OTD, CI, SAI, ETA, BSS or the like, to further determine the physical location of Client device 900 on the surface of the Earth. It is understood that under different conditions, GPS transceiver 964 can determine a physical location within millimeters for Client device 900; and in other cases, the determined physical location may be less precise, such as within a meter or significantly greater distances. In one embodiment, however, Client device may through other components, provide other information that may be employed to determine a physical location of the device, including for example, a MAC address, Internet Protocol (IP) address, or the like.

Mass memory 930 includes a RAM 932, a ROM 934, and other storage means. Mass memory 930 illustrates another example of computer storage media for storage of information such as computer readable instructions, data structures, program modules or other data. Mass memory 930 stores a basic input/output system ("BIOS") 940 for controlling low-level operation of Client device 900. The mass memory also stores an operating system 941 for controlling the operation of Client device 900. It will be appreciated that this component may include a general purpose operating system such as a version of UNIX, or LINUX™, or a specialized client communication operating system such as Windows Client™, or the Symbian® operating system. The operating system may include, or interface with a Java virtual machine module that enables control of hardware components and/or operating system operations via Java application programs.

Memory 930 further includes one or more data stores, which can be utilized by Client device 900 to store, among other things, applications 942 and/or other data. For example, data stores may be employed to store information that describes various capabilities of Client device 900. The information may then be provided to another device based on any of a variety of events, including being sent as part of a header during a communication, sent upon request, or the like. At least a portion of the capability information may also be stored on a disk drive or other storage medium (not shown) within Client device 900.

Applications 942 may include computer executable instructions which, when executed by Client device 900, transmit, receive, and/or otherwise process audio, video, images, and enable telecommunication with a server and/or another user of another client device. Other examples of application programs or "apps" in some embodiments include browsers, calendars, contact managers, task managers, transcoders, photo management, database programs, word processing programs, security applications, spreadsheet programs, games, search programs, and so forth. Applications 942 may further include search client 945 that is configured to send, to receive, and/or to otherwise process a search query and/or search result using any known or to be known communication protocols. Although a single search client 945 is illustrated it should be clear that multiple search clients may be employed. For example, one search client may be configured to enter a search query message, where another search client manages search results, and yet another search client is configured to manage serving advertisements, IMs, emails, and other types of known messages, or the like.

Figure 27:
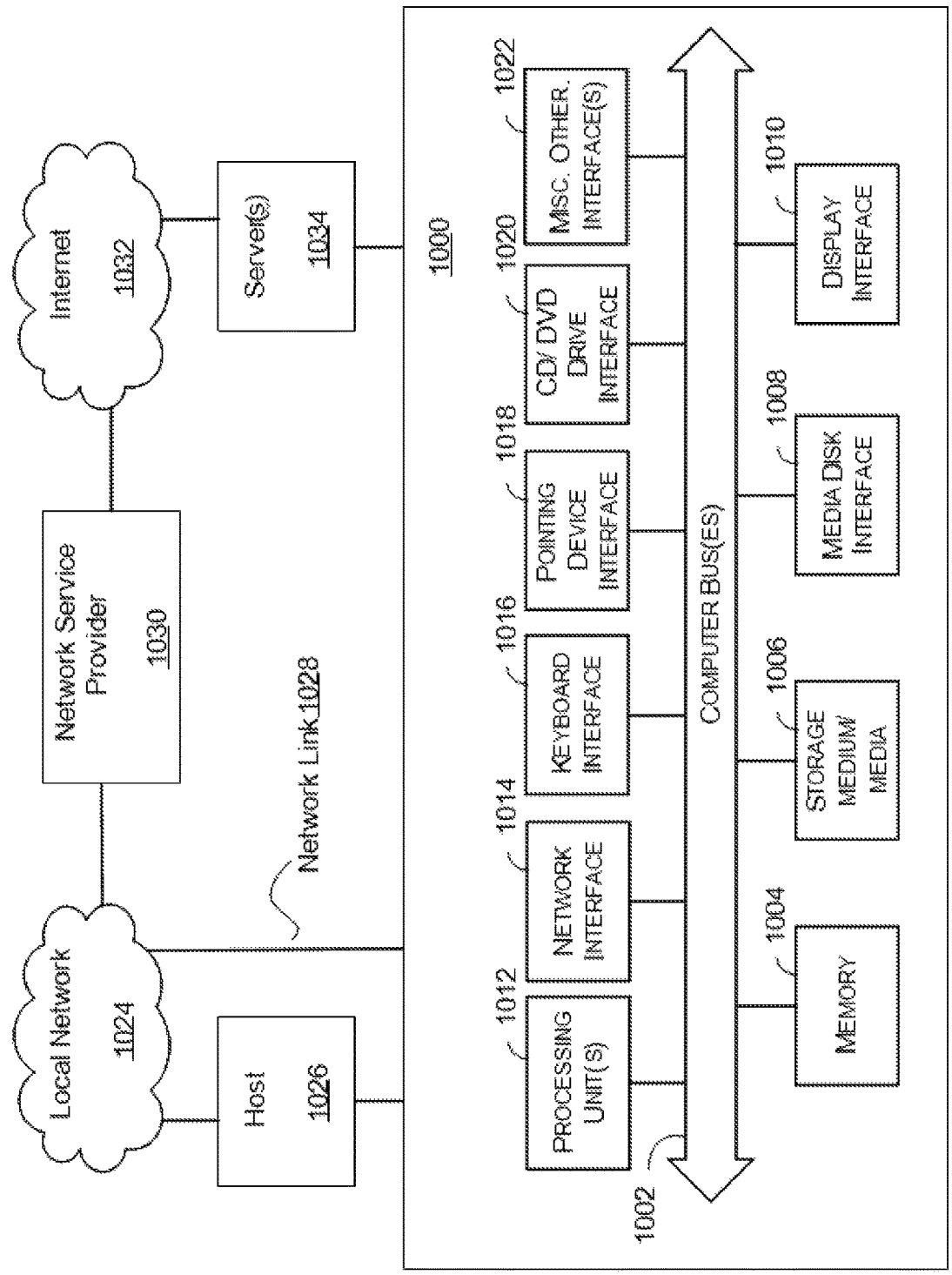
FIG. 27 is a block diagram of an exemplary embodiment of an internal architecture of a computing device.

As shown in FIG. 27, internal architecture 1000 of a computing device(s), computing system, computing platform and the like can include one or more processing units, processors, or processing cores, (also referred to herein as CPUs) 1012, which interface with at least one computer bus 1002. Also interfacing with computer bus 1002 are, for example, computer-readable medium, or media, 1006, network interface 1014, memory 1004, e.g., random access memory (RAM), run-time transient memory, read only memory (ROM), media disk drive interface 1020 as an interface for a drive that can read and/or write to media including removable media such as floppy, CD-ROM, DVD, media, display interface 1010 as interface for a monitor or other display device, keyboard interface 1016 as interface for a keyboard, pointing device interface 1018 as an interface for a mouse or other pointing device, and miscellaneous other interfaces 1022 not shown individually, such as parallel and serial port interfaces and a universal serial bus (USB) interface.

Memory 1004 interfaces with computer bus 1002 so as to provide information stored in memory 1004 to CPU 1012 during execution of software programs such as an operating system, application programs, device drivers, and software modules that comprise program code, and/or computer executable process steps, incorporating functionality described herein, e.g., one or more of process flows described herein. CPU 1012 first loads computer executable process steps from storage, e.g., memory 1004, computer readable recording or storage medium/media 1006, removable media drive or media disk interface 1008, and/or other storage device. CPU 1012 can then execute the stored process steps in order to execute the loaded computer-executable process steps. Stored data, e.g., data stored by a storage device, can be accessed by CPU 1012 during the execution of computer-executable process steps.

Persistent storage, e.g., medium/media 1006, can be used to store an operating system and one or more application programs. Persistent storage can also be used to store device drivers, such as one or more of a digital camera driver, monitor driver, printer driver, scanner driver, or other device drivers, web pages, content files, playlists and other files. Persistent storage can further include program modules and data files used to implement one or more embodiments of the present disclosure.

Network link 1028 typically provides information communication using transmission media through one or more networks to other devices that use or process the information. For example, network link 1028 may provide a connection through local network 1024 to a host computer 1026 or to equipment operated by a Network or Internet Service Provider (ISP) 1030. ISP equipment in turn provides data communication services through the public, worldwide packet-switching communication network of networks now commonly referred to as the Internet 1032.

A computer called a server host 1034 connected to the Internet 1032 hosts a process that provides a service in response to information received over the Internet 1032. For example, server host 1034 hosts a process that provides information representing video data for presentation at display 1010. It is contemplated that the components of system 1000 can be deployed in various configurations within other computer systems, e.g., host and server.

At least some embodiments of the present disclosure are related to the use of computer system 1000 for implementing some or all of the techniques described herein. According to one embodiment, those techniques are performed by computer system 1000 in response to processing unit 1012 executing one or more sequences of one or more processor instructions contained in memory 1004. Such instructions, also called computer instructions, software and program code, may be read into memory 1004 from another computer-readable medium 1006 such as storage device or network link. Execution of the sequences of instructions contained in memory 1004 causes processing unit 1012 to perform one or more of the method steps described herein. In alternative embodiments, hardware, such as ASIC, may be used in place of or in combination with software. Thus, embodiments of the present disclosure are not limited to any specific combination of hardware and software, unless otherwise explicitly stated herein.

The signals transmitted over network link and other networks through communications interface, carry information to and from computer system 1000. Computer system 1000 can send and receive information, including program code, through the networks, among others, through network link and communications interface. In an example using the Internet, a server host transmits program code for a particular application, requested by a message sent from computer, through Internet, ISP equipment, local network and communications interface. The received code may be executed by processor 1002 as it is received, or may be stored in memory 1004 or in storage device or other non-volatile storage for later execution, or both.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

What is claimed is:

1. A system for collecting and analyzing medical data, comprising:
   a data management system for collecting and storing medical information relating to a user, the medical information including data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires to create a digital representation of the user;
   wherein the data comprises a plurality of medical information values representative of the medical information;
   wherein the data management system is configured to:
      store the plurality of medical information values as a plurality of medical attributes in a plurality of medical objects of at least one medical object type;
      wherein the at least one medical object type comprises:
         a condition type,
         a symptom type, a treatment type,
a procedure type,
a provider type, and
a lab test type;
wherein each medical object of the plurality of medical objects comprises an instance of the at least one medical object type, the instance comprising at least one medical attribute of the plurality of medical attributes associated with the at least one medical object type; and
generate an assignment of each medical object of the plurality of medical objects to at least one other medical object of the plurality of medical objects, the assignment based at least in part on at least one predefined relationship associated with each medical object of the plurality of medical objects,
the assignment further comprises relationships between:
questions and responses to the questions and at least one of:
scoring rules related to symptoms for each medical object, the scoring rules comprising one or more assignments of weights for the symptoms, or
at least one treatment;
a knowledge creation engine in communication with the data management system, the knowledge creation engine configured to analyze the stored medical information, based at least in part on the plurality of medical objects of the at least one medical object type, the assignment of each medical object and at least one scoring, for creating at least one of personalized medical advice for the user and general scientific information relating to a medical condition, and
a display in communication with the data management system and the knowledge creation engine, the display configured to present a digital representation of the user based on the stored medical information.

2. The system of claim 1, further comprising a healthcare provider engine in communication with the data management system and that is configured to generate a healthcare provider preparation document that captures information relating to the stored medical information to present a current state of the user to a healthcare provider before a scheduled appointment with the healthcare provider.

3. The system of claim 1, wherein the one or more dynamic questionnaires includes a plurality of questions determined by a rules engine based on the stored medical information.

4. The system of claim 1, further comprising an insight engine that is configured to generate insight information for the user using the stored medical information, the insight information being at least partially based on user attributes of a subset of users having stored data similar to the user.

5. The system of claim 4, wherein the insight information comprises at least one of aggregated user data, health assessments, personalized medical advice, customized reports for clinicians, research results, user givebacks and customized reports related to genome/exome sequencing, transcriptomics, metabolomics, proteomics, immunosignature, and microflora/fauna.

6. A system for aggregating and analyzing data from a community, comprising:
a data management system configured to receive and store data from a plurality of users, the data relating to medical information and health status information for each of the plurality of users;
wherein the data comprises a plurality of medical information values representative of the medical information;
wherein the data management system is configured to:
store the plurality of medical information values as a plurality of medical attributes in a plurality of medical objects of at least one medical object type;
wherein the at least one medical object type comprises: a condition type, a symptom type, a treatment type, a procedure type, a provider type, and a lab test type;
wherein each medical object of the plurality of medical objects comprises an instance of the at least one medical object type, the instance comprising at least one medical attribute of the plurality of medical attributes associated with the at least one medical object type; and
generate an assignment of each medical object of the plurality of medical objects to at least one other medical object of the plurality of medical objects, the assignment based at least in part on at least one predefined relationship associated with each medical object of the plurality of medical objects,
the assignment further comprises relationships between: questions and responses to the questions and at least one of: scoring rules related to symptoms for each medical object, the scoring rules comprising one or more assignments of weights for the symptoms, or at least one treatment;
a processor in communication with the data management system, the processor configured to perform the steps of
analyzing the stored data for the plurality of users, based at least in part on the plurality of medical objects of the at least one medical object type, the assignment of each medical object and at least one scoring;
generating insight information for at least one of the plurality of users using the analyzed data, the insight information being at least partially based on user attributes of a subset of the plurality of users having stored data substantially similar to the at least one of the plurality of users;
wherein the data includes at least one of an electronic health record (EHR), patient reported outcomes (PROs), one or more biological samples, data from one or more wearable devices, data from one or more sensors configured to collect data relating to a biological condition of the user, data from one or more medical devices, and results from one or more dynamic questionnaires to create a digital representation of the at least one user.

7. The system of claim 6, wherein the insight information comprises at least one of aggregated user data, health assessments, personalized medical advice, customized reports for clinicians, research results, user givebacks and customized reports related to genome/exome sequencing, transcriptomics, metabolomics, proteomics, immunosignature, and microflora/fauna.

8. A method for collecting and analyzing data, comprising:
   aggregating medical information relating to a user, the medical information including data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires to create a digital representation of the user;
   wherein the data comprises a plurality of medical information values representative of the medical information;
   wherein a data management system is configured to:
      store the plurality of medical information values as a plurality of medical attributes in a plurality of medical objects of at least one medical object type;
         wherein the at least one medical object type comprises: a condition type, a symptom type, a treatment type, a procedure type, a provider type, and a lab test type;
         wherein each medical object of the plurality of medical objects comprises an instance of the at least one medical object type, the instance comprising at least one medical attribute of the plurality of medical attributes associated with the at least one medical object type; and
      generate an assignment of each medical object of the plurality of medical objects to at least one other medical object of the plurality of medical objects, the assignment based at least in part on at least one predefined relationship associated with each medical object of the plurality of medical objects,
         the assignment further comprises relationships between: questions and responses to the questions and at least one of: scoring rules related to symptoms for each medical object, the scoring rules comprising one or more assignments of weights for the symptoms, or at least one treatment;
   analyzing the aggregated medical information using a computational knowledge engine based at least in part on the plurality of medical objects of the at least one medical object type, the assignment of each medical object and at least one scoring; and
   generating insight information using the computational knowledge engine, the insight information relating to the aggregated medical information for presentation to the user on a display, the insight information being at least partially based on user attributes of a plurality of users having medical profiles similar to the user.

9. The method of claim 8, wherein the one or more dynamic questionnaires includes a plurality of questions determined by a rules engine based on the aggregated medical information.

10. The method of claim 9, wherein the rules engine determines an order of the plurality of questions.

11. The method of claim 8, wherein the insight information comprises unique information for a user at least partially based on information from the plurality of users with similar medical profiles.

12. The method of claim 11, wherein the insight information comprises at least one of aggregated user data, health assessments, personalized medical advice, customized reports for clinicians, research results, user givebacks and customized reports related to genome/exome sequencing, transcriptomics, metabolomics, proteomics, immunosignature, and microflora/fauna.

13. The method of claim 11, wherein the insight information comprises a visual representation of a disease, a user's life strategy, or other information collected and/or processed by the computational knowledge engine, and is presented to a user to visually convey an understanding of their condition/illness or health status.

14. The method of claim 8, further comprising generating a healthcare provider preparation document that captures information relating to the aggregated medical information to present a current state of the user to the healthcare provider before a scheduled appointment with the healthcare provider.

15. The method of claim 8, further comprising determining which data to collect and at what frequency and priority using the aggregated medical information.

16. The method of claim 8, further comprising using a phenotype measurement system to determine which data to collect.

17. The method of claim 16, wherein the phenotype measurement system is configured to determine state changes in a status of the user for triggering the collection of biological samples.

18. A method for collecting and analyzing data, comprising:
   aggregating medical information relating to a plurality of users, the medical information including data from at least one of an electronic health record (EHR), patient reported outcomes (PROs), one or more biological samples, one or more wearable devices, one or more sensors configured to collect data relating to a biological condition of the user, one or more medical devices, and one or more dynamic questionnaires;
   wherein the data comprises a plurality of medical information values representative of the medical information;
   wherein a data management system is configured to:
      store the plurality of medical information values as a plurality of medical attributes in a plurality of medical objects of at least one medical object type;
         wherein the at least one medical object type comprises: a condition type, a symptom type, a treatment type, a procedure type, a provider type, and a lab test type;
         wherein each medical object of the plurality of medical objects comprises an instance of the at least one medical object type, the instance comprising at least one medical attribute of the plurality of medical attributes associated with the at least one medical object type; and
      generate an assignment of each medical object of the plurality of medical objects to at least one other medical object of the plurality of medical objects, the assignment based at least in part on at least one predefined relationship associated with each medical object of the plurality of medical objects,
         the assignment further comprises relationships between: questions and responses to the questions and at least one of: scoring rules related to symptoms for each medical object, the scoring rules comprising one or more assignments of weights for the symptoms, or at least one treatment;

analyzing the aggregated medical information using a computational knowledge engine based at least in part on the plurality of medical objects of the at least one medical object type, the assignment of each medical object and at least one scoring; and generating research information using the analyzed aggregated medical information, the research information including results of one or more experiments run using the aggregated medical information of a subset of the plurality of users having user attributes related to one another.

19. The method of claim 18, wherein the one or more experiments are clinical trials.

20. The method of claim 19, further comprising communicating with the subset of a plurality of users consent information for participation in the clinical trials for which the subset of the plurality of users are determined to be eligible based on the aggregated medical information.

* * * * *